United States Patent
Erskine

(10) Patent No.: US 9,408,632 B2
(45) Date of Patent: Aug. 9, 2016

(54) NEEDLE SHIELDING DEVICE

(75) Inventor: Timothy J. Erskine, Sister Bay, WI (US)

(73) Assignee: Erskine Medical LLC, High Falls, NY (US)

( * ) Notice: Subject to any disclaimer, the term of this patent is extended or adjusted under 35 U.S.C. 154(b) by 338 days.

(21) Appl. No.: 14/110,352

(22) PCT Filed: Apr. 6, 2012

(86) PCT No.: PCT/US2012/032578
§ 371 (c)(1),
(2), (4) Date: Oct. 7, 2013

(87) PCT Pub. No.: WO2012/139034
PCT Pub. Date: Oct. 11, 2012

(65) Prior Publication Data
US 2014/0025009 A1    Jan. 23, 2014

Related U.S. Application Data

(60) Provisional application No. 61/472,881, filed on Apr. 7, 2011.

(51) Int. Cl.
*A61M 5/32* (2006.01)
*A61B 17/34* (2006.01)
*A61M 25/06* (2006.01)

(52) U.S. Cl.
CPC ........ *A61B 17/3494* (2013.01); *A61M 25/0606* (2013.01); *A61M 25/0618* (2013.01); *A61M 5/3273* (2013.01); *A61M 2005/325* (2013.01)

(58) Field of Classification Search
CPC ..................... A61M 5/3273; A61M 2005/325; A61M 25/0618; A61M 25/0625; A61M 25/0631; A61M 25/0693
See application file for complete search history.

(56) References Cited

U.S. PATENT DOCUMENTS

| 2,798,487 A | 7/1957 | Ferguson |
| 3,459,183 A | 8/1969 | Ring et al. |

(Continued)

FOREIGN PATENT DOCUMENTS

| CN | 1145813 A | 3/1997 |
| CN | 1547493 A | 11/2004 |

(Continued)

OTHER PUBLICATIONS

Patent Cooperation Treaty, Notification of Transmittal of the International Search Report and the Written Opinion of the International Searching Authority, or the Declaration for PCT/US12/32578 dated Aug. 3, 2012, 26 pages.

(Continued)

*Primary Examiner* — Emily Schmidt
(74) *Attorney, Agent, or Firm* — Hoffman Warnick LLC

(57) ABSTRACT

A needle-based medical device and method of manufacturing the same are disclosed. A needle device includes a hub having a longitudinal axis; a needle having a sharp distal tip; and a needle shield assembly associated with the needle and moveable from a non-shielding position to a shielding position. In the shielding position, the sharp distal tip is covered by at least part of the needle shield assembly. A bushing disposed about the needle, and a latch for engaging with the hub when the needle shield assembly is in the non-shielding position are further provided.

19 Claims, 51 Drawing Sheets

(56) References Cited

U.S. PATENT DOCUMENTS

| | | |
|---|---|---|
| 4,588,398 A | 5/1986 | Daugherty et al. |
| 4,596,563 A | 6/1986 | Pande |
| 4,755,170 A | 7/1988 | Golden |
| 4,762,516 A | 8/1988 | Luther et al. |
| 4,778,453 A | 10/1988 | Lopez |
| 4,790,828 A | 12/1988 | Dombrowski et al. |
| 4,832,696 A | 5/1989 | Luther et al. |
| 4,834,718 A | 5/1989 | McDonald |
| 4,846,809 A | 7/1989 | Sims |
| 4,863,436 A | 9/1989 | Glick |
| 4,887,998 A | 12/1989 | Martin et al. |
| 4,927,414 A | 5/1990 | Kulli |
| 4,929,241 A | 5/1990 | Kulli |
| 4,931,048 A | 6/1990 | Lopez |
| 4,944,725 A | 7/1990 | McDonald |
| 4,952,207 A | 8/1990 | Lemieux |
| 4,978,344 A | 12/1990 | Dombrowski et al. |
| 5,049,136 A | 9/1991 | Johnson |
| 5,059,180 A | 10/1991 | McLees |
| 5,116,326 A | 5/1992 | Schmidt |
| 5,120,320 A | 6/1992 | Fayngold |
| 5,160,325 A | 11/1992 | Nichols et al. |
| 5,215,528 A | 6/1993 | Purdy et al. |
| RE34,416 E | 10/1993 | Lemieux |
| 5,261,895 A | 11/1993 | Kablik |
| 5,300,045 A | 4/1994 | Plassche, Jr. |
| 5,304,151 A | 4/1994 | Kuracina |
| 5,322,517 A | 6/1994 | Sircom et al. |
| 5,328,482 A | 7/1994 | Sircom et al. |
| 5,334,158 A | 8/1994 | McLees |
| 5,344,408 A | 9/1994 | Partika |
| 5,360,408 A | 11/1994 | Vaillancourt |
| 5,360,497 A | 11/1994 | Schneider et al. |
| 5,376,075 A | 12/1994 | Haughton et al. |
| 5,429,611 A | 7/1995 | Rait |
| 5,447,501 A | 9/1995 | Karlsson et al. |
| 5,458,658 A | 10/1995 | Sircom |
| 5,466,223 A | 11/1995 | Bressler et al. |
| 5,558,651 A | 9/1996 | Crawford et al. |
| 5,582,597 A | 12/1996 | Brimhall et al. |
| 5,584,809 A | 12/1996 | Gaba |
| 5,599,310 A | 2/1997 | Bogert |
| 5,601,536 A | 2/1997 | Crawford et al. |
| 5,611,781 A | 3/1997 | Sircom et al. |
| 5,662,610 A | 9/1997 | Sircom |
| 5,669,927 A | 9/1997 | Boebel et al. |
| 5,683,365 A | 11/1997 | Brown et al. |
| 5,690,619 A | 11/1997 | Erskine |
| 5,697,907 A | 12/1997 | Gaba |
| 5,700,250 A | 12/1997 | Erskine |
| 5,718,688 A | 2/1998 | Wozencroft |
| 5,755,699 A | 5/1998 | Blecher et al. |
| 5,795,339 A | 8/1998 | Erskine |
| 5,853,393 A | 12/1998 | Bogert |
| 5,879,337 A | 3/1999 | Kuracina et al. |
| 5,951,515 A | 9/1999 | Osterlind |
| 5,951,525 A | 9/1999 | Thorne et al. |
| 6,001,080 A | 12/1999 | Kuracina et al. |
| 6,004,292 A | 12/1999 | Battiato et al. |
| 6,004,294 A | 12/1999 | Brimhall et al. |
| 6,117,108 A | 9/2000 | Woehr et al. |
| 6,210,371 B1 | 4/2001 | Shaw |
| 6,221,047 B1 | 4/2001 | Greene et al. |
| 6,234,999 B1 | 5/2001 | Wemmert et al. |
| 6,379,333 B1 | 4/2002 | Brimhall et al. |
| 6,443,929 B1 | 9/2002 | Kuracina |
| 6,595,955 B2 | 7/2003 | Ferguson et al. |
| 6,629,959 B2 | 10/2003 | Kuracina et al. |
| 6,659,984 B2 | 12/2003 | Crawford et al. |
| 6,689,102 B2 | 2/2004 | Greene |
| 6,695,814 B2 | 2/2004 | Greene et al. |
| 6,743,186 B2 | 6/2004 | Crawford et al. |
| 6,749,588 B1 | 6/2004 | Howell et al. |
| 6,761,706 B2 | 7/2004 | Vaillancourt |
| 6,786,891 B2 | 9/2004 | Hiejima |
| 6,860,871 B2 | 3/2005 | Kuracina et al. |
| 6,881,202 B2 | 4/2005 | Coleman et al. |
| 6,976,976 B2 | 12/2005 | Doyle |
| RE38,996 E | 2/2006 | Crawford et al. |
| 6,997,902 B2 | 2/2006 | Thorne et al. |
| 7,125,397 B2 | 10/2006 | Woehr et al. |
| 7,144,387 B2 | 12/2006 | Millerd |
| 7,264,613 B2 | 9/2007 | Woehr et al. |
| 7,303,548 B2 | 12/2007 | Rhad et al. |
| 7,322,963 B2 | 1/2008 | Goh |
| 7,387,616 B2 | 6/2008 | Li |
| 7,611,499 B2 | 11/2009 | Woehr et al. |
| 7,811,261 B2 | 10/2010 | Rubinstein et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 8,100,858 B2 | 1/2012 | Woehr et al. |
| 8,235,945 B2 | 8/2012 | Baid |
| 8,251,950 B2 | 8/2012 | Albert et al. |
| 8,545,454 B2 | 10/2013 | Kuracina et al. |
| 8,556,853 B2 | 10/2013 | Vaillancourt |
| 2001/0047156 A1 | 11/2001 | Parker |
| 2002/0111566 A1 | 8/2002 | Crawford et al. |
| 2002/0169418 A1* | 11/2002 | Menzi ............... A61M 25/0637 604/164.07 |
| 2003/0036731 A1 | 2/2003 | Wilkinson et al. |
| 2003/0105431 A1 | 6/2003 | Howell |
| 2003/0216687 A1 | 11/2003 | Hwang |
| 2003/0220587 A1 | 11/2003 | Swenson |
| 2003/0220612 A1 | 11/2003 | Hiejima |
| 2004/0049155 A1 | 3/2004 | Schramm |
| 2004/0049163 A1 | 3/2004 | Murashita |
| 2004/0167385 A1 | 8/2004 | Rioux et al. |
| 2004/0225262 A1 | 11/2004 | Fathallah et al. |
| 2005/0015054 A1 | 1/2005 | Chen |
| 2005/0119627 A1 | 6/2005 | Crawford |
| 2007/0100297 A1 | 5/2007 | Woehr et al. |
| 2008/0171986 A1 | 7/2008 | Baid |
| 2009/0131876 A1 | 5/2009 | Coyne |
| 2009/0163861 A1 | 6/2009 | Carlyon |
| 2009/0281499 A1 | 11/2009 | Harding et al. |
| 2010/0016804 A1 | 1/2010 | Muskatello et al. |
| 2010/0191188 A1 | 7/2010 | Harding et al. |
| 2010/0191189 A1 | 7/2010 | Harding et al. |
| 2010/0222746 A1 | 9/2010 | Burkholz |
| 2010/0249707 A1 | 9/2010 | Woehr et al. |
| 2012/0220956 A1* | 8/2012 | Kuracina ............ A61M 5/3273 604/263 |

FOREIGN PATENT DOCUMENTS

| | | |
|---|---|---|
| DE | 3802353 A1 | 8/1989 |
| EP | 0443735 A1 | 8/1991 |
| EP | 0747085 A2 | 12/1996 |
| EP | 0749761 A1 | 12/1996 |
| EP | 0750916 A2 | 1/1997 |
| EP | 0826388 A2 | 3/1998 |
| EP | 0995459 A2 | 4/2000 |
| EP | 1291035 A2 | 3/2003 |
| EP | 1369142 B1 | 8/2005 |
| EP | 1604700 A1 | 12/2005 |
| EP | 2016964 A1 | 1/2009 |
| EP | 2075029 A1 | 7/2009 |
| FR | 2767480 A1 | 2/1999 |
| JP | H04102462 A | 4/1992 |
| JP | 2002248168 A | 9/2002 |
| JP | 2002330946 A | 11/2002 |
| JP | 2002539897 T | 11/2002 |
| WO | 9211885 A1 | 7/1992 |
| WO | 9908742 | 2/1999 |
| WO | 0057940 A1 | 10/2000 |
| WO | 0069501 | 11/2000 |
| WO | 0156642 A1 | 8/2001 |
| WO | 03011381 A1 | 2/2003 |
| WO | 2004043521 A1 | 5/2004 |
| WO | 2006096633 A1 | 9/2006 |
| WO | 2006096634 A1 | 9/2006 |
| WO | 2006096635 A1 | 9/2006 |
| WO | 2006096636 A1 | 9/2006 |

(56) References Cited

FOREIGN PATENT DOCUMENTS

| WO | 2007022373 A2 | 2/2007 |
|---|---|---|
| WO | 2010101573 A1 | 9/2010 |
| WO | 2010110789 A1 | 9/2010 |
| WO | 2012075402 A1 | 6/2012 |
| WO | 2012075421 A1 | 6/2012 |

OTHER PUBLICATIONS

European Patent Office, European Search Report for EP12169737 dated Jul. 25, 2012, 4 pages.
European Patent Office, European Search Report for EP12169713 dated Jul. 26, 2012, 5 pages.
Shamsudin, Substantive/Modified Substantive Examination and Search Report, Application No. PI 20071467, Mar. 15, 2013, 4 pages.
Ehrsam, Supplementary European Search Report, Application No. EP 09 84 1250, Feb. 26, 2013, 5 pages.
Omgba, Office Action Correspondence, U.S. Appl. No. 13/114,589, Apr. 10, 2013, 15 pages.
Becamel, International Application No. PCT/US2009/036197, PCT International Preliminary Report on Patentability and Written Opinion of the International Searching Authority, Sep. 15, 2011, 10 pages.
Price, Office Action Communication for U.S. Appl. No. 11/817,892 dated Oct. 6, 2011, 14 pages.
Patent Cooperation Treaty, International Preliminary Report on Patentability and Written Opinion of the International Searching Authority for PCT/US2009/038246 dated Oct. 6, 2011, 7 pages.
Canadian Intellectual Property Office, Office Action for Application No. 2,599,943 dated Oct. 13, 2011, 2 pages.
IP Australia, Examiners First Report on Patent Application No. 2010203121 dated Nov. 4, 2011, 2 pages.
Desanto, Office Action Communication for U.S. Appl. No. 11/817,890 dated Jun. 6, 2013, 19 pages.
Patent Cooperation Treaty, International Preliminary Report on Patentability for PCT/US2011/063081 dated Jun. 4, 2013, 7 pages.
Patent Cooperation Treaty, International Preliminary Report on Patentability for PCT/US2011/063118 dated Jun. 4, 2013, 8 pages.
European Patent Office, Intention to Grant for EP Application No. 06 737 126.0 dated Jun. 17, 2013, 92 pages.
Canadian Patent Office, Notice of Allowance for CA Application No. 2,599,943 dated Jul. 3, 2013, 1 page.
Desanto, Notice of Allowance and Fee(s) Due for U.S. Appl. No. 11/817,890 dated Sep. 17, 2013, 17 pages.
Patent Cooperation Treaty, Notification of Transmittal of the International Search Report and the Written Opinion of the International Searching Authority, or the Declaration for PCT/US2011/063118 dated Apr. 3, 2012, 17 pages.
Patent Cooperation Treaty, Notification of Transmittal of the International Search Report and the Written Opinion of the International Searching Authority, or the Declaration for PCT/US2011/063081 dated Mar. 22, 2012, 10 pages.
Desanto, Office Action Communication for U.S. Appl. No. 11/817,890 dated Apr. 30, 2012, 14 pages.
European Patent Office, Supplementary European Search Report for EP09842422 dated Aug. 27, 2012, 7 pages.
Desanto, Office Action Communication for U.S. Appl. No. 11/817,890 dated Oct. 11, 2012, 26 pages.
Final Office Action for U.S. Appl. No. 11/817,891, dated Jun. 9, 2015, 14 pages.
Office Action for U.S. Appl. No. 13/997,973, dated Mar. 12, 2015, 54 pages.
Price, U.S. Appl. No. 11/817,891, Non-Final Office Action, Sep. 16, 2014, 94 pgs.
Office Action for JP Application No. 2014-504040, dated Jun. 30, 2015, 6 pages.
Office Action for CN Application No. 201180066317, dated Jun. 17, 2015, 5 pages.
Office Action for U.S. Appl. No. 13/997,969, dated Jul. 16, 2015, 85 pages.
Notice of Allowance and Fee(s) Due for U.S. Appl. No. 13/997,973, dated Jul. 31, 2015, 10 pages.
Communication Pursuant to Article 94(3) EPC for EP Application No. 12169713.0, dated Aug. 4, 2015, 5 pages.
Second Office Action for CN Application No. 201180066325.4, dated Jun. 16, 2015, 7 pages.
Office Action for CA Application No. 2,822,982, dated Sep. 30, 2014, 2 pages.
Office Action for CA Application No. 2,828,741, dated Sep. 25, 2014, 2 pages.
Office Action for CA Application No. 2,823,016, dated Jan. 27, 2015, 4 pages.
First Office Action for CN Application No. 201280015426.3, dated Feb. 2, 2015, 12 pages.
Patent Examination Report No. 2 for AU Application No. 2012239937, dated Mar. 25, 2015, 4 pages.
Erskine, Office Communication for U.S. Appl. No. 11/817,687 dated Dec. 9, 2010, 19 pages.
Erskine, Mexican Application No. MX/a/2007/010944, Office Action dated Mar. 11, 2011, 4 pages.
Erskine, Japanese Application No. JP07-5616-XY, Decision to Grant a Patent, dated Apr. 5, 2011, 6 pages.
Erskine, Taiwan Application No. 095107585, Office Action, dated Mar. 17, 2011, 3 pages.
Erskine, Mexian Application No. MX/a/2007/010946, Office Action, dated Apr. 2011, 2 pages.
Erskine, Japan Application No. P2008-500802, Notice of Reasons for Rejection, dated Apr. 5, 2011, 4 pages.
Erskine, China Application No. 201010109122.6, Office Action, dated Apr. 1, 2011, 11 pages.
Erskine, Office Action Communication for U.S. Appl. No. 11/817,892 dated Apr. 28, 2011, 25 pages.
Patent Cooperation Treaty, PCT Notification of Transmittal of International Preliminary Report on Patentability for PCT Application No. PCT/US06/07909 dated Aug. 16, 2007, 13 pages.
Erskine, Malaysia Application No. PI20071466, Office Action, dated Aug. 30, 2010, 3 pages.
Erskine, Taiwanese Application No. 095107587, Office Action dated Oct. 12, 2009, 12 pages.
Erskine, Australian Application No. 2006220691, Examiner's First Report on Patent dated Jan. 19, 2009, 2 pages.
Erskine, Chinese Application No. 200680007484, Office Action dated Aug. 21, 2009, 13 pages.
Erskine, Taiwanese Application No. 095107585, Office Action dated Apr. 6, 2009, 9 pages.
Erskine, Taiwanese Application No. 095107585, Office Action dated Oct. 15, 2009, 7 pages.
European Patent Office, European Search Report for Application No. EP06737125, dated Feb. 10, 2010, 7 pages.
Erskine, Canadian Application No. 2,599,943, Office Action dated Dec. 30, 2010, 2 pages.
Erskine, Canadian Application No. 2,599,945, Notice of Allowance dated Nov. 25, 2010, 1 pages.
Erskine, Canadian Application No. 2,599,955, Office Action dated Dec. 21, 2010, 3 pages.
Erskine, Canadian Application No. 2,599,938, Office Action dated Dec. 20, 2010, 2 pages.
Erskine, Japanese Application No. P2008-500805, Final Office Action dated Jan. 25, 2011, 25 pages.
Erskine, Japanese Application No. P2008-500804, Notice to Grant dated Feb. 2, 2011, 6 pages.
Desanto, Office Action Communication for U.S. Appl. No. 11/817,890 dated Aug. 31, 2011, 33 pages.
Osinski, Notice of Allowance & Fee(s) Due for U.S. Appl. No. 11/817,687 dated Jun. 30, 2011, 8 pages.
Erskine, Mexican Application No. MX/A/2007/010943, Office Action dated Jun. 10, 2011, 2 pages.
State Intellectual Property Office of the the People's Republic of China, Notification of the First Office Action for Application No. CN 201180066317 dated Oct. 27, 2014, 19 pages.
Price, Notice of Allowance and Fee(s) Due for U.S. Appl. No. 11/817,892 dated Dec. 19, 2014, 71 pages.

(56) References Cited

OTHER PUBLICATIONS

Third Office Action for Chinese Patent Application No. 201180066325.4, dated Oct. 10, 2015, 7 pages. English language translation provided.
Office Action for Mexican Patent Application No. MX/a/2013/011676, 2 pages.
Notice of Allowance and Fee(s) Due for U.S. Appl. No. 11/817,891, dated Aug. 25, 2015, 14 pages.
Erskine, Australian IP Examination Report No. 2 dated Feb. 25, 2010, Reference No. 30355386/MRF/TLG/tzs, Application No. 2006220690, 2 pages.
Erskine, Canadian Application No. 2,599,943, Office Action dated Nov. 20, 2009, 2 pages.
Erskine, Chinese Application No. 200680007590, Office Action dated May 21, 2010, 4 pages.
Erskine, Australian Application No. 2006220691, Notice of Acceptance dated Jun. 9, 2010, 2 pages.
Erskine, Canadian Application No. 2,599,945, Office Action dated Nov. 13, 2009, 2 pages.
Erskine, Chinese Application No. 200680007484, Notification to Grant Patent Right dated Jun. 11, 2010, 4 pages.
Patent Cooperation Treaty, PCT/US06/07911, PCT International Search Report and Written Opinion, dated Jun. 23, 2006, 8 pages.
Patent Cooperation Treaty, PCT/US06/07911, PCT International Preliminary Report on Patentability, dated Feb. 12, 2007, 4 pages.
Erskine, U.S. Appl. No. 11/817,891, Office Communication dated Jun. 11, 2010, 11 pages.
Erskine, Australian Application No. 2006220692, Examiners First Report on Patent Application dated Oct. 21, 2008, 2 pages.
Erskine, Canadian Application No. 2,599,955, Office Action dated Mar. 5, 2010, 2 pages.
Erskine, Chinese Application No. 200680007485.0, Office Action dated Jun. 19, 2009, 6 pages.
Erskine, Chinese Application No. 200680007485.0, Notification to Grant Patent Right dated Jun. 4, 2010, 5 pages.
Erskine, Japanese Application No. P2008-500805, Office Action dated Apr. 20, 2010, 4 pages.
Erskine, Malaysia Application No. PI 20071465, Substantive Examination Report dated Apr. 30, 2010, 3 pages.
Patent Cooperation Treaty, PCT/US06/07912, PCT International Preliminary Report on Patentability, dated Sep. 20, 2007, 5 pages.
Patent Cooperation Treaty, PCT/US06/07912, PCT International Search Report and Written Opinion, dated Jun. 26, 2006, 8 pages.
Erskine, Taiwanese Application No. 095107584, Decision to Grant Patent dated Mar. 4, 2009, 5 pages.
Erskine, U.S. Appl. No. 11/817,687, Office Communication dated Jun. 30, 2010, 8 pages.
Erskine, U.S. Appl. No. 11/817,687, Office Communication dated Jan. 21, 2010, 9 pages.
Erskine, Australian Application No. 2006220689, Examiners First Report on Patent Application dated Jan. 15, 2009, 3 pages.
Erskine, Australian Application No. 2006220689, Patent Granted dated Jun. 18, 2010, 3 pages.
Erskine, Canadian Application No. 2,599,938, Office Action dated Feb. 23, 2010, 2 pages.
Erskine, Chinese Application No. 200680007548.2, Office Action dated Sep. 4, 2009, 4 pages.
Erskine, Chinese Application No. 200680007548.2, Notification to Grant Patent Right dated Jun. 12, 2010, 4 pages.
Erskine, Australian Application No. 2006220690, Notice of Acceptance dated Jun. 15, 2010, 3 pages.
Erskine, Japanese Application No. P2008-500802, Office Action dated Jun. 29, 2010, 6 pages.
Erskine, Malaysia Application No. PI 20071468, Substantive Examination Report dated Apr. 16, 2010, 2 pages.
Patent Cooperation Treaty, PCT/US06/07910, PCT International Preliminary Report on Patentability, dated Jul. 3, 2007, 20 pages.
Patent Cooperation Treaty, PCT/US06/07909, PCT International Search Report and Written Opinion, dated Jun. 26, 2006, 8 pages.
Erskine, Taiwanese Application No. 095107593, Decision to Grant Patent dated Dec. 11, 2009, 5 pages.
Patent Cooperation Treaty, PCT/US09/036197, PCT International Search Report and Written Opinion dated Apr. 28, 2009, 14 pages.
Patent Cooperation Treaty, PCT/US09/038246, PCT International Search Report and Written Opinion dated May 20, 2009, 11 pages.
Erskine, U.S. Appl. No. 11/817,891, Office Communication dated Oct. 19, 2009, 10 pages.
Erskine, Australian Application No. 2006220690, Examiner's First Report on Patent dated Nov. 11, 2008, 3 pages.
Erskine, Chinese Application No. 200680007590, Office Action (Translation) dated Aug. 21, 2009, 11 pages.
Erskine, European Application No. EP06737126, Supplementary European Search Report dated Feb. 11, 2010, 4 pages.
Patent Cooperation Treaty, PCT/US06/07910, PCT International Search Report and Written Opinion, dated Jul. 5, 2006, 8 pages.
Matney, Office Action Communication for U.S. Appl. No. 13/254,163 dated Oct. 15, 2013, 81 pages.
Omgba, Office Action Communication for U.S. Appl. No. 13/114,589 dated Oct. 31, 2013, 19 pages.
Patent Cooperation Treaty, Preliminary Report on Patentability and Written Opinion of the International Searching Authority for PCT/US2012/032578 dated Oct. 8, 2013, 10 pages.
Flick: U.S. Appl. No. 13/259,715, filed Dec. 2, 2011, Office Action Dec. 17, 2012, 42pgs.
Omgba, Office Action Communication for U.S. Appl. No. 13/114,589 dated Sep. 14, 2012, 39 pages.
Extended European Search Report for EP Application No. 11845646.6, dated Nov. 25, 2015, 10 pages.
Extended European Search Report for EP Application No. 11845959.3, dated Nov. 25, 2015, 9 pages.
Notice of Allowance and Fee(s) Due for U.S. Appl. No. 13/997,969, dated Dec. 23, 2015, 16 pages.
Fourth Office Action for CN Patent Application No. 201180066325.4, dated Feb. 2, 2016, 6 pages.
Preliminary Notice of Rejection for JP application No. 2014-504040, dated Mar. 22, 2016, 7 pages.

\* cited by examiner

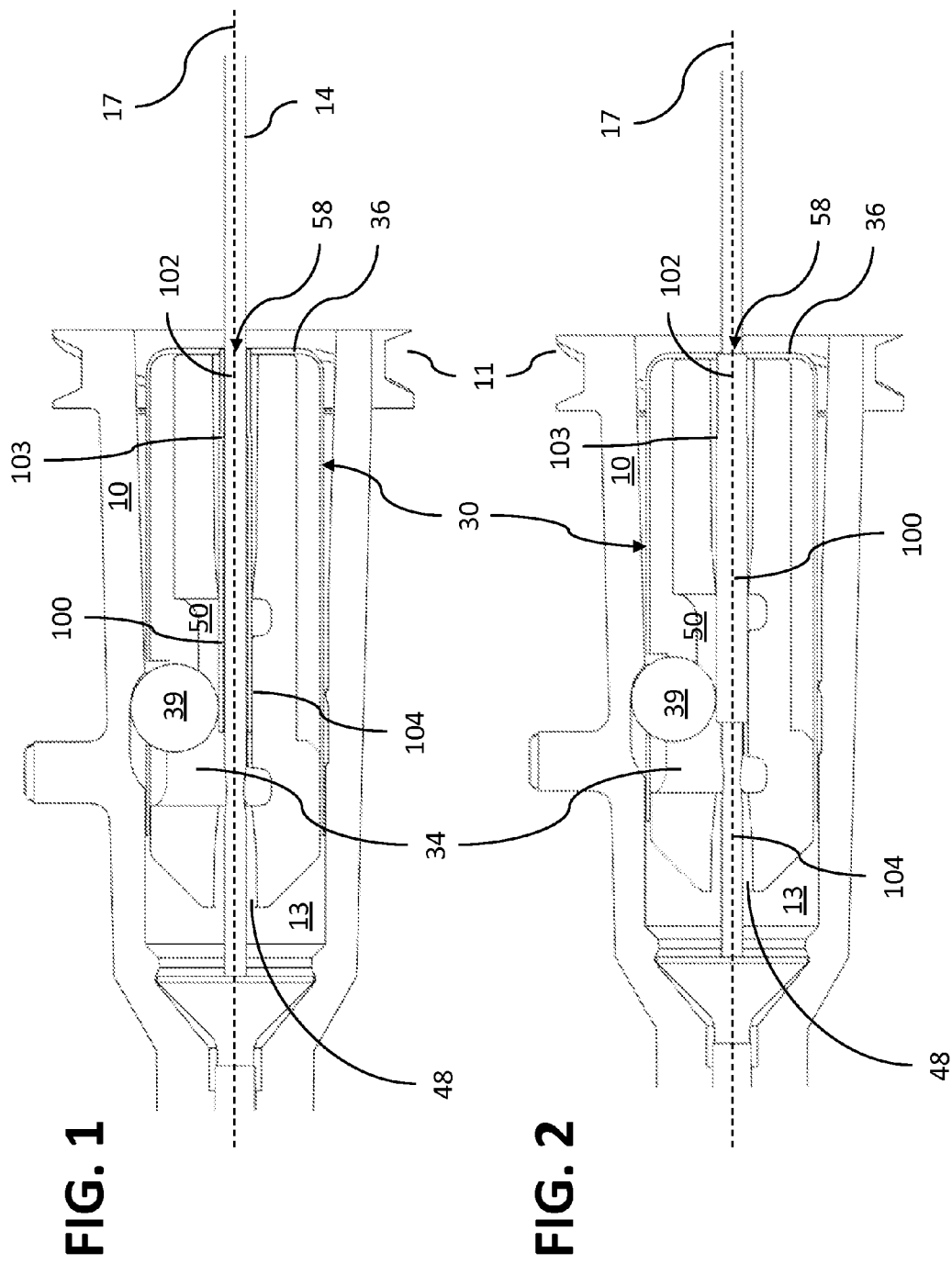

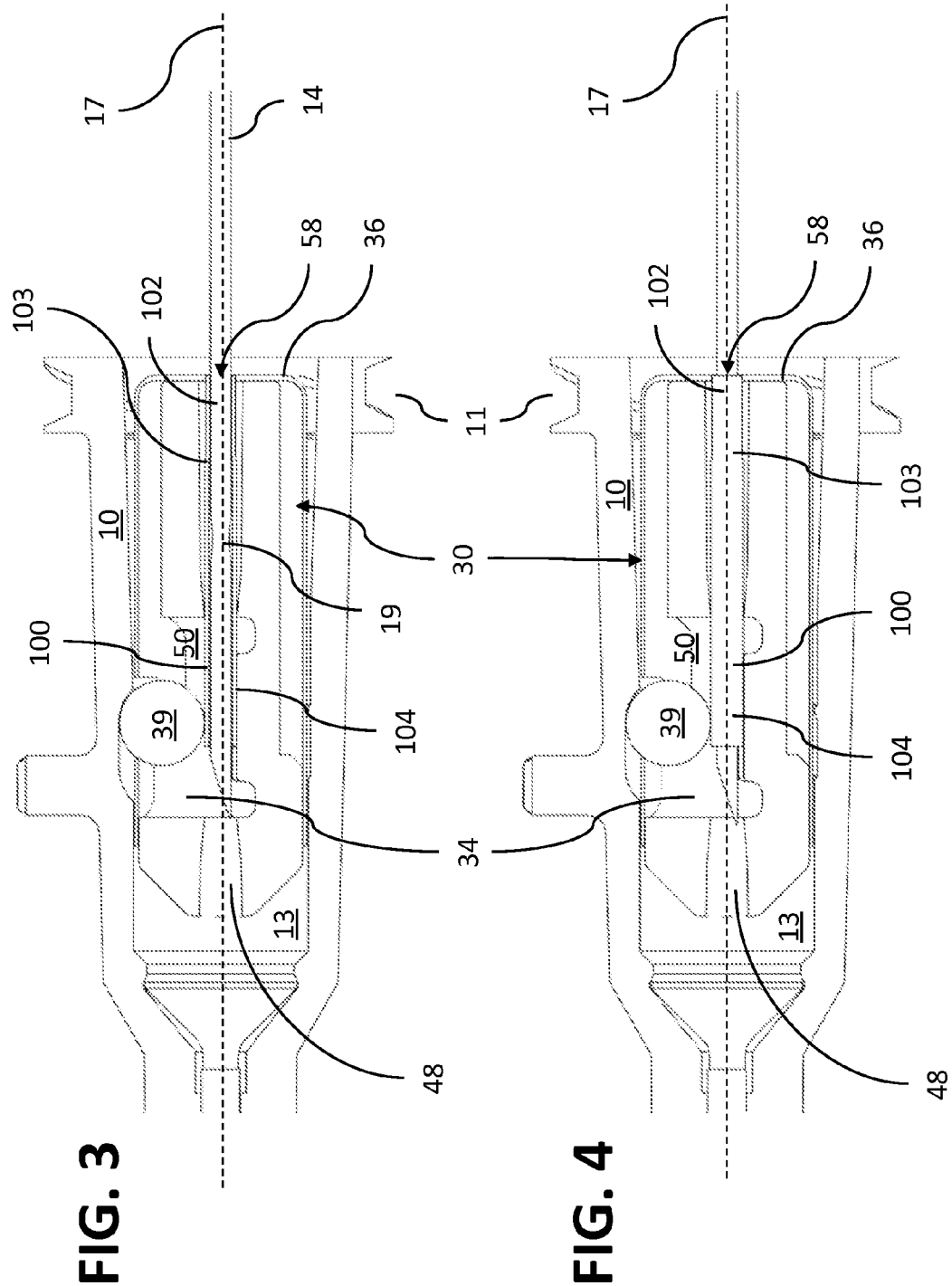

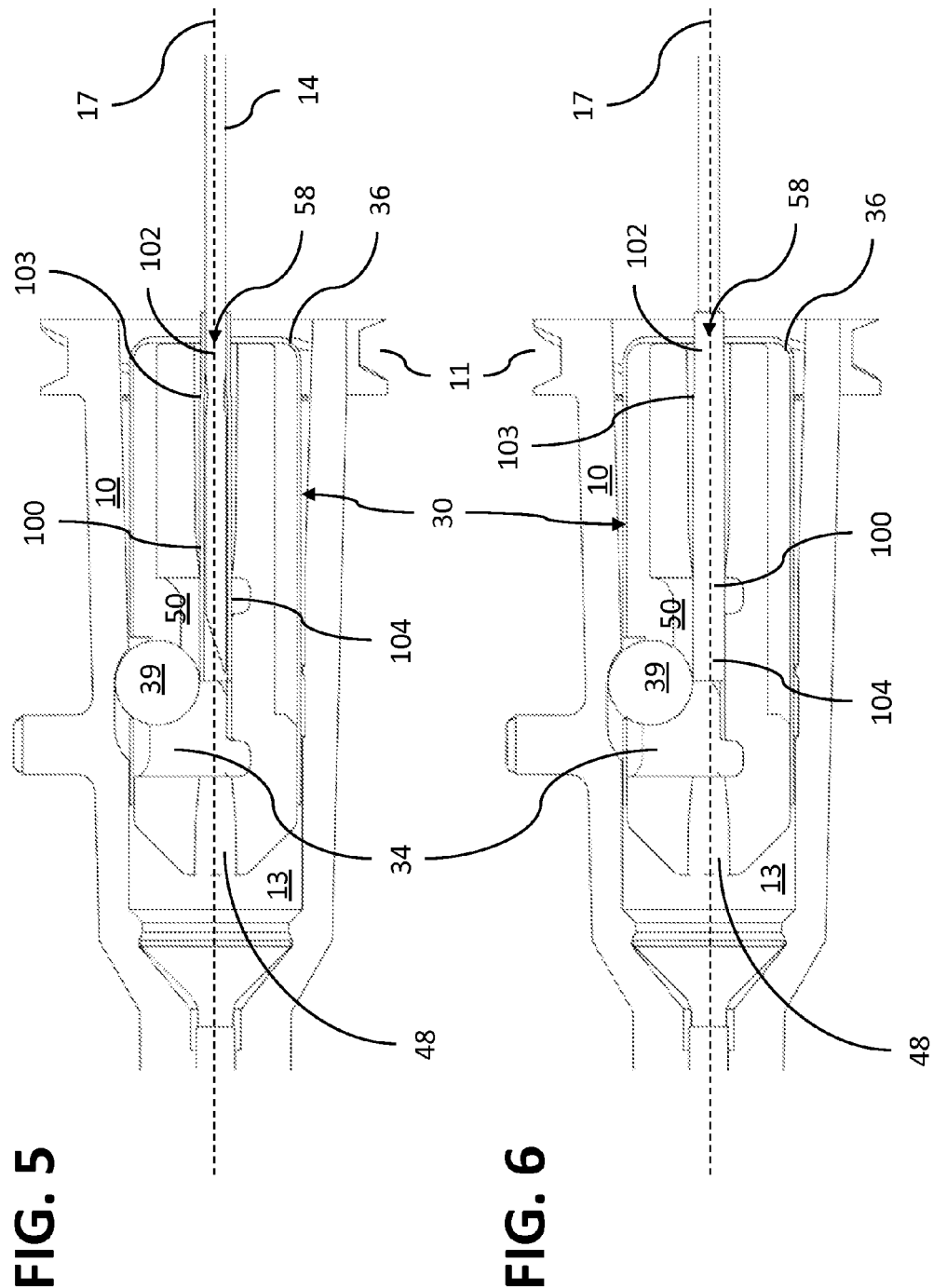

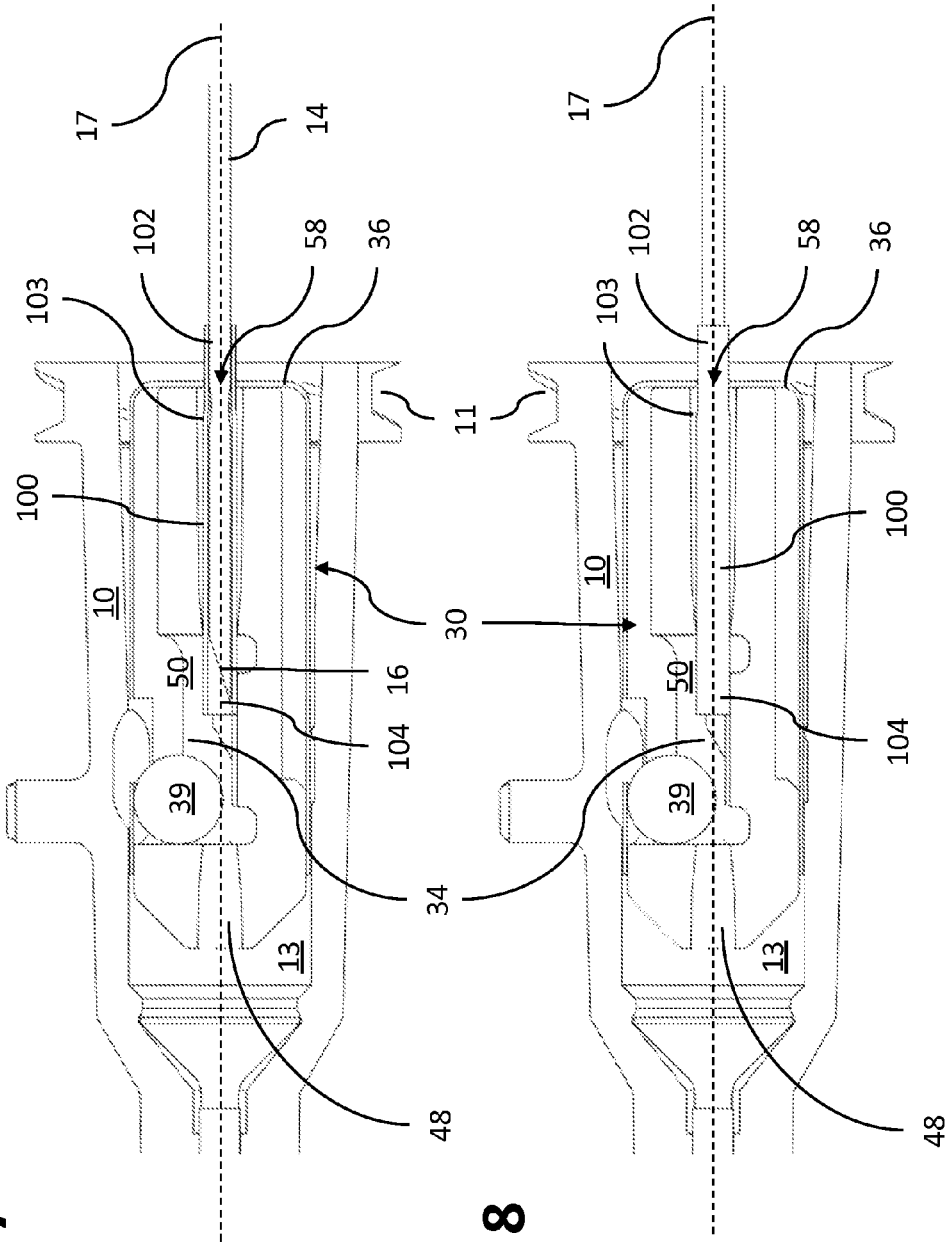

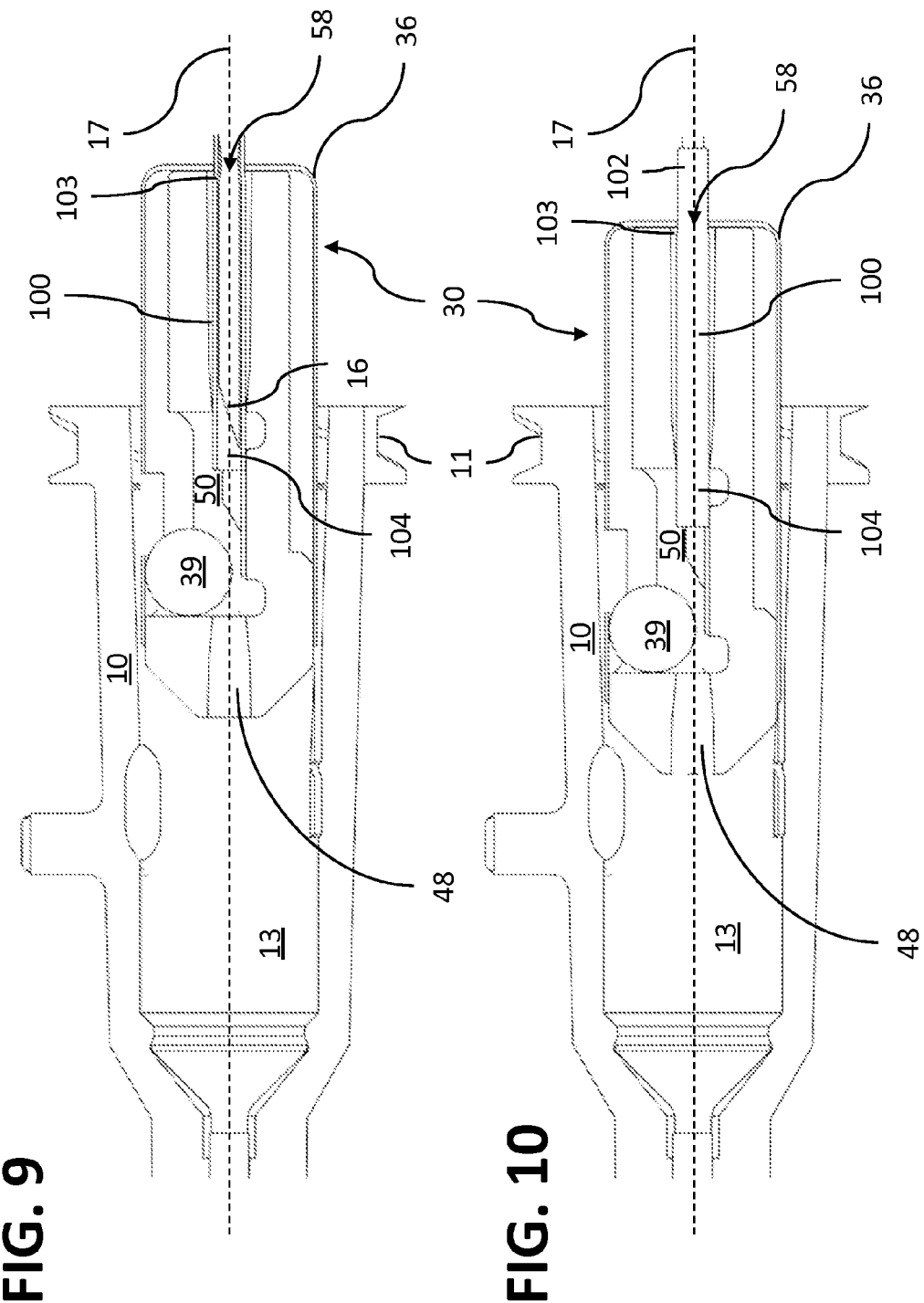

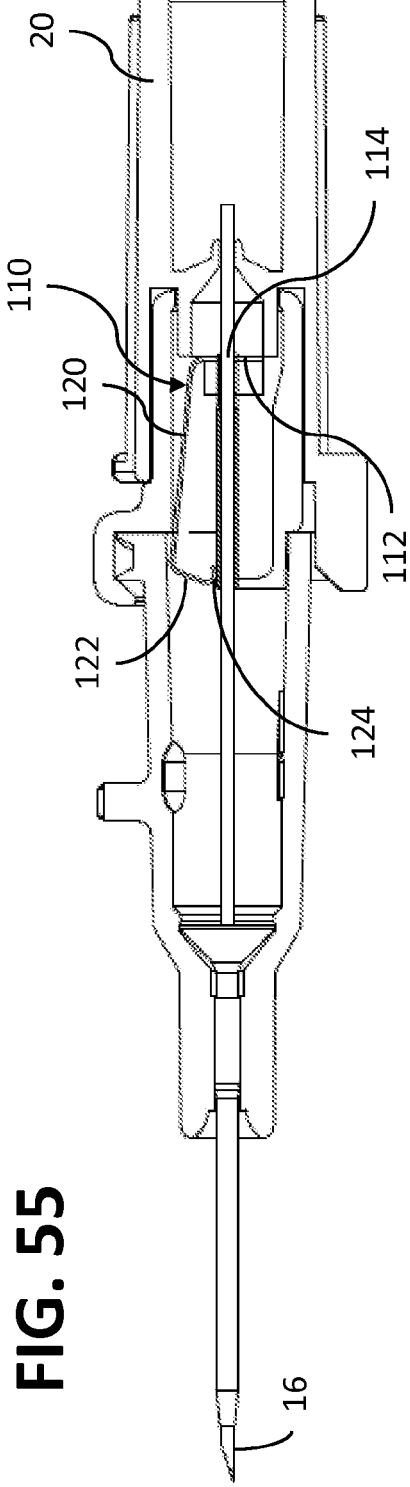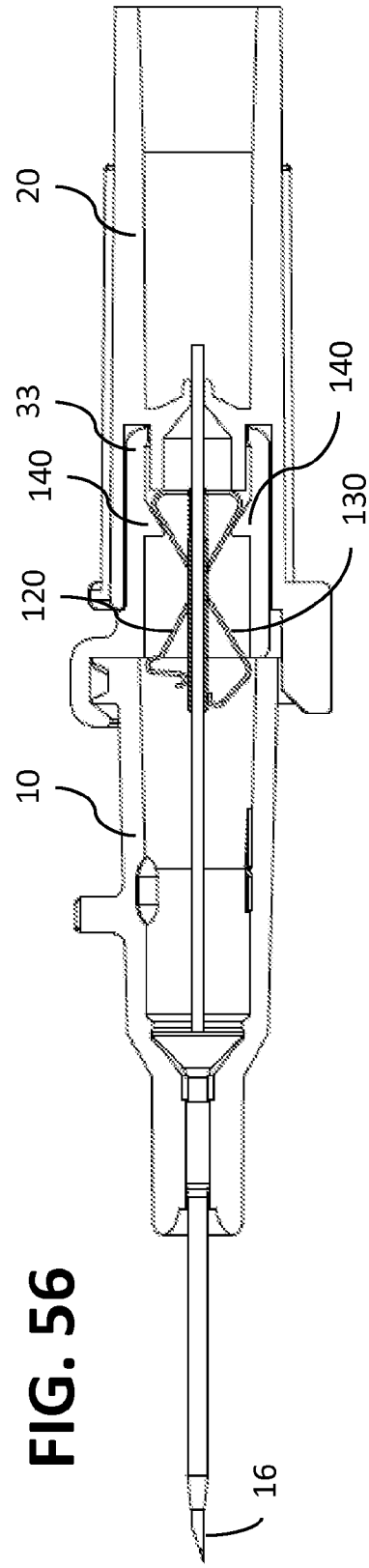

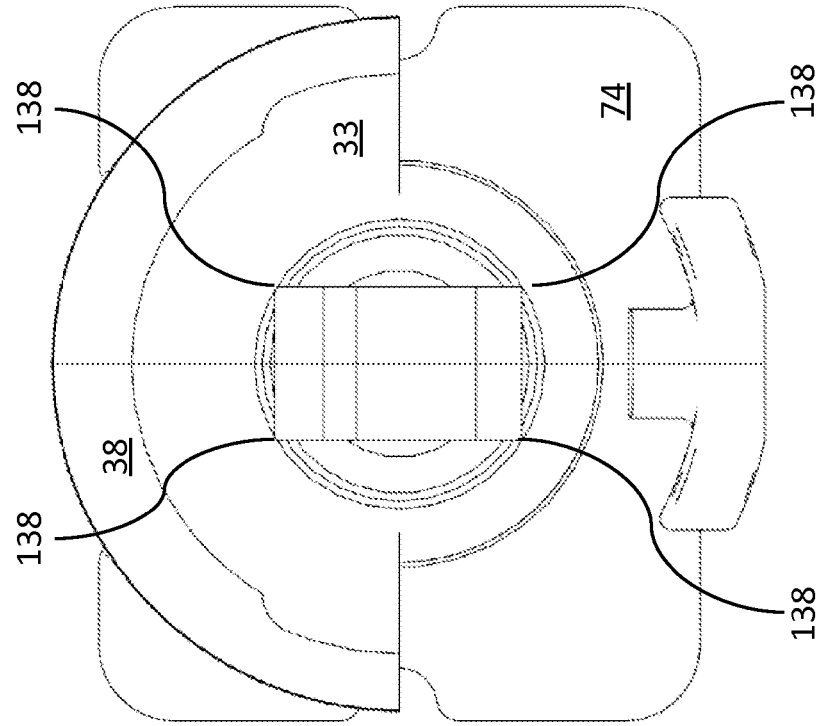
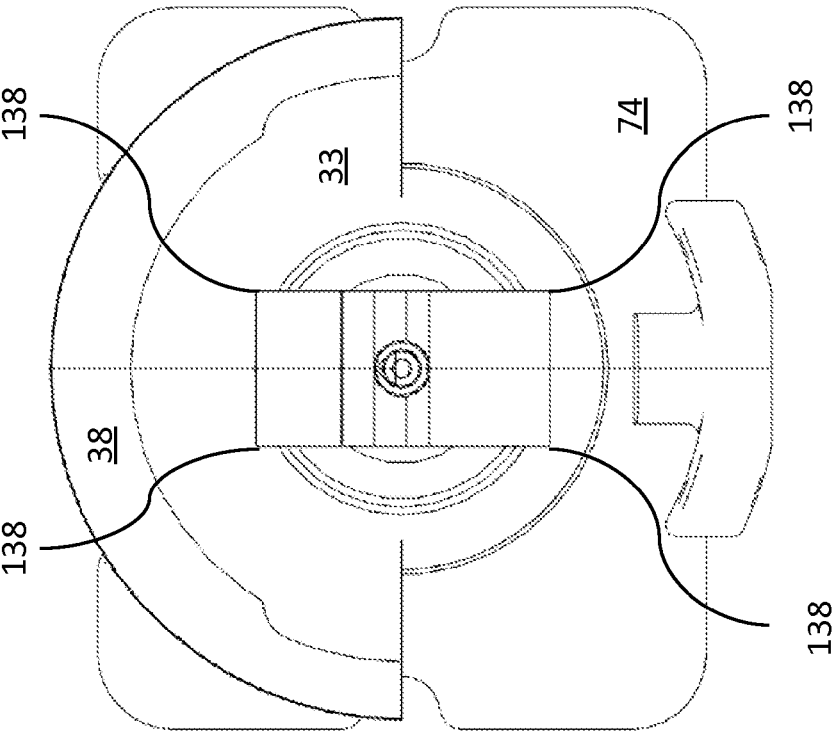

NEEDLE SHIELDING DEVICE

CROSS REFERENCE TO RELATED APPLICATION

This patent application claims the benefit of U.S. Provisional Patent Application Ser. No. 61/472,881, filed Apr. 7, 2011.

BACKGROUND OF THE INVENTION

The invention relates generally to needle-based medical devices. More particularly, the invention relates to a passive safety shield for a needle of a needle-based medical device which shields the needle prior to releasing from a device. Needle shielding devices come in a variety of forms that do not allow for easy and passive activation and disconnection from a hub, such as a catheter introducer hub. Furthermore, needle shielding devices typically protrude into the catheter introducer hub and occupy the volume of the female luer connector, thereby interfering with hemostatic valves and seals.

BRIEF DESCRIPTION OF THE INVENTION

A first aspect of the disclosure provides a needle device comprising: a needle having a longitudinal axis, a proximal end, and a sharp distal tip; a bushing disposed about the needle, wherein the bushing has an inner surface and an outer surface; and a needle blocker, wherein in a non-shielding position, the needle blocker is biased radially inward against the outer surface of the bushing, and wherein in a shielding position, the sharp distal tip is positioned within the bushing, and at least a portion of the needle blocker extends over a distal end of the bushing, blocking distal movement of the sharp distal tip of the needle.

A second aspect of the disclosure provides a needle device comprising: a hub having an engaging member on an exterior thereof; a needle having a longitudinal axis, a proximal end, and a sharp distal tip; a latch including a housing and a latch member; and a clip needle guard movable between a non-shielding position and a shielding position, wherein the clip needle guard includes: a first axially extending arm, wherein the first axially extending arm includes a radially extending member on a distal end thereof, wherein in the non-shielding position, the latch member engages the engaging member on the exterior of the hub, and wherein in the shielding position, the radially extending member blocks distal movement of the sharp distal tip of the needle.

A third aspect of the disclosure provides a needle having a longitudinal axis, a proximal end, and a sharp distal tip; a bushing disposed about the needle, wherein the bushing has an inner surface and an outer surface; a needle shield assembly associated with the needle and moveable from a non-shielding position to a shielding position in which the sharp distal tip is covered by at least part of the needle shield assembly; a needle blocker, wherein in the non-shielding position, the needle blocker is biased radially inward against the outer surface of the bushing; a hub having an engaging member on an exterior side thereof; and a latch associated with the needle shield assembly, wherein in the non-shielding position, the latch engages the engaging member on the exterior of the hub, wherein the latch includes a housing and a latch member, and wherein in the shielding position, the sharp distal tip is positioned within the bushing, and at least a portion of the needle blocker extends over a distal end of the bushing, blocking distal movement of the sharp distal tip of the needle.

A fourth aspect of the disclosure provides a needle device comprising: a needle having a longitudinal axis, a proximal end, and a sharp distal tip; a bushing disposed about the needle, wherein the bushing has an inner surface and an outer surface; a needle shield assembly associated with the needle and moveable from a non-shielding position to a shielding position in which the sharp distal tip is covered by at least part of the needle shield assembly, the needle shield assembly including: a needle blocker; a carrier for carrying the needle blocker; and a spring for biasing the needle blocker distally and toward the longitudinal axis, wherein in the non-shielding position, the spring biases the needle blocker radially inward against the outer surface of the bushing, and wherein in the shielding position, the sharp distal tip is positioned within the bushing, and at least a portion of the needle blocker extends over a distal end of the bushing, blocking distal movement of the sharp distal tip of the needle.

A fifth aspect of the disclosure provides a needle device comprising: a hub having an engaging member on an exterior side thereof; a needle having a longitudinal axis, a proximal end and a sharp distal tip; a bushing disposed about the needle, wherein the bushing has an inner surface and an outer surface; a needle shield assembly associated with the needle and moveable from a non-shielding position to a shielding position in which the sharp distal tip is covered by at least part of the needle shield assembly, the needle shield assembly including: a needle blocker; a carrier for carrying the needle blocker; a spring for biasing the needle blocker distally and toward the longitudinal axis; and a latch including a housing and a latch member; wherein in the non-shielding position, the spring biases the needle blocker radially inward against the outer surface of the bushing, and the latch engages the engaging member on the exterior of the hub, and wherein in the shielding position, the sharp distal tip is positioned within the bushing, and at least a portion of the needle blocker extends over a distal end of the bushing, blocking distal movement of the sharp distal tip of the needle.

A sixth aspect of the disclosure provides a needle device comprising: a hub having an engaging member on an exterior thereof; a needle having a longitudinal axis, a proximal end, and a sharp distal tip; a bushing disposed about the needle, wherein the bushing has an inner surface and an outer surface; a latch including a housing and a latch member; and a clip needle guard movable between a non-shielding position and a shielding position, wherein the clip needle guard includes: a first axially extending arm, wherein the first axially extending arm includes a radially extending member on a distal end thereof, wherein in the non-shielding position, the latch member engages the engaging member on the exterior of the hub, and the radially extending distal member is biased against the outer surface of the bushing, and wherein in the shielding position, the sharp distal tip is positioned within the bushing, and at least a portion of the radially extending member extends over a distal end of the bushing, blocking distal movement of the sharp distal tip of the needle.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

FIGS. 1-10 show cross sectional views of a needle device including a needle shield according to one embodiment of the invention, in a progression from a non-shielding position (FIGS. 1-4) through a transitional position (FIGS. 5-6), to a shielding position (FIGS. 7-10).

FIG. 31 shows a detailed view of a portion of FIG. 30.

FIGS. 55-56 show cross sectional views of a needle device including a needle shield assembly in a non-shielding position according to embodiments of the invention.

FIGS. 57-58 show cross sectional views of a needle device including a needle shield assembly in a non-shielding position according to embodiments of the invention.

Figure 11:
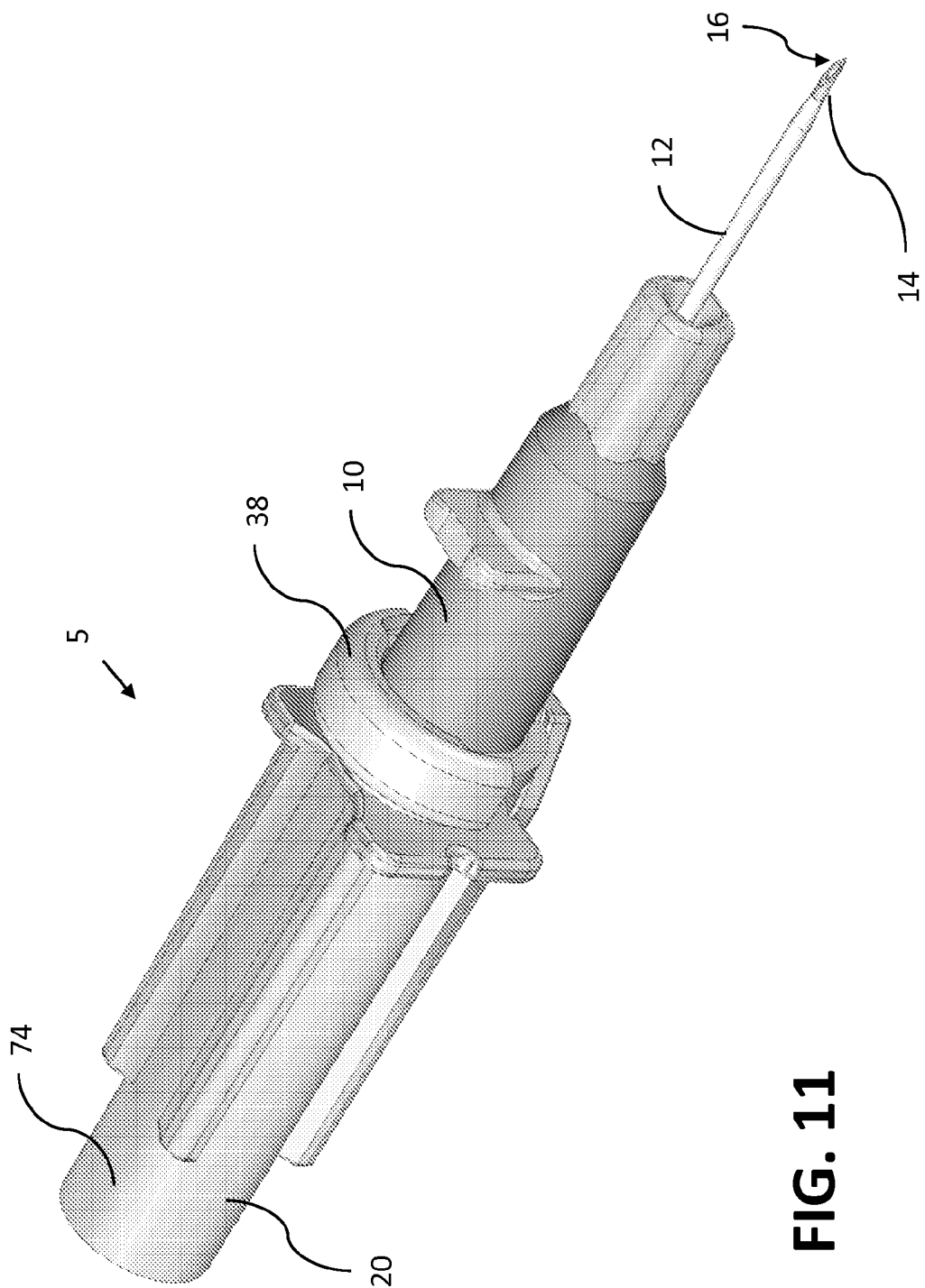
FIG. 11 shows a perspective view of a needle device including a needle shield assembly in a non-shielding position according to embodiments of the invention.
Figure 12:
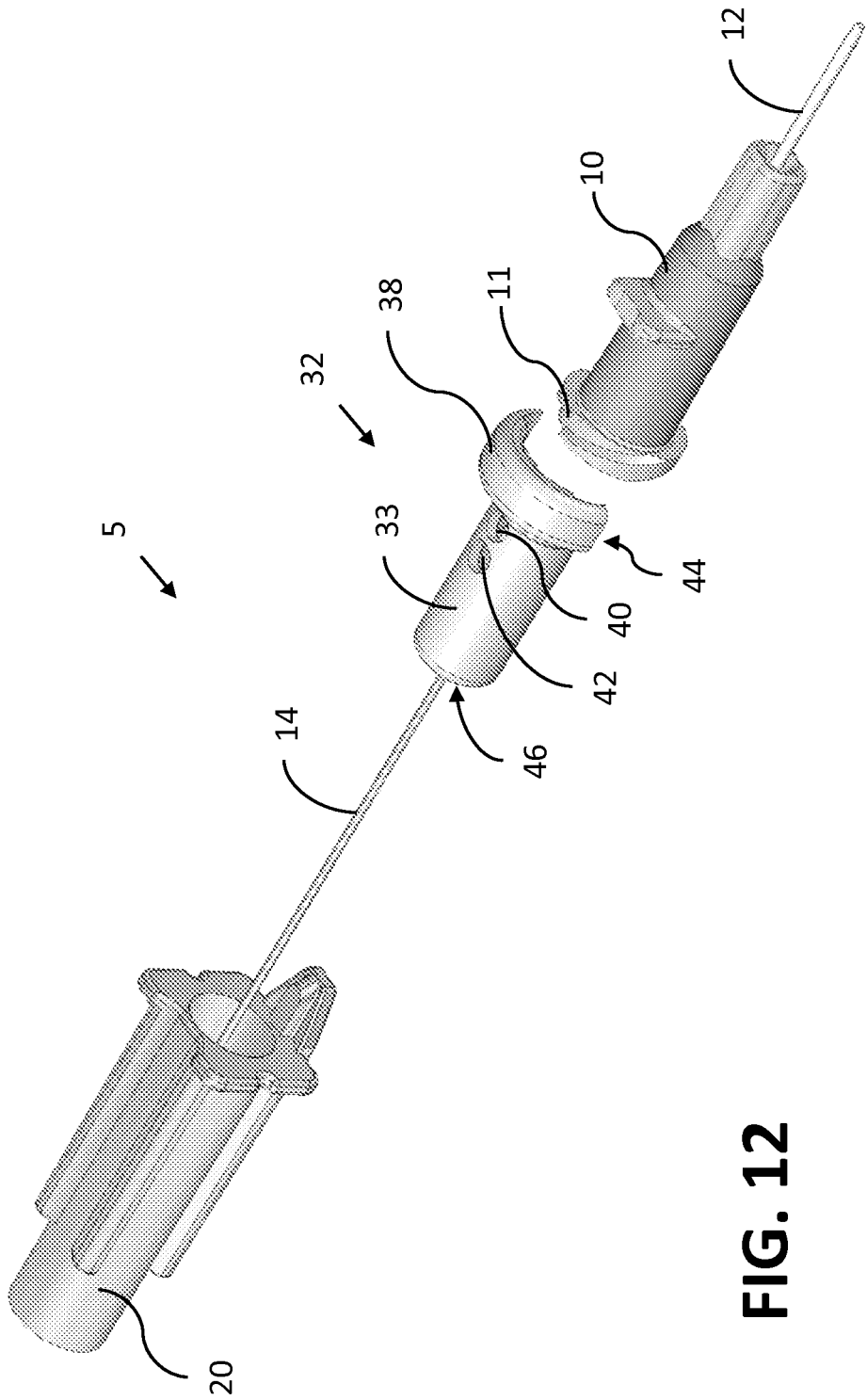
FIG. 12 shows an exploded perspective view of a needle device including a needle shield assembly according to embodiments of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

Figure 54:
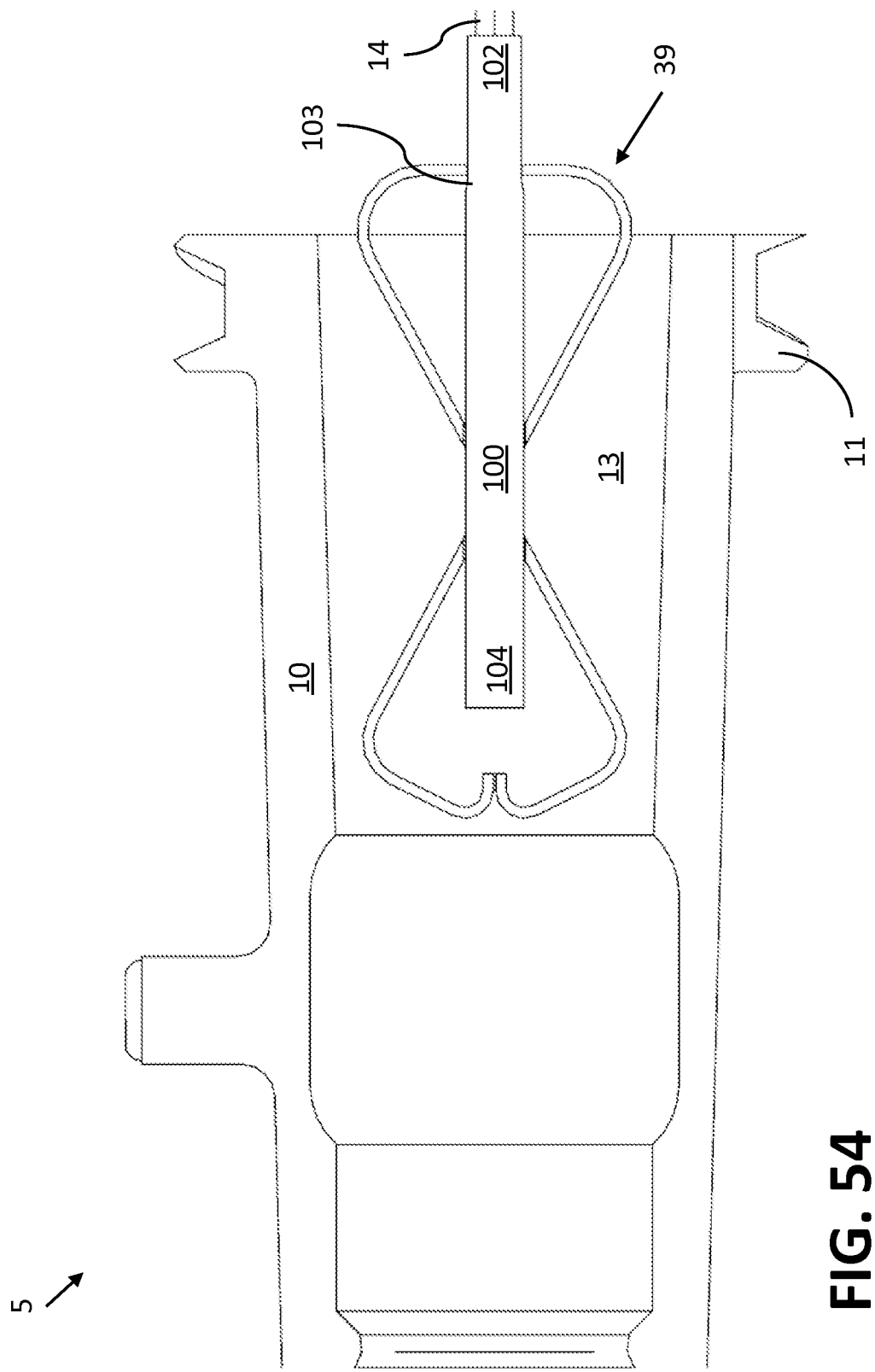

As noted, a needle-based medical device including a needle shield will be described with reference to FIGS. 1-54. At least one embodiment of the present invention may be described below in reference to its application in connection with a needle-based medical device in the form of a catheter introducer. Although embodiments of the invention may be illustrated relative to a catheter introducer, it is understood that the teachings are equally applicable to other needle-based medical devices including, but not limited to, syringes, blood collection devices, and other types of devices. Further, at least one embodiment of the present invention may be described below in reference to a nominal size and including a set of nominal dimensions. However, it should be apparent to those skilled in the art that the present invention is likewise applicable to any suitable needle-based device. Further, it should be apparent to those skilled in the art that the present invention is likewise applicable to various scales of the nominal size and/or nominal dimensions.

With reference to the figures, various embodiments are illustrated including a needle device 5 in the form of a catheter introducer assembly including a hub 10, a catheter cannula 12, and an introducer needle 14.

In the embodiment shown in FIGS. 1-10, hub 10 includes an engaging member 11 on a proximal end thereof. Engaging member 11 may be a threaded, flanged member on a proximal end of hub 10 to which tubing and the like can be connected. Hub 10 also may include a female luer adapter 13 into which a male component such as a blood sealing device 15 (FIGS. 15-20) such as a valve or septum can be placed within hub 10. Although not shown, hub 10 may also include a port. Needle 14 includes a longitudinal axis 17, a sharp distal end 16, and a proximal end 18.

As shown in FIGS. 11-15, proximal end 18 of needle 14 may be secured to a distal end of needle hub 20, e.g., by glue using a glue well, as described in U.S. Pat. No. 8,021,511 and US patent application publication US 2009/0036843A1, each of which are incorporated herein by reference. Needle hub 20 may be secured at its proximal end to a handle 74. Needle 14, hub 10, cannula 12, and needle hub 20 may be substantially coaxial.

Referring to the embodiments depicted in FIGS. 1-25, a needle shield assembly 30 is provided for shielding sharp distal tip 16 of needle 14 following use, as described in co-pending international patent application PCT/US2011/063118, and co-pending US patent application publications US 2008/0119795A1, US 2009/0137958A1, and US 2009/0249605A1. Needle shield assembly 30 includes a needle blocker 39, and a carrier 34 for carrying needle blocker 39.

Needle shield assembly 30 may further include an external shroud 36 disposed about carrier 34, and a spring 41 for biasing needle blocker 39 as described further herein.

Needle shield assembly 30 is movable between a non-shielding position (FIGS. 1-4, 13, 15-16) and a shielding position (FIGS. 7-10, 17-20). FIGS. 1-10 and 15-20 illustrate a progression from the non-shielding position, in which sharp distal tip 16 of needle 14 extends distally beyond needle shield assembly 30, to the shielding position, in which needle shield assembly 30 prevents emergence of sharp distal tip 16 of needle 14 therefrom.

With reference to FIGS. 1-10, needle shield assembly 30 will now be described. Needle shield assembly 30 includes carrier 34, which may be substantially cylindrical and includes an axial lumen 48 substantially aligned with a longitudinal axis 17 of the device. Axial lumen 48 accommodates needle 14 and allows carrier 34 to slide relative to needle 14. Carrier 34 may further include an internal member including a channel 50 or other structure for limiting radial movement of needle blocker 39 toward the longitudinal axis 17 of needle 14 in the shielding position of needle shield assembly 30. In the illustrative embodiment, channel 50 is shaped and dimensioned such that needle blocker 39 can be carried and moved along channel 50 and dropped into place in the shielding position (FIGS. 7-10). In the shielding position, needle blocker 39 lies at least partially across axial lumen 48, thereby blocking emergence of sharp distal end 16 of needle 14.

In further embodiments, shown in FIGS. 13, 15-19, and 22-24, carrier 34 may also include an external shroud 36. Shroud 36 may be made of metal, and may be substantially cup-shaped, such that it substantially encases carrier 34, but is open at the distal end 60. Carrier 34 can thus be inserted into shroud 36 such that a proximal end of the carrier abuts the inside of proximal end 56 of shroud 36. Carrier 34 also includes a first opening 37 through which a portion of needle blocker 39 projects while resting in channel 50 in a non-shielding position. In embodiments including shroud 36, opening 37 extends through a thickness of a wall of shroud 36.

A spring 41 may further be provided for biasing needle blocker 39. Spring 41 may be disposed about carrier 34, and within shroud 36, such that it abuts needle blocker 39. Spring 41 tends to urge needle blocker 39 distally and into lumen 48, toward the longitudinal axis 17 of the device. Spring 41 may be, for example, a coil spring, although other types of springs may be used as known in the art.

Referring to FIGS. 13-20, device 5 may further include a latch 32 for shielding distal tip 16 of needle 14. Carrier 34 and external shroud 36, if present, may be disposed within latch 32 as further described below.

FIGS. 15-20 illustrate one embodiment of progression from the non-shielding position (FIGS. 13, 15-16), in which latch 32 and locking member 54 retain the needle shield assembly 30 in engagement with hub 10, to the shielding position (FIGS. 17-20), in which needle shield assembly 30 prevents emergence of sharp distal end 16 of needle 14 therefrom.

Figure 15:
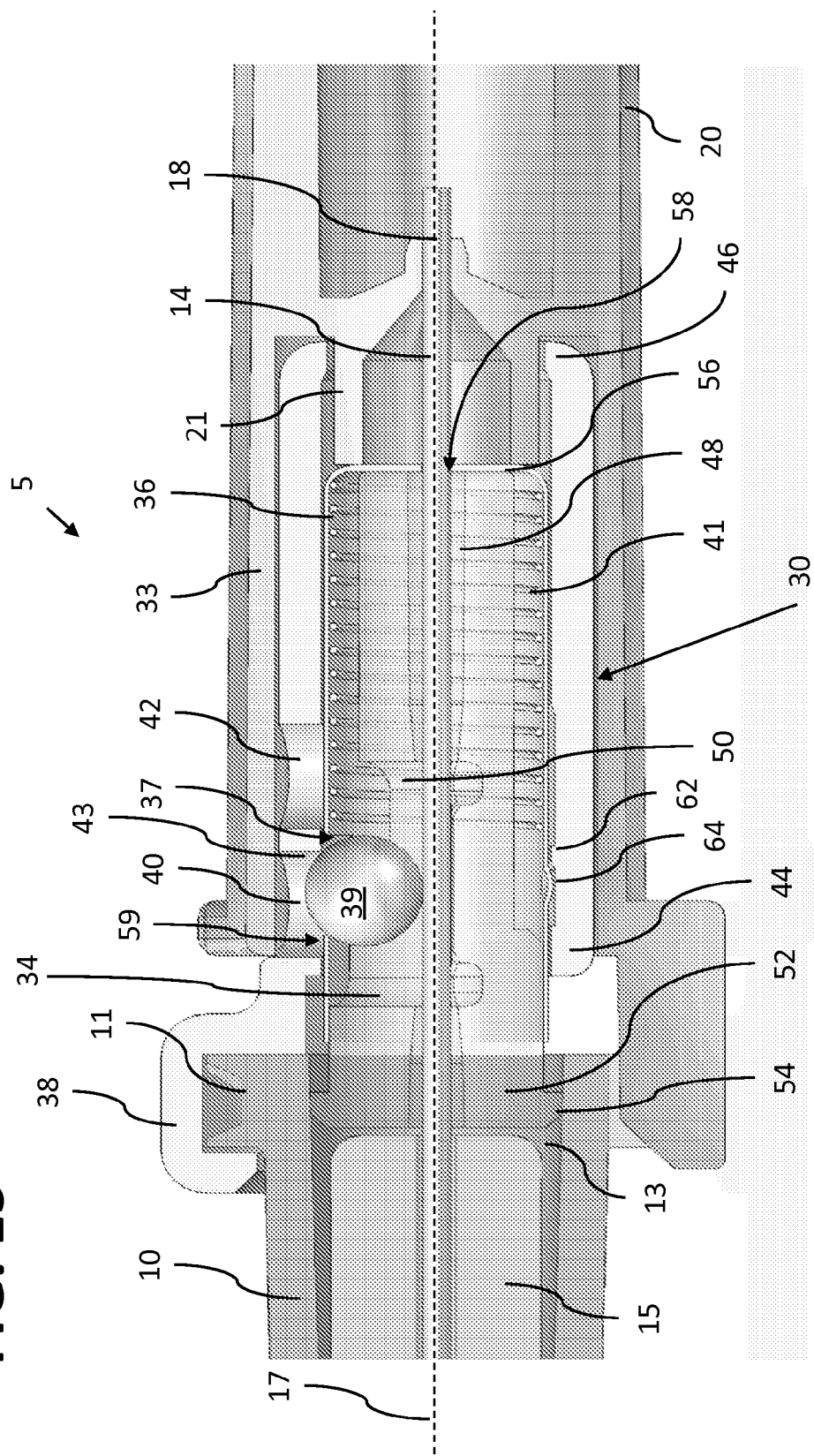
FIG. 15 shows a detailed cross-sectional view of the needle shield assembly and hub in a non-shielding position according to embodiments of the invention.
Figure 16:
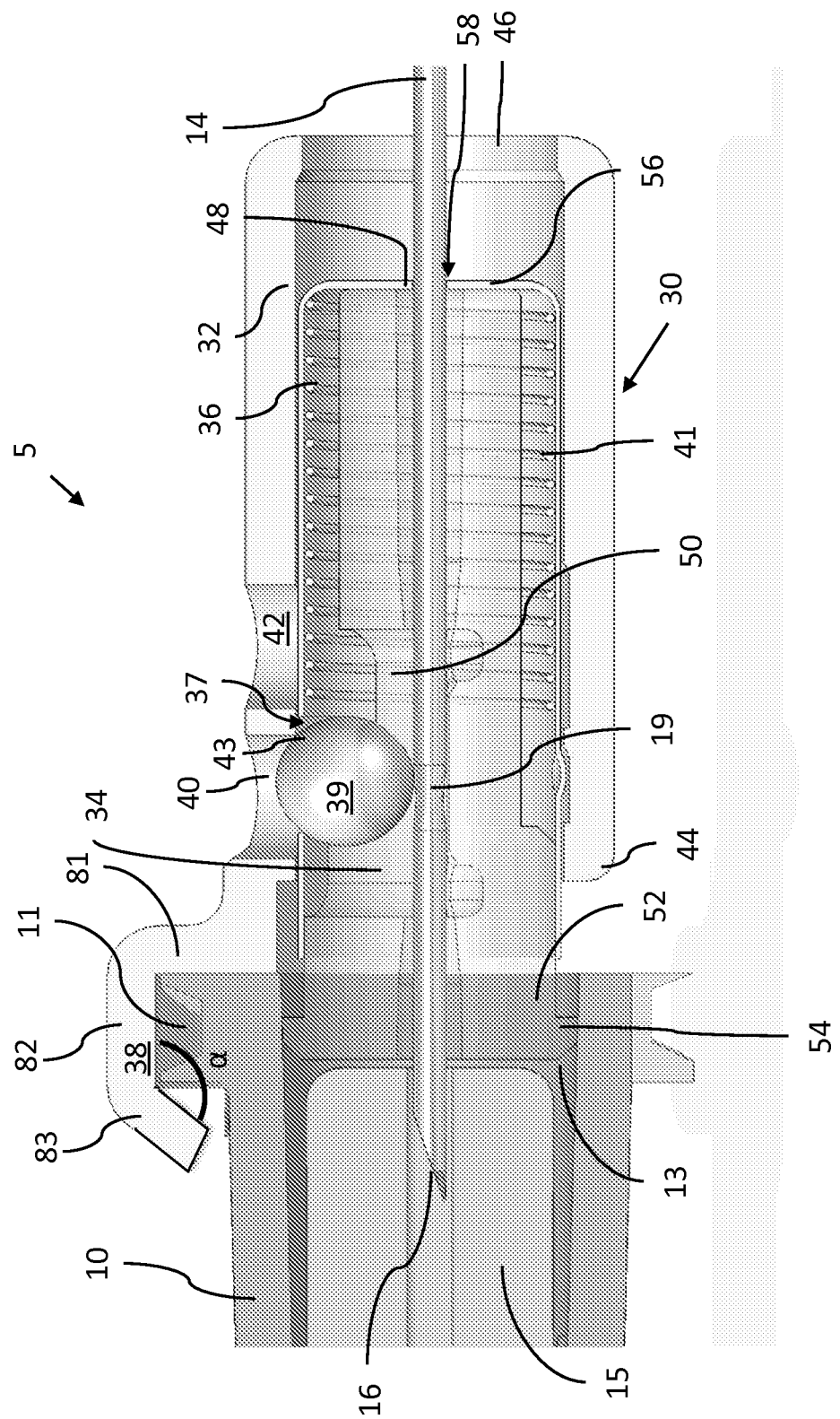
FIGS. 16-19 show detailed cross-sectional views of the needle shield assembly progressing through intermediate positions according to embodiments of the invention.
Figure 17:
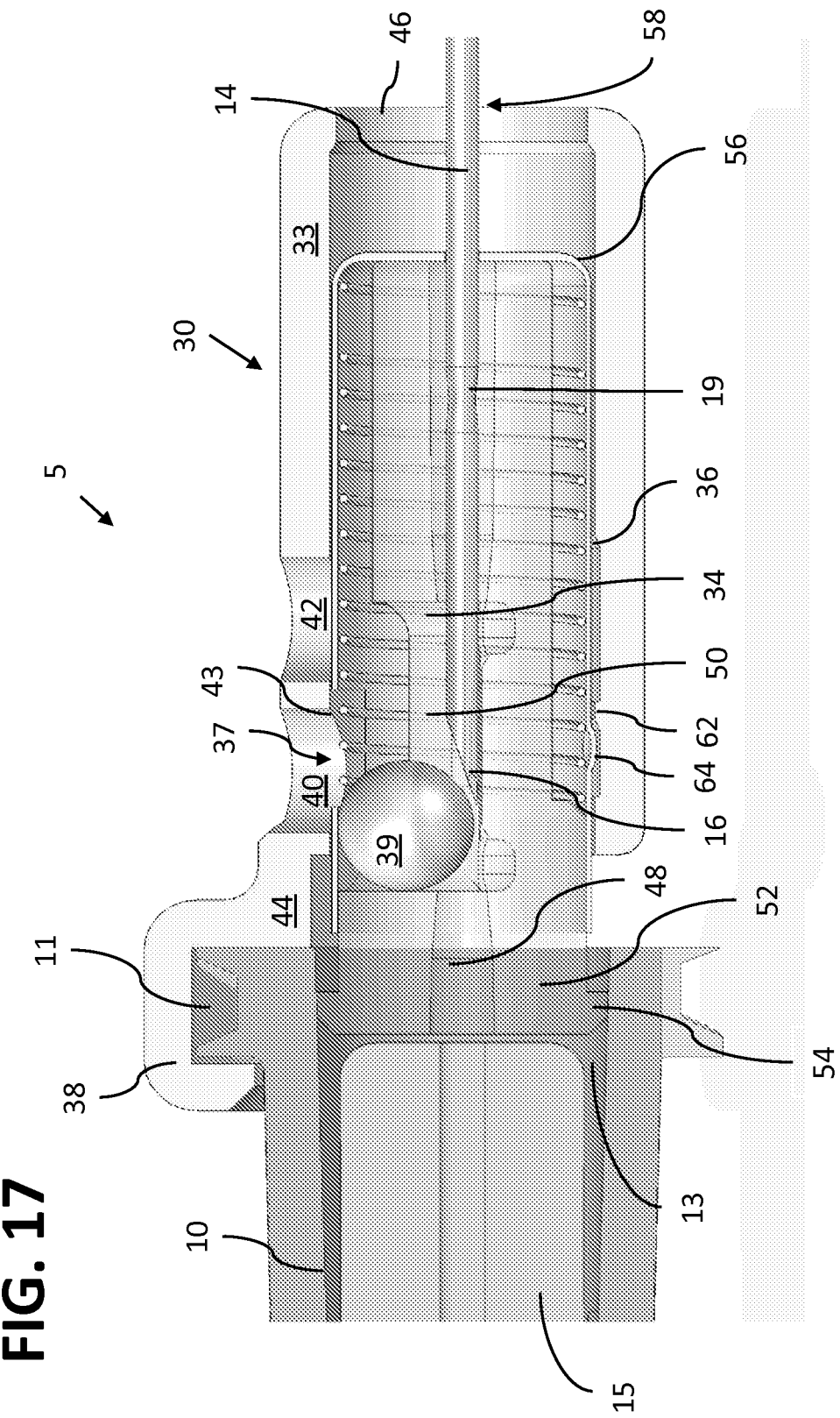

As shown in FIG. 15, a locking member 54 may be operably coupled to a distal end 52 of carrier 34, and is dimensioned to engage an internal surface of hub 10 in the non-shielding position. Locking member 54 may be a flange or flanged member. In some embodiments, the engagement between an internal surface of hub 10 and locking member 54 may include insertion of at least a portion of locking member 54 into hub 10 as shown in FIG. 15. As noted, hub 10 may include a female luer adapter 13, which engages with a close slip fit with locking member 54.

Figure 18:
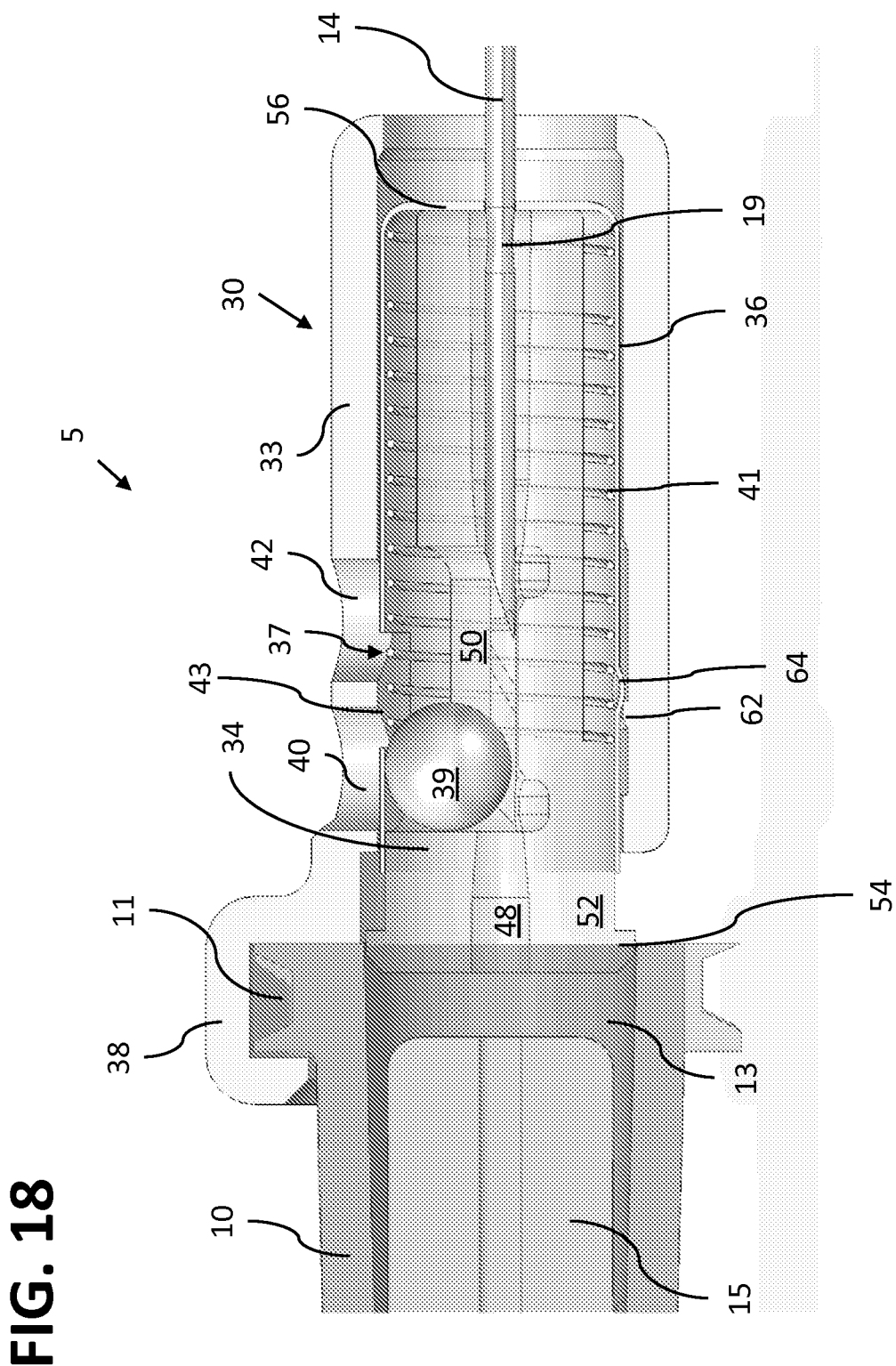

At a proximal end of axial lumen 48, a hole or opening 58 (FIGS. 15-16) may be provided in carrier 34 and shroud 36. Hole 58 is dimensioned to accommodate the outer diameter of needle 14. Needle 14 may include an enlarged diameter portion 19, shown in FIG. 16, which may be in the form of a crimp or other similar shape. Enlarged diameter portion 19 provides an axial portion of needle 14 having an enlarged diameter in at least one radial direction. Opening 58 does not accommodate enlarged diameter portion 19, so that as shown in FIG. 18, enlarged diameter portion 19 provides a stop which engages an inside of proximal end 56 of shroud 36. Enlarged diameter portion 19 is positioned along needle 14 such that when enlarged diameter portion 19 reaches proximal end 56 of shroud 36, sharp distal tip 16 of needle 14 is proximal of needle blocker 39, and therefore shielded.

Referring back to FIG. 15, carrier 34 may be disposed substantially within latch 32, the latter of which engages hub 10 to needle shield assembly 30 in the non-shielding position. Latch 32 includes a housing 33 having a proximal end 46 and a distal end 44, the latter of which is coupled to a hooked latch member 38. Latch member 38 and housing 33 are shown in FIG. 15 as being a single, continuous member, but embodiments in which latch member 38 and housing 33 are separate members that are operably connected are also considered part of the invention.

Figure 13:
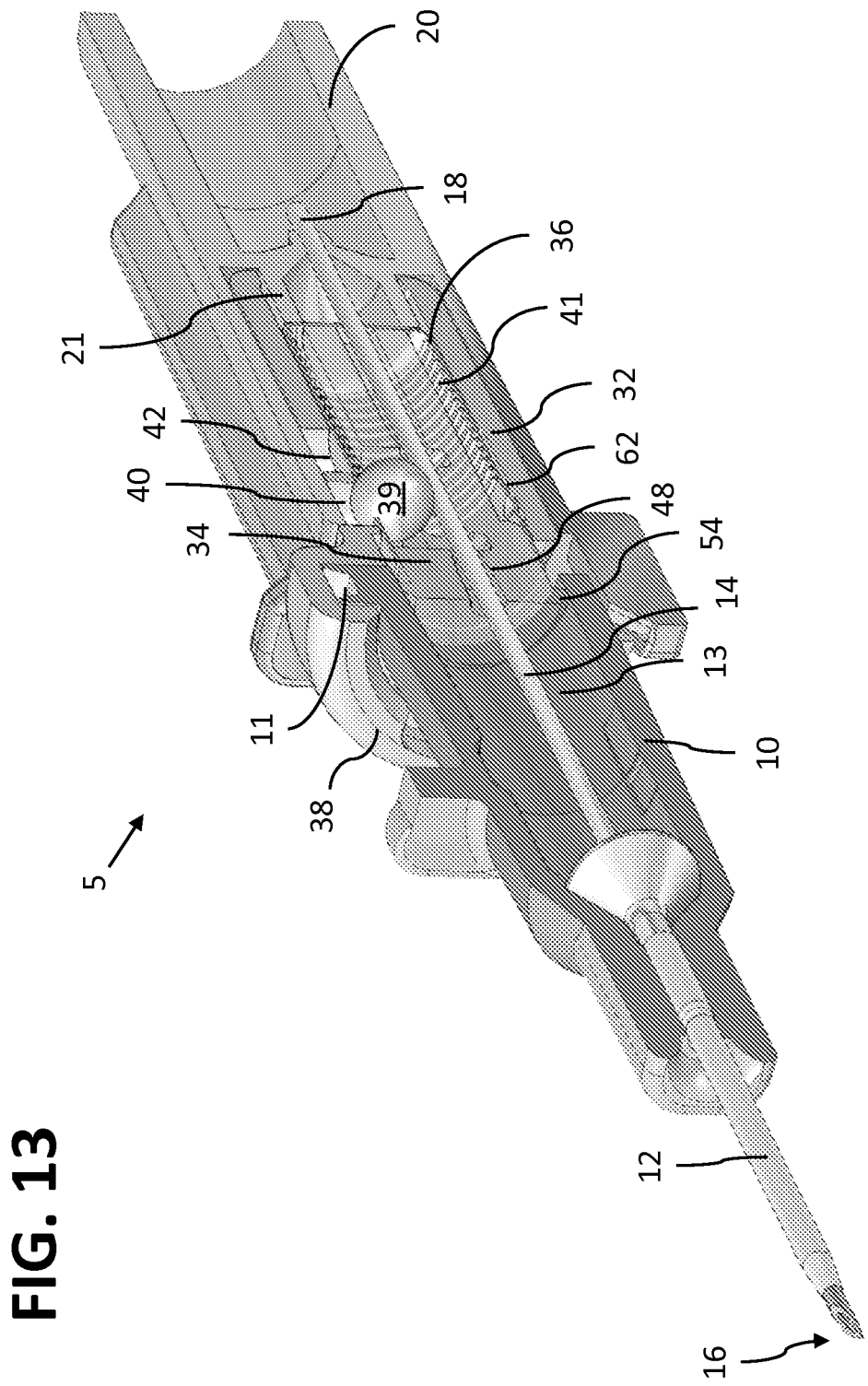
FIG. 13 shows a cutaway perspective view of a needle device including a needle shield assembly in a non-shielding position according to embodiments of the invention.
Figure 14:
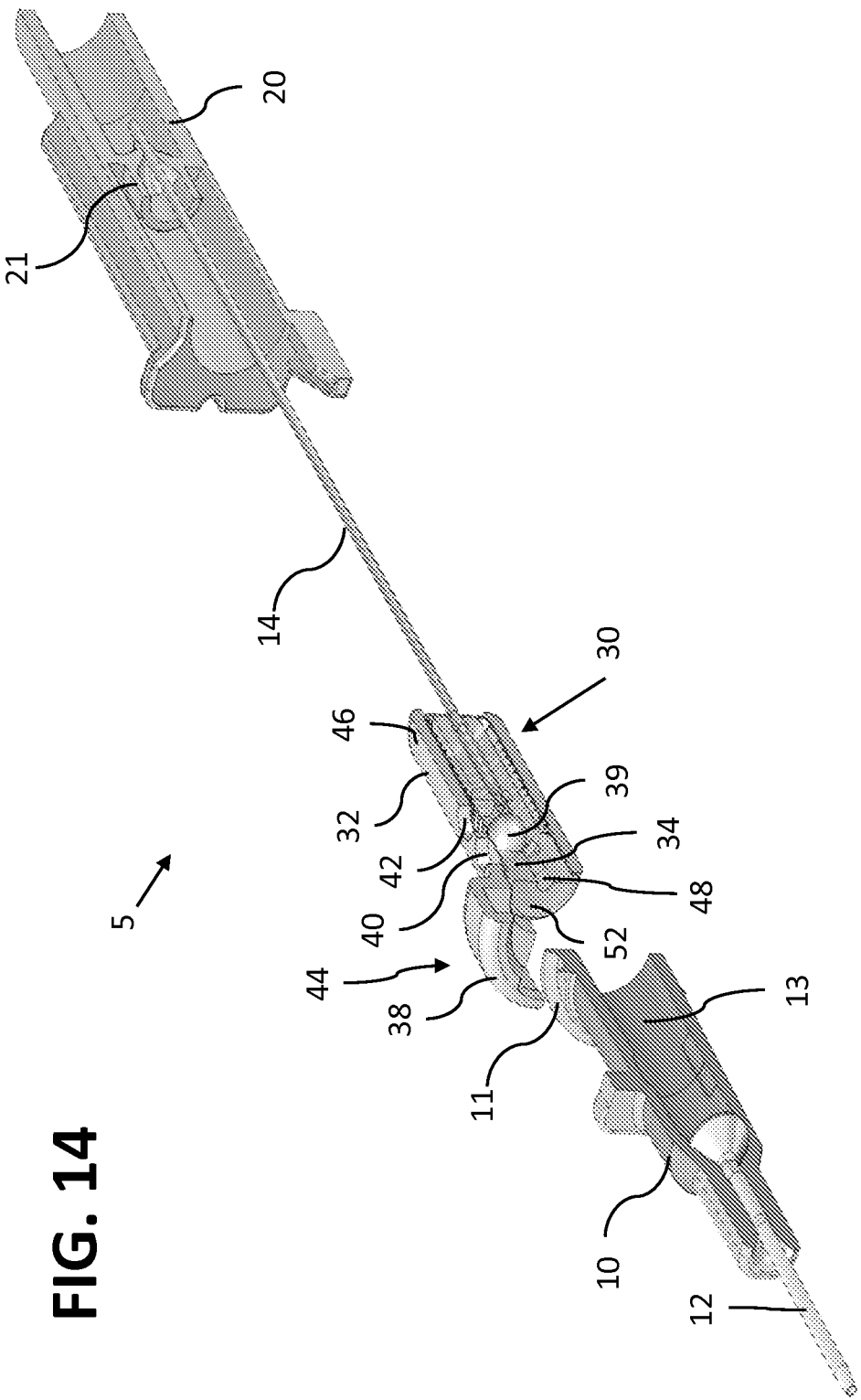
FIG. 14 shows an exploded cutaway perspective view of a needle device including a needle shield assembly in a non-shielding position according to embodiments of the invention.
Figure 22:
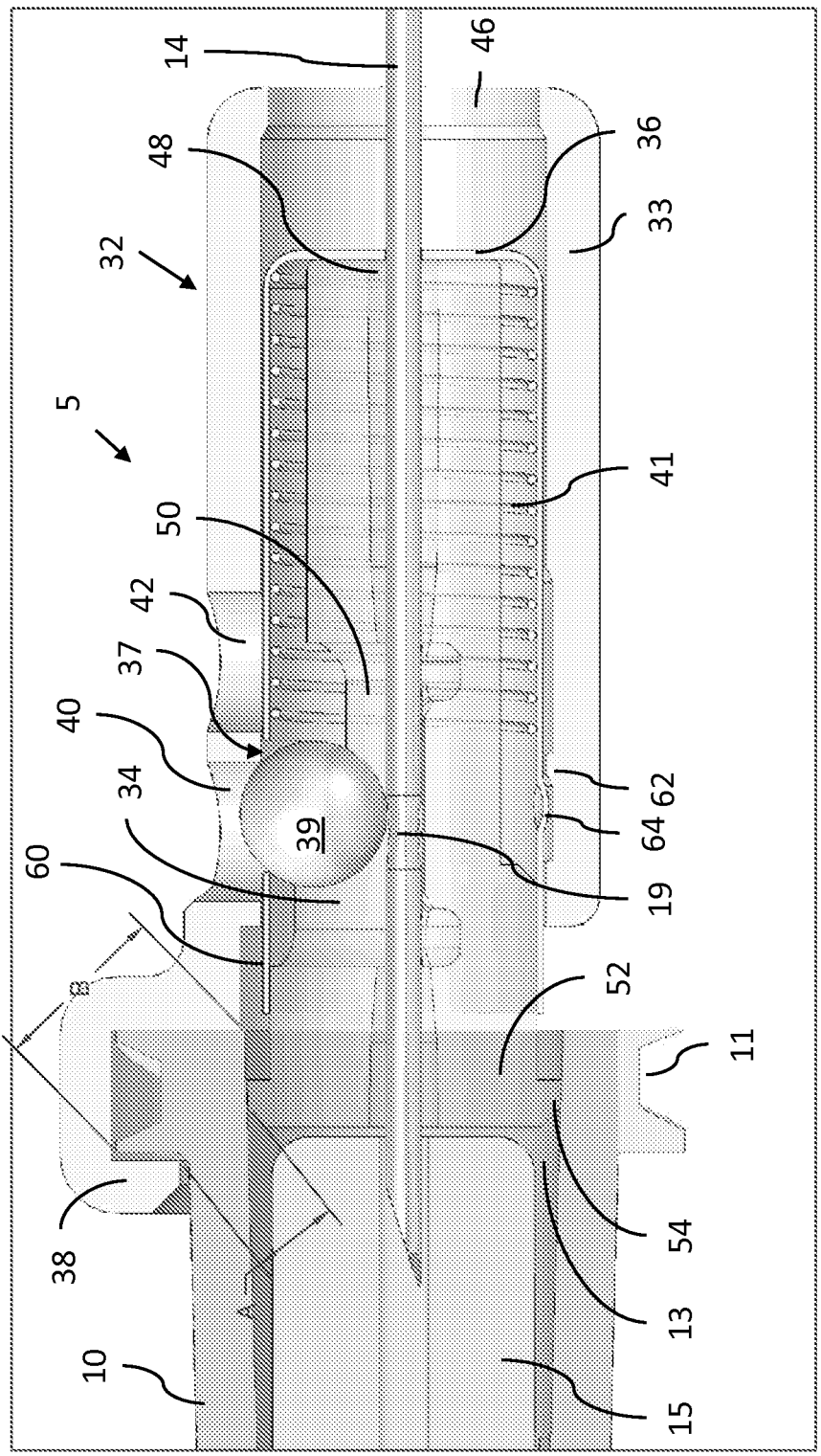
FIG. 22 shows a detailed cross-sectional view of the needle shield assembly in an intermediate non-shielding position according to embodiments of the invention.

Latch member 38 is shaped and dimensioned to engage with engaging member 11 of hub 10. As shown in FIGS. 13 and 22, latch member 38 includes a hooked leg extending over engaging member 11 on hub 10. In one embodiment, hooked latch member 38 includes a first member 81 extending radially outward relative to housing 33, a second member 82 extending distally from a radially outward end of first member 81 in a direction substantially parallel to housing 33, and a third member 83 extending radially inward from the distal end of second member 82, forming a distal restraining surface of latch 32. In the embodiment shown in FIG. 15, second member 82 and third member 83 may be orthogonal. In an alternative embodiment, shown in FIG. 16, the angle α formed by second member 82 and third member 83 may be other than orthogonal, e.g., about 135°, such that third member 83 provides a beveled edge on the distal restraining surface of latch 32 for releaseably engaging flanged engaging member 11 of hub 10. With reference to FIG. 22, in one embodiment, a first distance A between a radially inward end of the leg of latch member 38 and distal end 52 of locking member 54 as positioned within hub 10 is less than a second distance B between a proximal-most point on an internal diameter of hub 10 and a distal-most point on an external diameter of the flange on engaging member 11 of hub 10. The above-described angled structure may be provided to enable smooth disengagement of hook member 38 and flanged engaging member 11.

In some embodiments, engaging member 11 of hub 10 may be threaded. Latch member 38 may have an extent that varies between about 90° and 180° circumferentially (FIG. 14) such that latch 32 can engage hub 10 regardless of its position relative to threads on engaging member 11 of hub 10, and still be able to freely disengage from hub 10 in the shielding position.

Latch 32 further includes a first opening 40 extending through a wall thereof. In the non-shielding position, shown in FIGS. 15-16, opening 37 in external shroud 36 substantially aligns with first opening 40 in latch 32 in the non-shielding position, such that at least a portion of needle blocker 39 protrudes through opening 37 and into first opening 40. The protruding portion of needle blocker 39 engages a proximal edge 43 of first opening 40 in latch 32 to engage locking member 54 with the internal surface of hub 10 and maintain latch 32 in engagement with hub 10.

Figure 19:
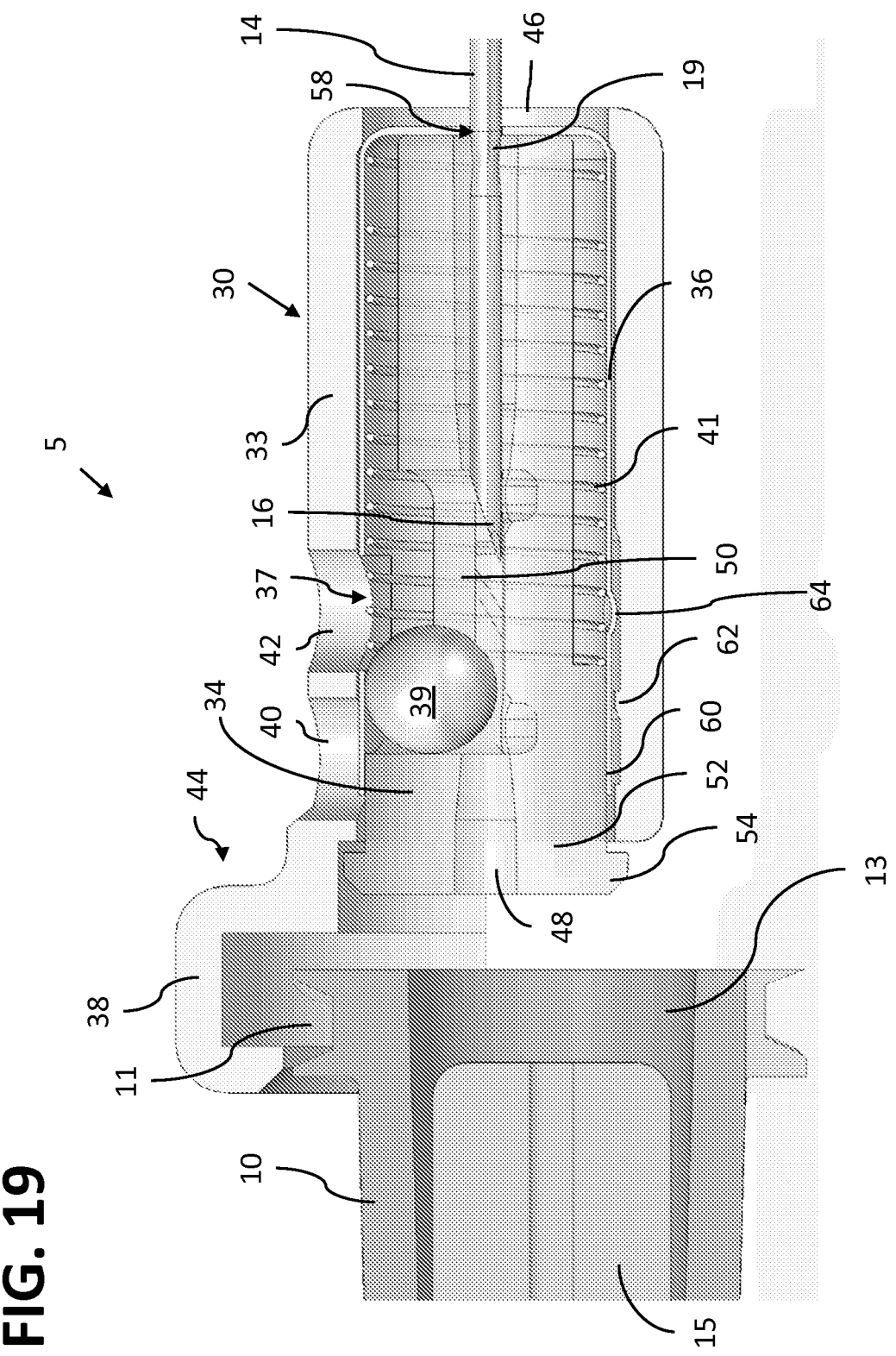
Figure 20:
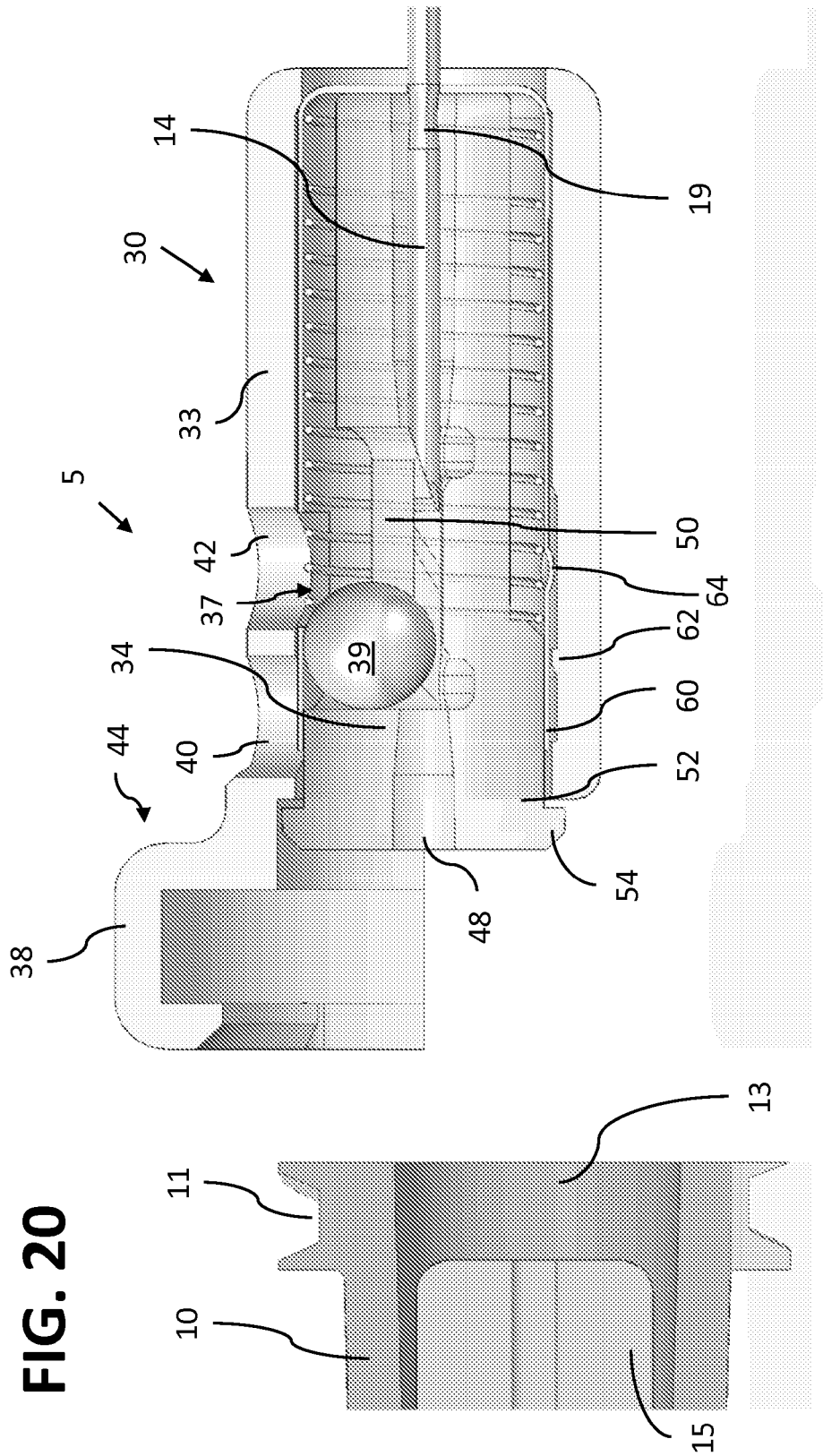
FIG. 20 shows a detailed cross-sectional view of the needle shield assembly in a shielding position according to embodiments of the invention.
Figure 21:
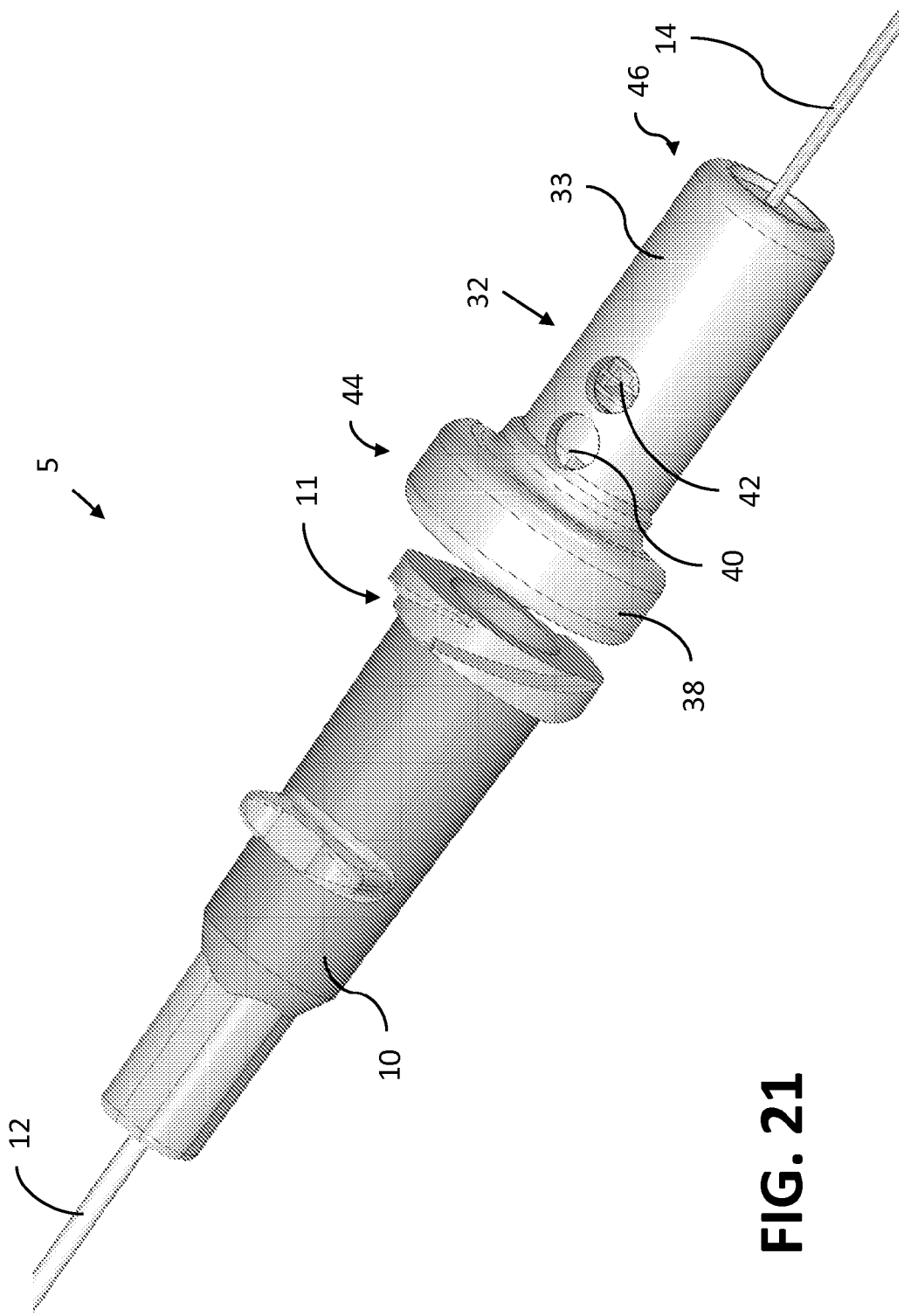
FIG. 21 shows an exploded perspective view of a needle device including a needle shield assembly according to embodiments of the invention.

FIGS. 17-20 illustrate the continued progression of movement from the non-shielding position to the shielding position. Upon movement of the needle shield assembly 30 from the non-shielding position to the shielding position, needle blocker 39 exits first opening 40 in latch 32 and opening 37 in carrier 34. Needle blocker 39 does so under a force from spring 41, which biases needle blocker 39 distally and toward longitudinal axis 17 (FIGS. 1-10, 15) of needle 14. Needle blocker 39 at least partially enters axial lumen 48, preventing emergence of sharp distal end 16 of needle 14 from carrier 34. Locking member 54 disengages from hub 10 and moves proximally within latch 32 (FIG. 18), allowing latch 32 to disengage hub 10 from needle shield assembly 30 (FIGS. 19-20). Latch 32 may further include a second opening 42 through a wall of housing 33. Second opening 42 may be disposed proximally of first opening 40, as shown in FIG. 21.

In further embodiments, as shown in FIGS. 15-20, latch 32 may include a first protrusion 62 on an inner surface of housing 33. A second protrusion 64 may be disposed on an outer surface of carrier 34. Where carrier 34 includes external shroud 36 encasing carrier 34, second protrusion 64 may be on, or part of, an outer surface of external shroud 36. First protrusion 62 interacts with second protrusion 64 as needle shield assembly 30 moves proximally from a non-shielding position to a shielding position such that a pull-out force required to move carrier 34 proximally relative to latch 32 is greater than a frictional force between needle blocker 39 and needle 14. This structure prevents wedging of blocking object 39 and needle 14, as blocking object 39 can roll under proximal edge 43 of opening 40 in latch 32 and wedge against needle 14.

As shown in FIGS. 11-15, needle hub 20 may be disposed about latch 32. Needle 14 is coupled to needle hub 20 such that when needle hub 20 is pulled in a proximal direction, needle 14 moves proximally toward a shielding position. Needle hub 20 may include a boss 21 that abuts proximal end 56 of shroud 36.

When the needle shield assembly is in its fully assembled, non-shielding state (FIGS. 15-16) locking member 54 fits closely into female luer 13 in hub 10. Latch 32, and particularly latch member 38, is hooked over engaging member 11 of hub 10. The fit between latch member 38 and engaging member 11 of hub 10 is loose, such that the pull-off force is low. Needle blocker 39 partially protrudes through opening 37 and into first opening 40 in latch 32. Needle blocker 39 abuts distal edge 59 of opening 37 and proximal edge 43 of opening 40, and is held in place by abutment with the outer surface of needle 14. Locking member 54 cannot escape hub 10 due to needle blocker 39 abutting with proximal edge 43 of first opening 40.

When needle shield assembly 30 is deployed (i.e., needle 14 is withdrawn from hub 10 and carrier 34 moves into the shielding position shown in FIGS. 17-20), the user pulls needle hub 20 in a proximal direction, thus drawing needle 14 along cannula 12 and carrier 34, until enlarged diameter portion 19 abuts opening 58 in shroud 36. At that point, sharp distal tip 16 of needle 14 has passed needle blocker 39, and needle blocker 39 has moved into lumen 48, urged there by spring 41 (turning about distal edge 59 of opening 37 in shroud 36), thereby blocking the path of sharp distal tip 16 of needle 14, should needle 14 move in the distal direction. Locking member 54 can now move out of hub 10 and deeper, or proximally, into latch 32, since needle blocker 39 is no longer obstructed by proximal edge 43 of first opening 40. This movement also releases latch member 38, so it can disengage with engaging member 11 of hub 10 (FIGS. 19-20).

The combination of needle blocker 39, needle 14, openings 37 in shroud 36 and first opening 40 in latch 32, and locking member 54 (on carrier 34) forms a locking assembly, which secures needle shield assembly 30 to hub 10. This locking assembly is only released when sharp distal tip 16 of needle 14 has passed needle blocker 39 and is thus shielded, thereby providing a passive safety shield which cannot disengage from hub 10 prior to shielding sharp distal tip 16 of needle 14. Needle shield assembly 30 is substantially external of hub 10 in this position, thus providing space within hub 10 for a blood sealing device 15, for example a septum or a luer-actuated valve, as well as a side port. The combination of enlarged diameter portion 19 and opening 37 in shroud 36 prevents proximal movement of sharp distal tip 16 of needle 14. This and other ways of preventing proximal movement of the needle 14 are shown in co-pending US patent applications No. 2008/0119795 A1, No. 2009/0137958 A1, and 2009/0249605 A1, each of which are referred to above and incorporated herein by reference.

Figure 23:
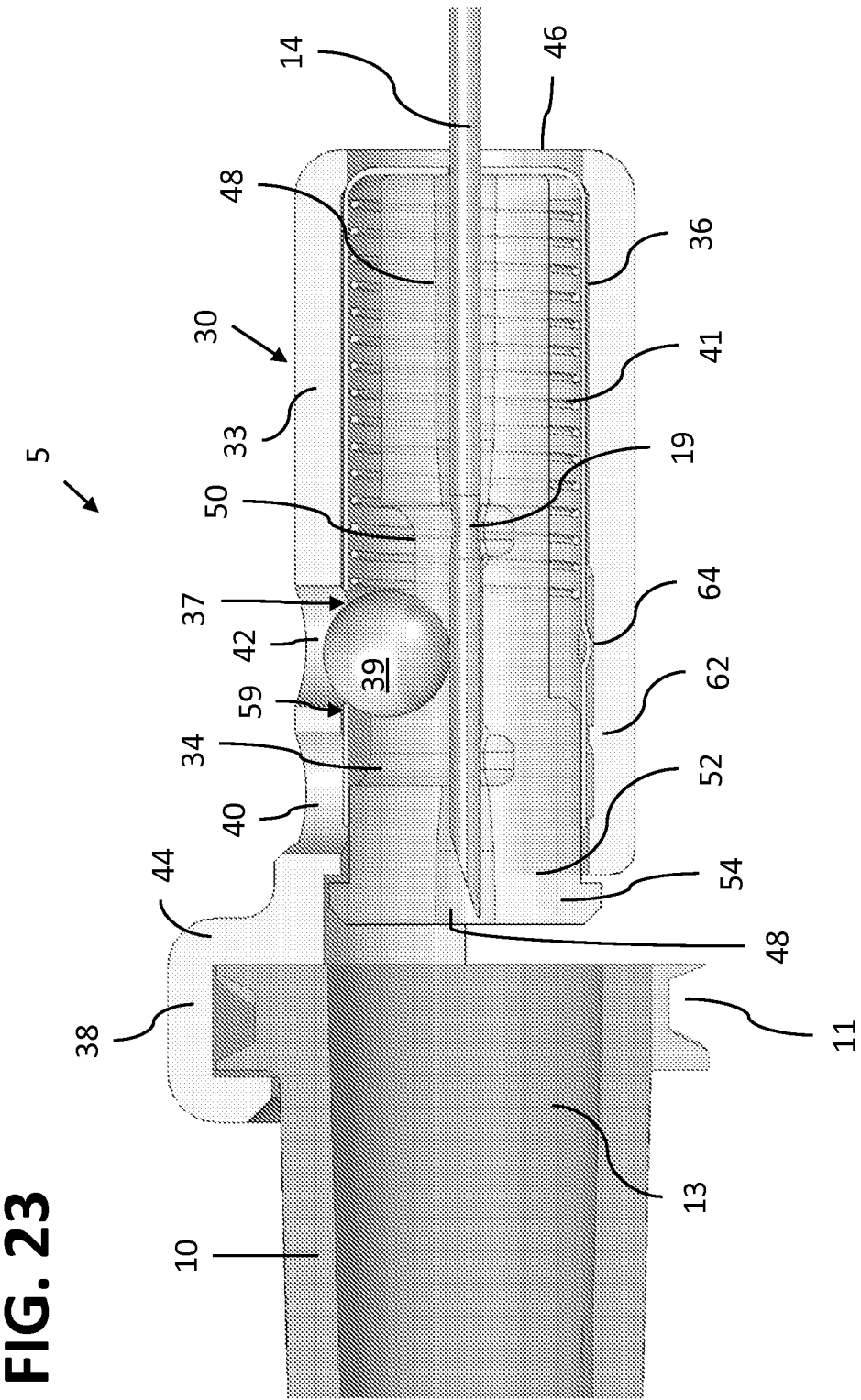
FIG. 23 shows a detailed cross-sectional view of the needle shield assembly in an intermediate step of manufacturing the device in accordance with embodiments of the invention.

A method of assembling or manufacturing the above-described device will now be described. With reference to FIG. 23, a needle blocker 39 may be placed in carrier 34. Carrier 34 may include: a locking member 54 on, or engaged with, a distal end 52 thereof, an axial lumen 48, and a channel 50 for carrying needle blocker 39. Carrier 34 may be inserted into shroud 36 until a proximal end of carrier 34 abuts proximal end 56 of shroud 36. Shroud 36 is then inserted into housing 33 of latch 32 until proximal end 56 of shroud 36 abuts a reduced diameter portion at a proximal end of latch 32. Latch 32 includes a latch member 38 extending from a portion of a distal end 44 of housing 33. Housing 33 further includes a first opening 40 through a wall thereof, and a second opening 42 through a wall thereof, located proximally of first opening 40.

Figure 24:
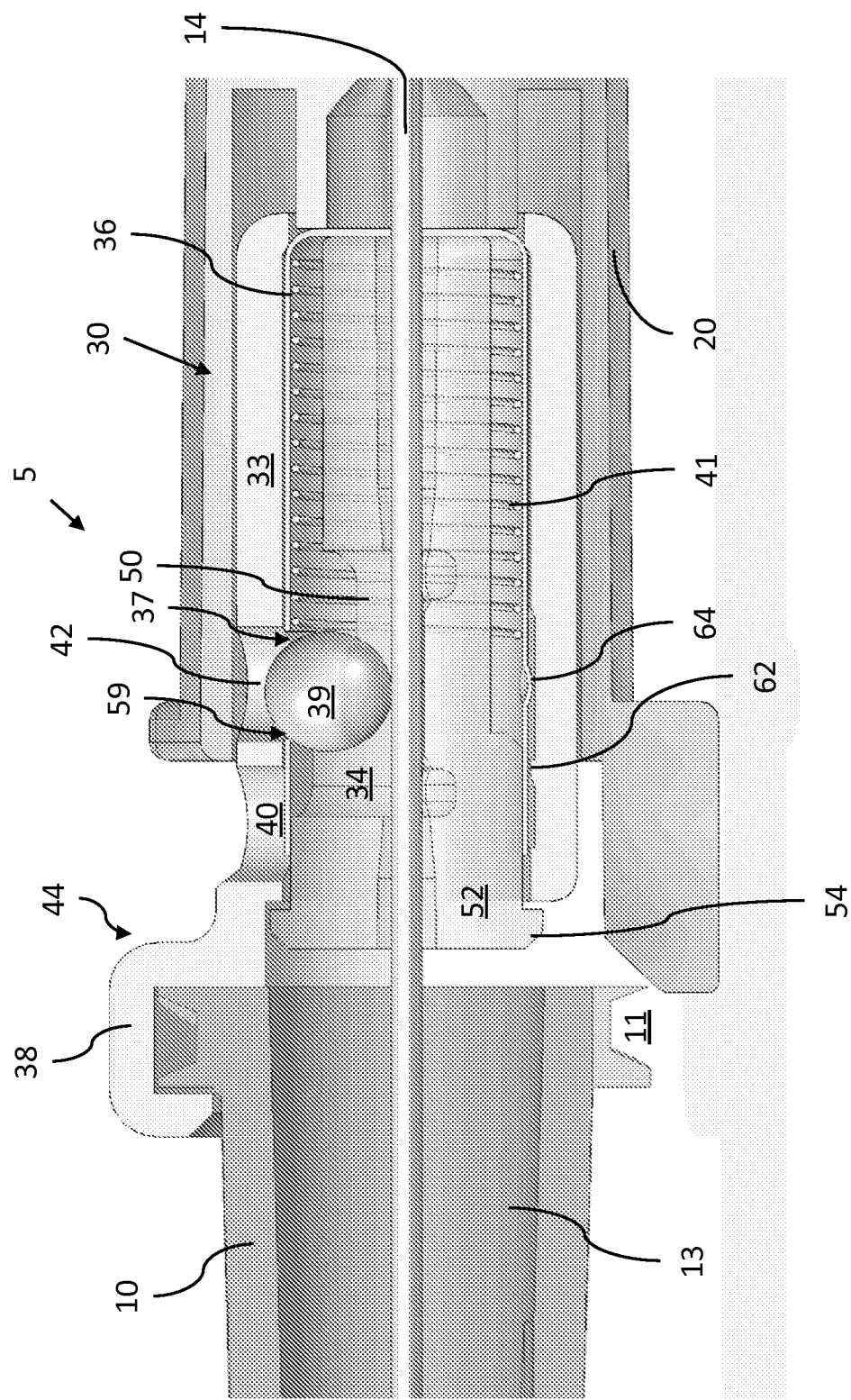
FIG. 24 shows a detailed cross-sectional view of the needle shield assembly and hub in an intermediate step of manufacturing the device in accordance with embodiments of the invention.
Figure 25:
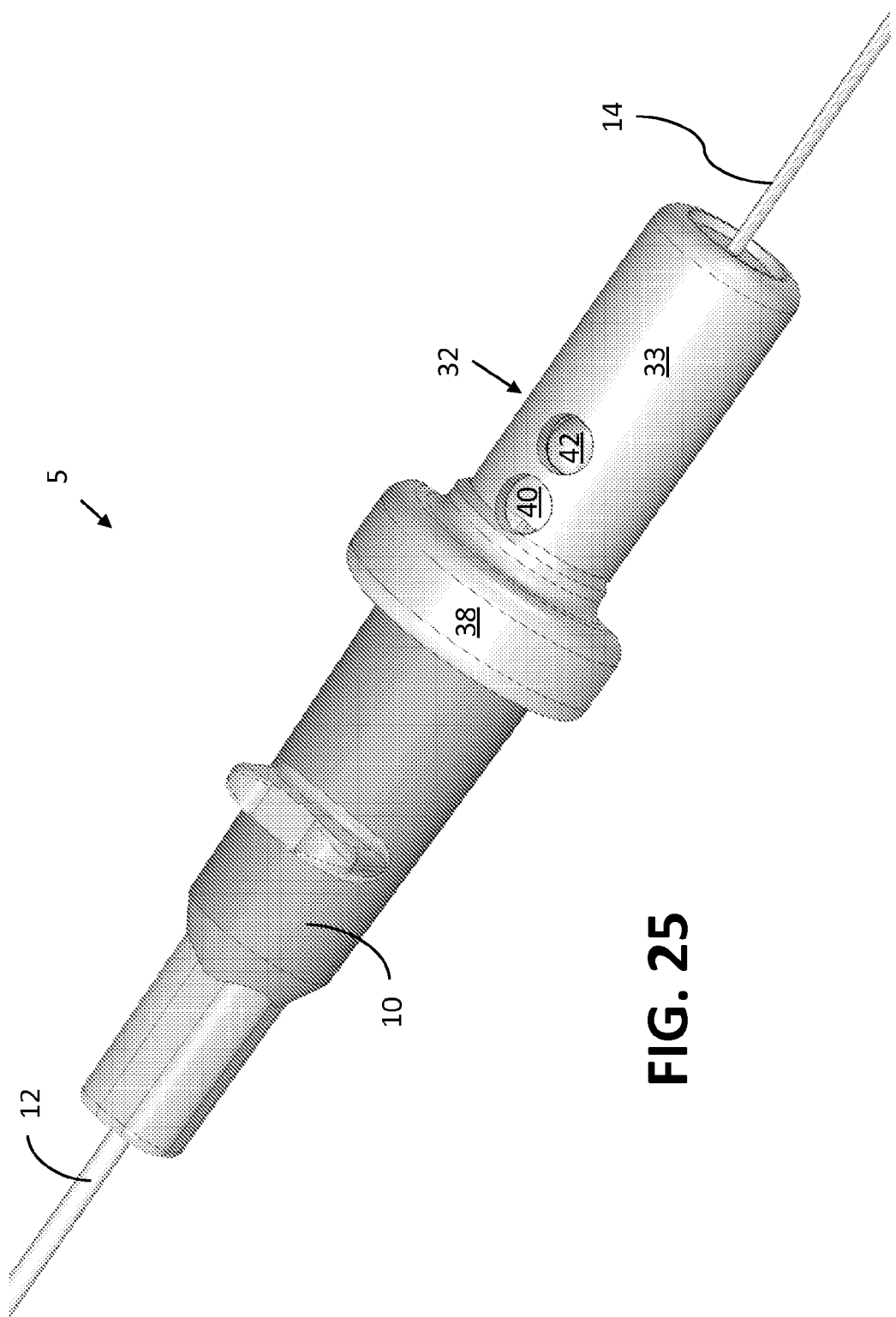
FIG. 25 shows a perspective view of a needle device including a needle shield assembly according to embodiments of the invention.
Figure 26:
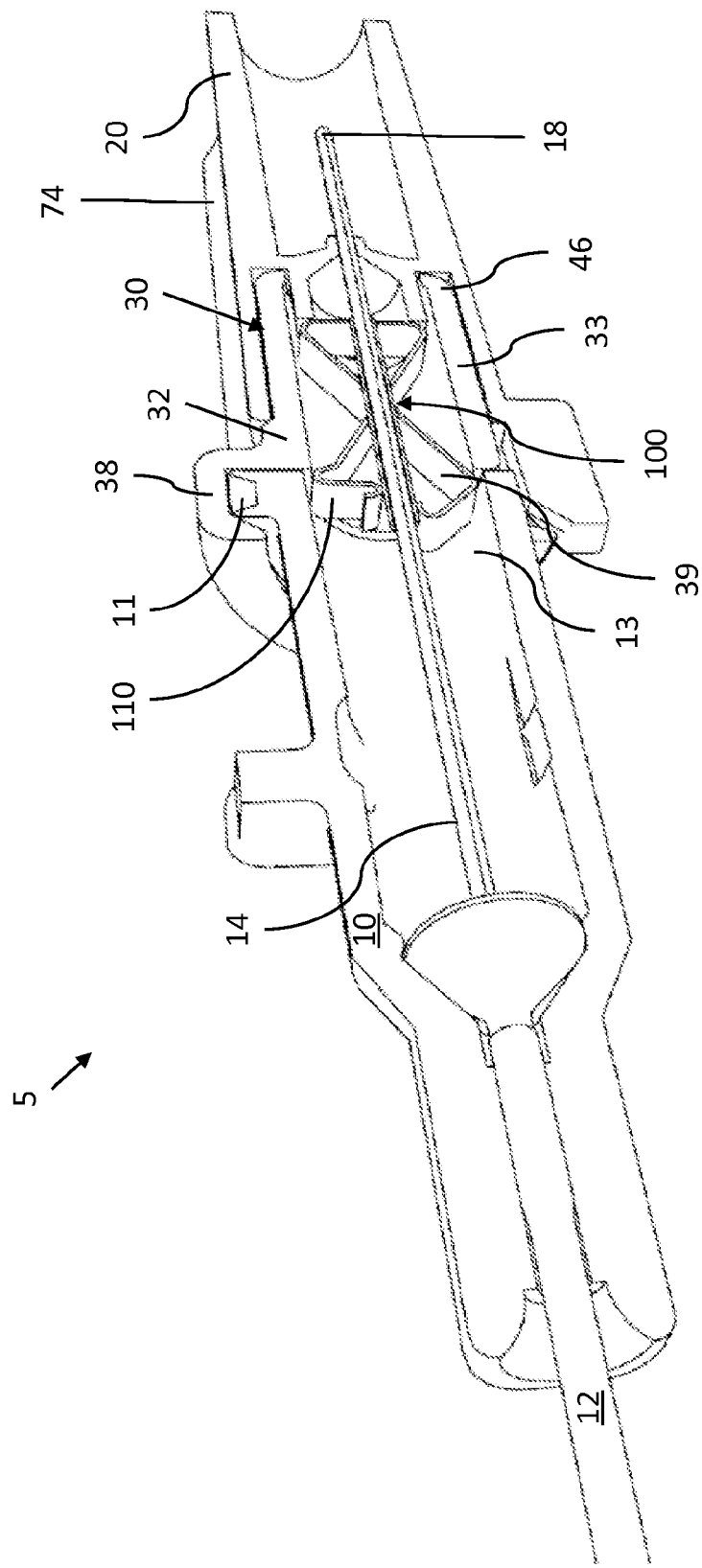
FIG. 26 shows a perspective view of a needle device including a needle shield assembly in a non-shielding position according to embodiments of the invention.
Figure 27:
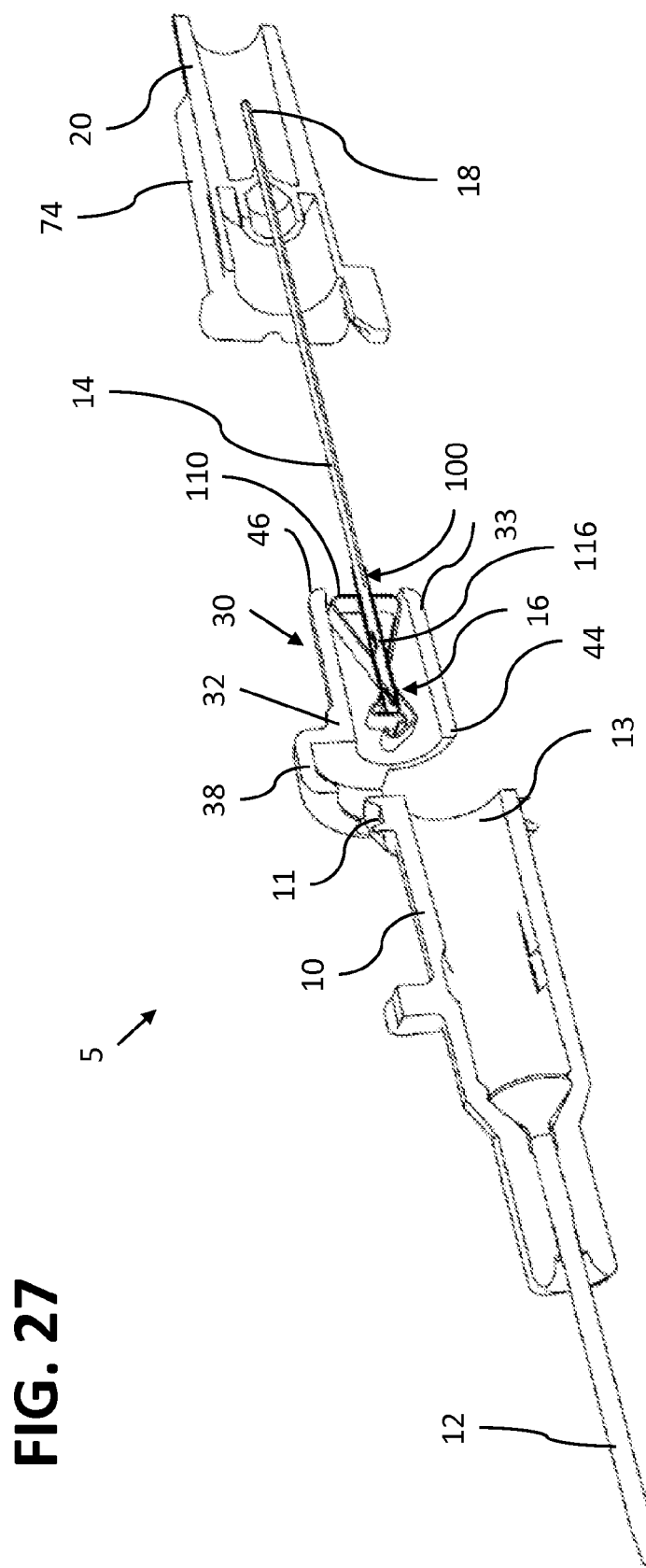
FIG. 27 shows a cutaway perspective view of a needle device including a needle shield assembly in a shielding position according to embodiments of the invention.
Figure 28:
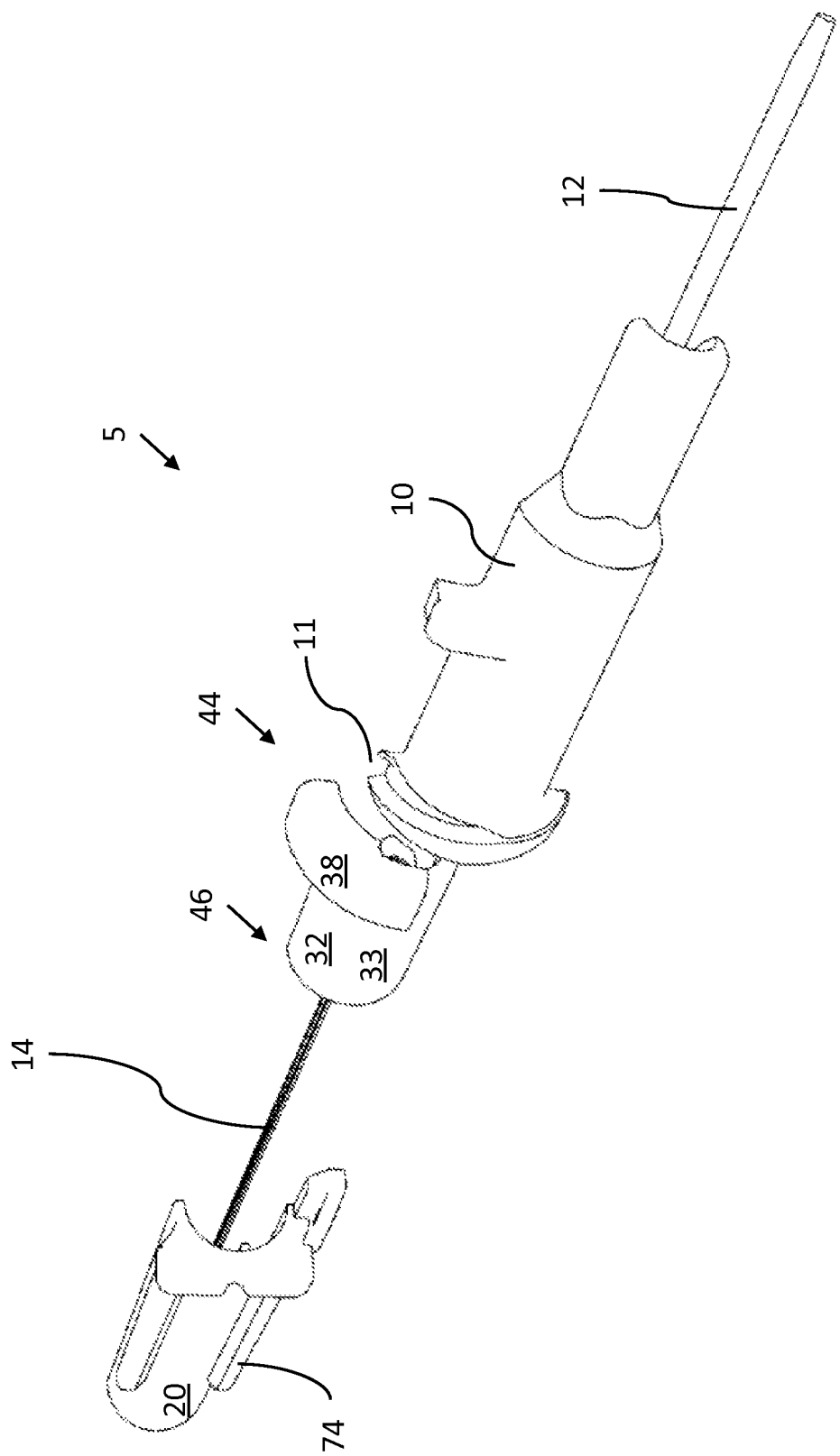
FIG. 28 shows a perspective view of a needle device including a needle shield assembly according to embodiments of the invention.

Proximal end 18 of needle 14 is inserted into distal end 52 of axial lumen 48 in carrier 34. Needle 14 displaces needle blocker 39 such that it protrudes at least partially into second opening 42 in latch 32, as shown in FIG. 23. Proximal end 18 of needle 14 is then affixed to needle hub 20, for example, with glue as shown in FIGS. 13 and 15. Hub 10 may have a flanged engaging member 11. Latch member 38 is engaged with flanged engaging member 11 of hub 10 as shown in FIG. 24. Hub 10 and cannula 12 are then threaded over distal tip 16 of needle 14. Needle shield assembly 30 is then inserted into needle hub 20, causing boss 21 to push locking member 54 distally into hub 10, slip fitting closely into it as shown in FIG. 15.

Hub 10 may include a female luer adapter 13 therein. The foregoing engagement of latching member 38 with flanged engaging member 11 of hub 10, and the insertion of locking member 54 into hub 10 cause needle blocker 39 to move distally within carrier 34 and out of second opening 42 (FIGS. 24-25), such that it protrudes into first opening 40 in latch 32 as in FIG. 15. Latch 32 may be configured to flex or expand slightly to allow needle blocker 39 to snap from second opening 42 to first opening 40. Needle shield assembly 30 is thus locked onto hub 10 and is ready for deployment as described herein.

Referring again to FIGS. 1-10, the above-described needle shield assembly 30 may further include a bushing 100. Bushing 100 may be substantially tubular in shape, and has an inner surface and an outer surface. Bushing 100 is disposed about needle 14 in a sleeve-like fashion. In a non-shielding position, as shown in FIGS. 1-4, the needle blocker 39 is biased radially inward against the outer surface of bushing 100. The biasing force on needle blocker 39 may be provided by, e.g., spring 41 (as shown in FIG. 13). In a transitional position, shown in FIGS. 5-6, needle blocker 39 pivots around a distal edge of bushing 100, to move from the non-shielding position to the shielding position. In the shielding position, as shown in FIGS. 7-10, the sharp distal tip 16 is positioned within the bushing 100, and at least a portion of the needle blocker 39 extends over a distal end of the bushing 100, blocking distal movement of the sharp distal tip 16 of the needle 14.

Figure 31:
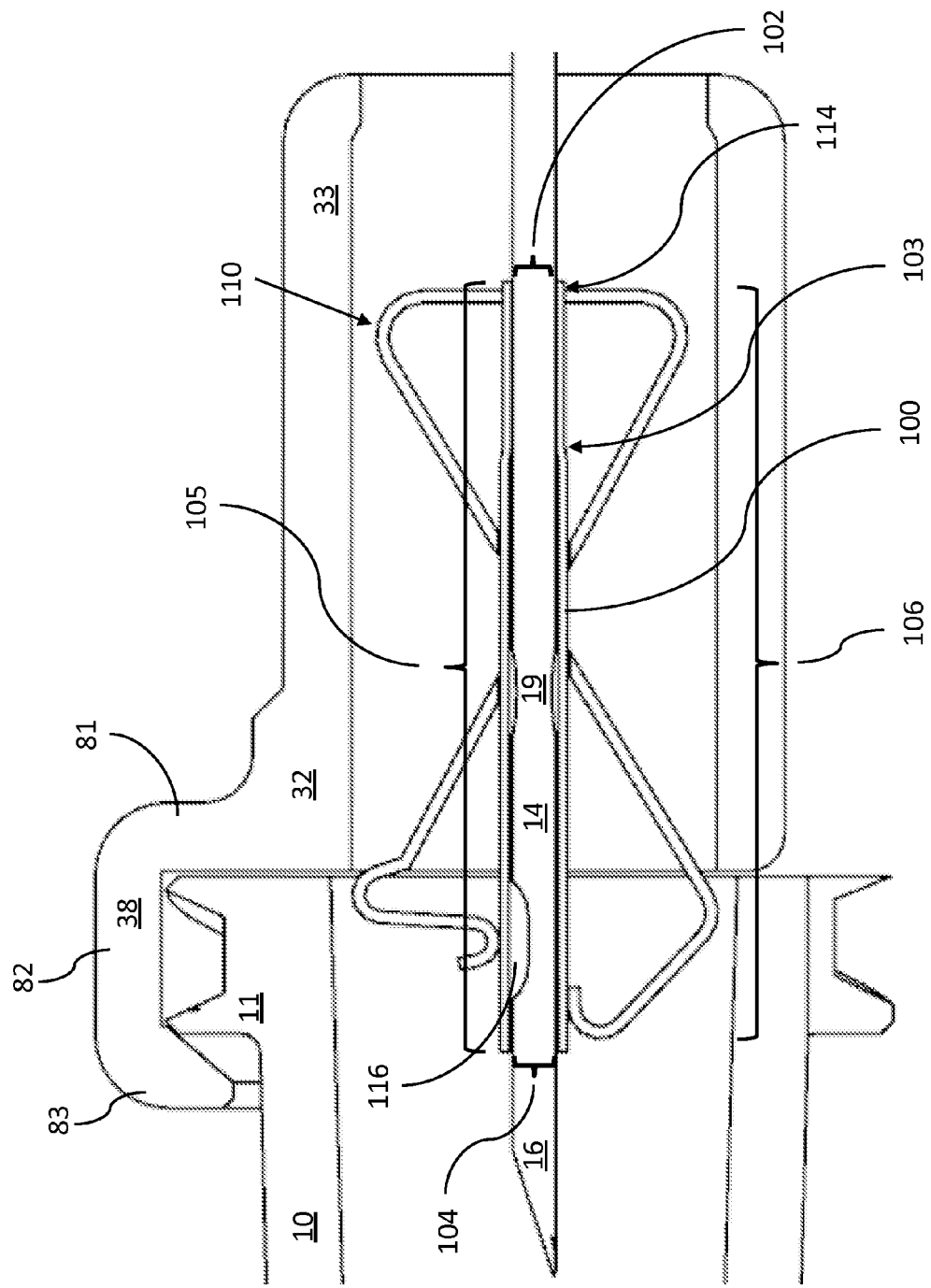
Figure 32:
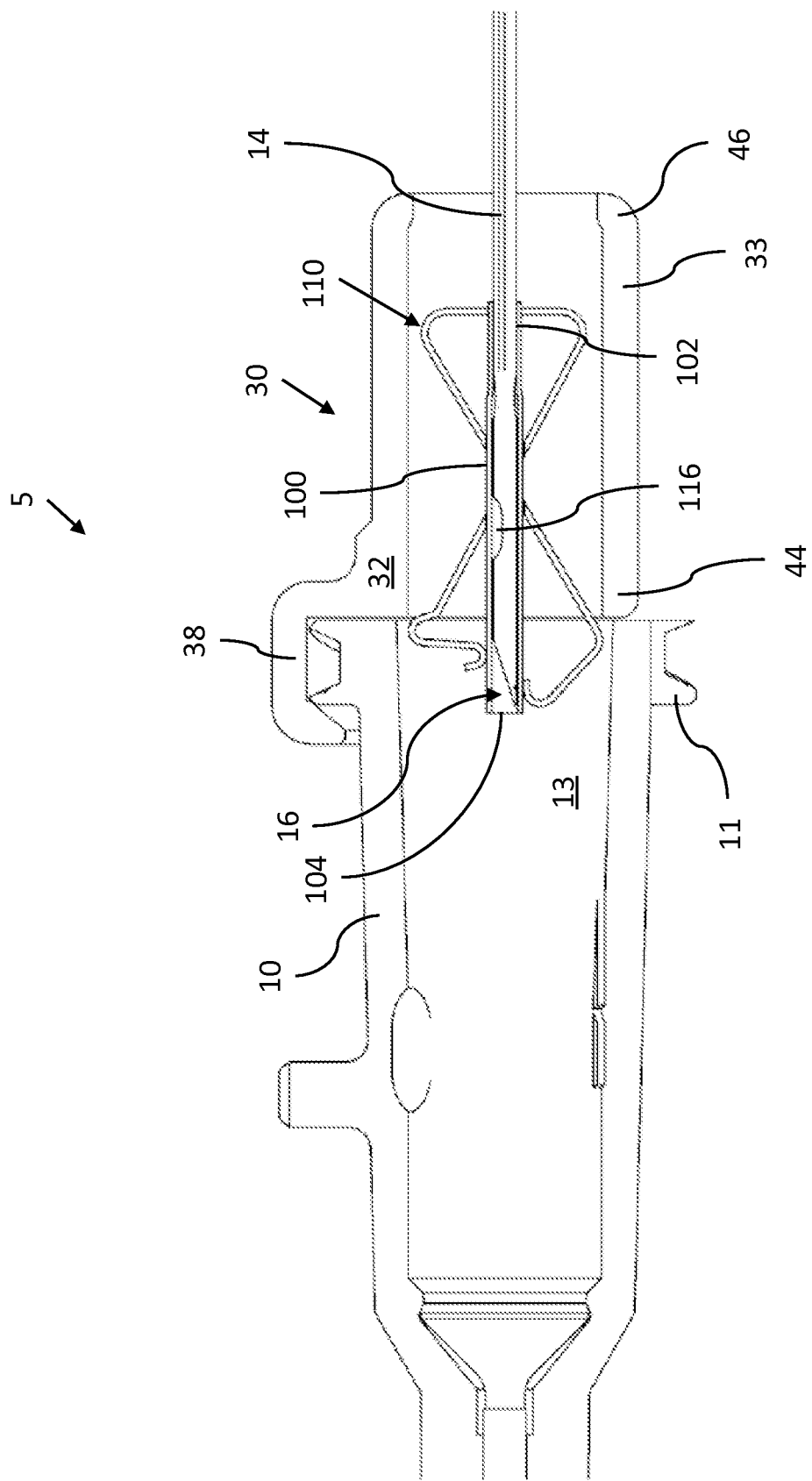

As noted above, needle 14 may include an enlarged diameter portion 19 which may be, e.g., a crimp in needle 14. As shown in an enlarged view in FIG. 31, bushing 100 may include a proximal inner diameter 102 that is smaller than the enlarged outer diameter portion 19 of needle 14, and a distal inner diameter 104 that is larger than the enlarged outer diameter portion 19 of needle 14. Distal inner diameter 104 allows needle 14 to be retracted in a proximal direction following use. Enlarged diameter portion 19 is accommodated by distal inner diameter 104 of bushing 100, allowing needle 14 to enter bushing 100 at the distal end and continue to move proximally until enlarged diameter portion 19 reaches point 103 where the inner diameter of bushing 100 transitions from the larger distal diameter 104 to the smaller proximal diameter 102. Point 103 and smaller proximal inner diameter 102 act as a stop for enlarged diameter portion 19 of needle 14, preventing needle 14 from proceeding any further in the proximal direction relative to bushing 100. This interaction prevents needle 14 from being drawn all the way through and out of bushing 100 at the proximal end.

As shown in FIGS. 1-10, in embodiments including a bushing 100, hole 58 at the proximal end of axial lumen 48 may be dimensioned to accommodate the smaller proximal outer diameter of bushing 100. Hole 58 does not accommodate the larger distal outer diameter of bushing 100, however, so as needle 14 moves proximally toward the shielding position, bushing 100 and needle 14 only move proximally relative to needle shield assembly 30 until point 103 on bushing 100 reaches hole 58. After that point, as needle 14 continues to move proximally relative to hub 10, needle shield assembly 30 moves proximally relative to hub 10 with needle 14 and bushing 100.

In embodiments including a bushing 100, such as those shown in FIGS. 1-10, needle blocker 39 contacts the outer surface of bushing 100, and does not contact an outer surface of needle 14 itself in the non-shielding and transitional positions (FIGS. 1-6). Bushing 100 is fashioned such that an axial drag force between the outer surface of needle 14 and the inner surface of bushing 100 is less than an axial drag force between the outer surface of bushing 100 and needle blocker 39. Therefore, needle blocker 39 and needle 14 do not contact one another. This interaction avoids any potential drag from needle blocker 39 on needle 14 that could otherwise slow or impede proximal movement of needle 14 toward the shielding position, because any frictional drag occurs on bushing 100 instead of needle 14. Bushing 100 also ensures that a distal side notch or opening 116 on needle 16, which may be used for early blood flashback visualization, cannot snag on needle blocker 39 during needle withdrawal and proximal movement.

As shown in FIGS. 26-54, other embodiments of device 5 may include a needle blocker 39 in the form of a clip needle guard 110 that is movable between a non-shielding position and a shielding position. Clip needle guards of the type considered are described in U.S. Pat. No. 7,611,499, which is incorporated herein by reference.

Clip needle guard 110 includes a first axially extending arm 120. First axially extending arm 120 includes a radially extending member 122 on a distal end thereof. First axially extending arm 120 may include a bend coupling the axially extending arm 120 with the radially extending member 122.

In some embodiments, as shown in FIG. 55, only a first axially extending arm 120 may be used. In other embodiments, such as shown in FIGS. 26-54, clip needle guard 110 may further include a proximal wall 112, and a second axially extending arm 130. In such embodiments, first and second axially extending arms 120, 130 extend in a distal direction from proximal wall 112. Proximal wall 112 may further include an opening 114 through which needle 14 may pass.

First and second axially extending arms 120, 130 may be joined at their proximal ends to proximal wall 112 in a hinged or angled arrangement. The distal ends of each of first and second axially extending arms 120, 130 each include radially extending members 122, 132 respectively, which may in turn include a lip 124, 134. Lips 124, 134 may extend either distally or proximally from the respective radially extending members 122, 132.

In the non-shielding position, clip needle guard 110 is disposed at least partially within hub 10, and a radially outermost portion of at least one of the first axially extending arm 120 and the second axially extending arm 130 (when present) retains a position of the clip needle guard 110 relative to the hub 10. The inner diameter of hub 10 constrains first and second axially extending arms 120, 130 from spreading any further in a radially outward direction, and biases radially extending members 122, 132 toward the longitudinal axis 17 (FIG. 29) such that the curve coupling radially extending members 122, 132 to the respective lips 124 and 134 are biased against an outer surface of needle 14 or, where present, an outer surface of bushing 100. In cross section, shown in FIGS. 57-58, axially extending arms 120, 130 form an approximate rectangle, the four corners 138 of which contact or are in close proximity to the inner diameter of hub 10. The approximate rectangle formed by four corners 138 is too large to allow clip needle guard 110 to move proximally into housing 33. Biasing means, such as bosses 140 (FIG. 56) or other structures, may aid in achieving and/or maintaining the location of clip needle guide 110 in the device and restricting rotation and/or axial movement while in the non-shielding position.

Figure 33:
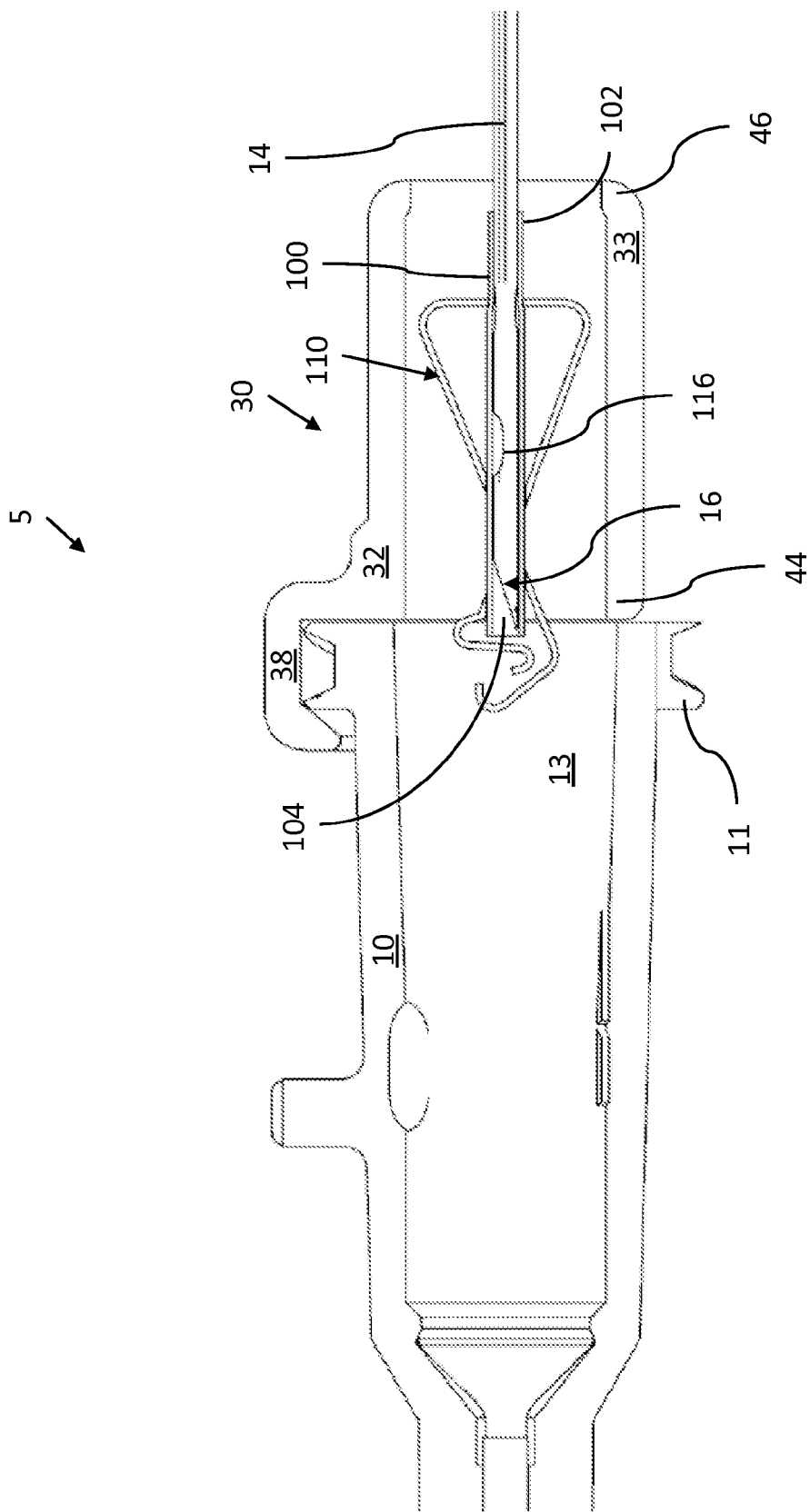
Figure 34:
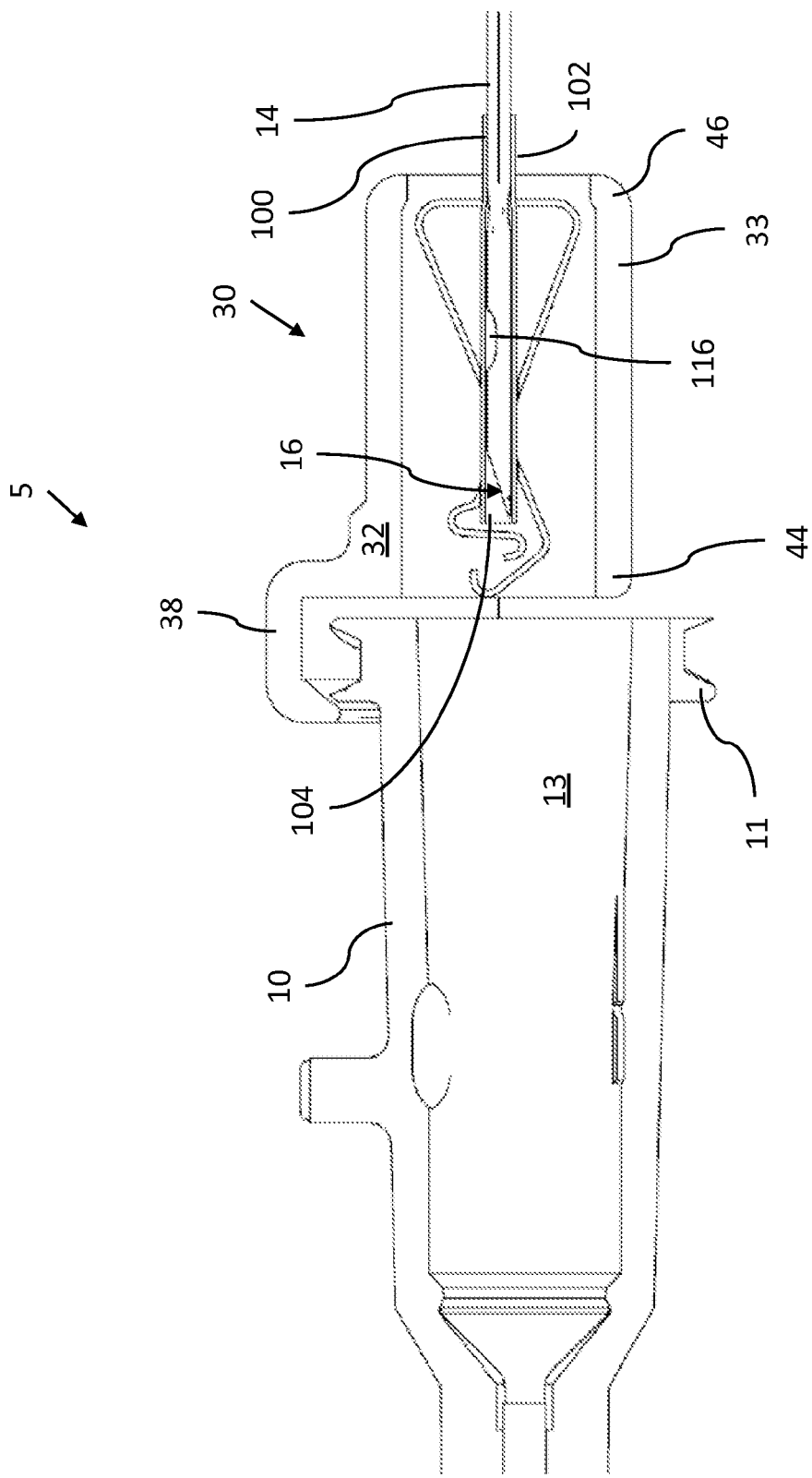
Figure 44:
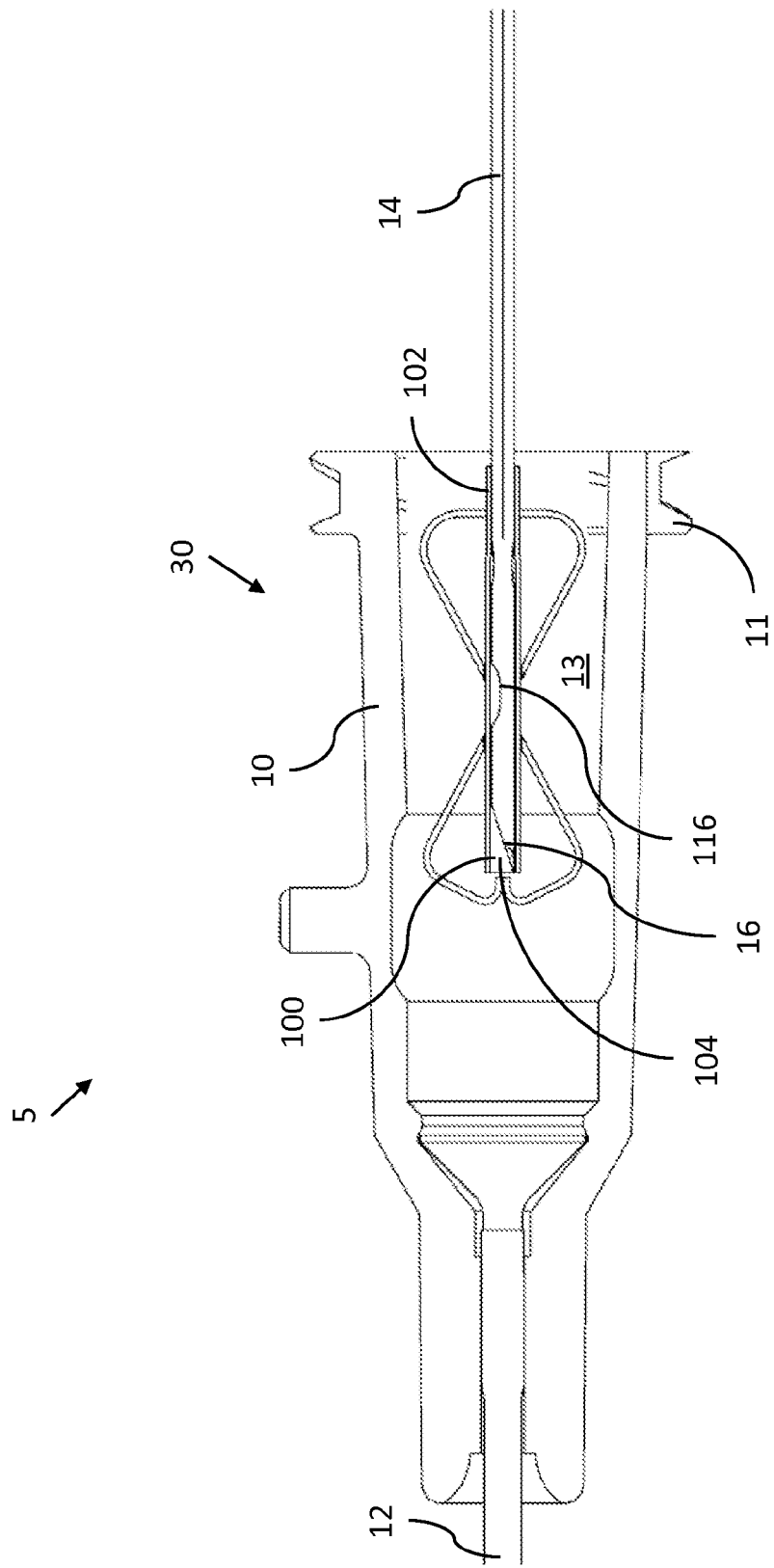
Figure 45:
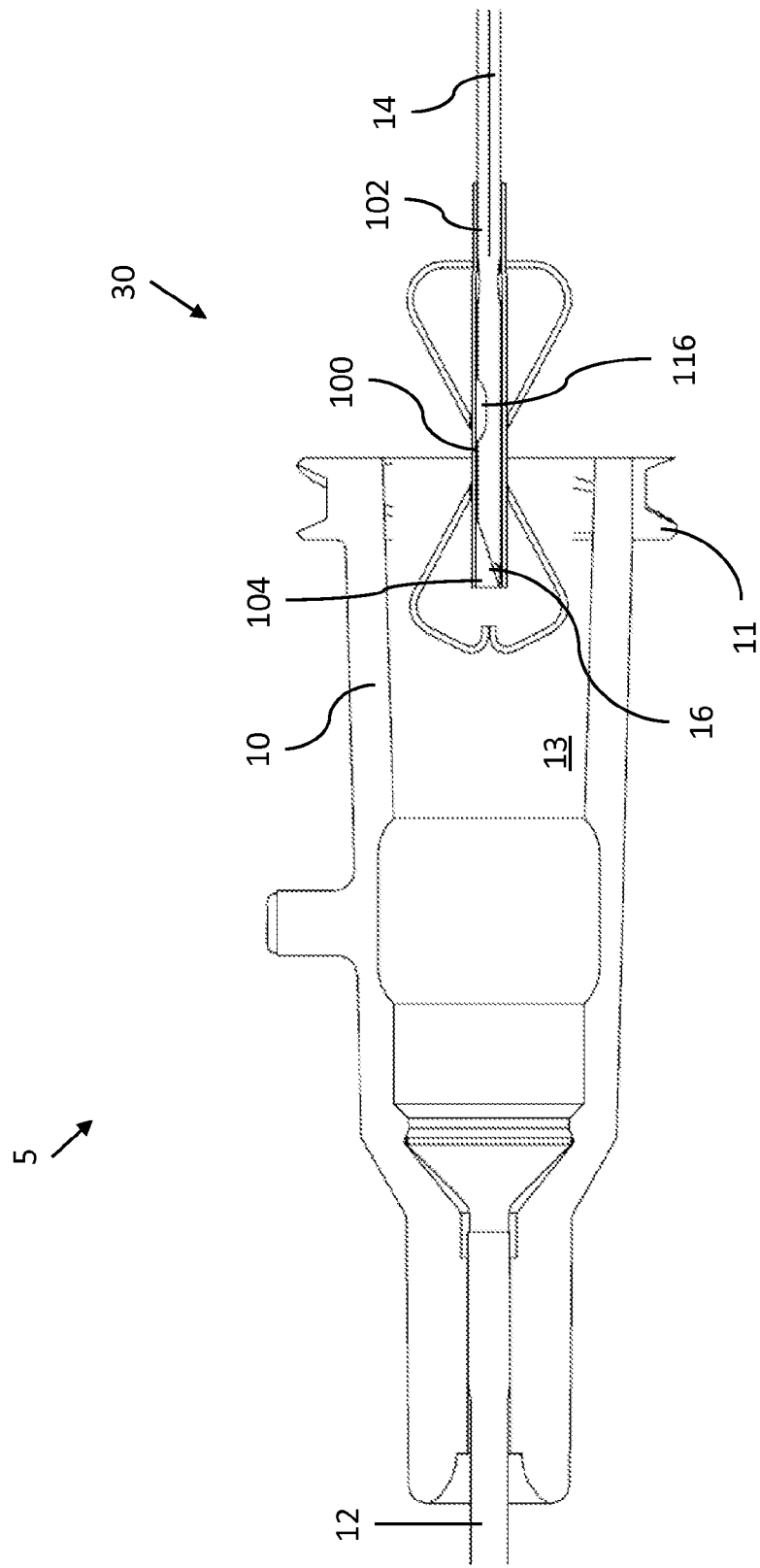
Figure 46:
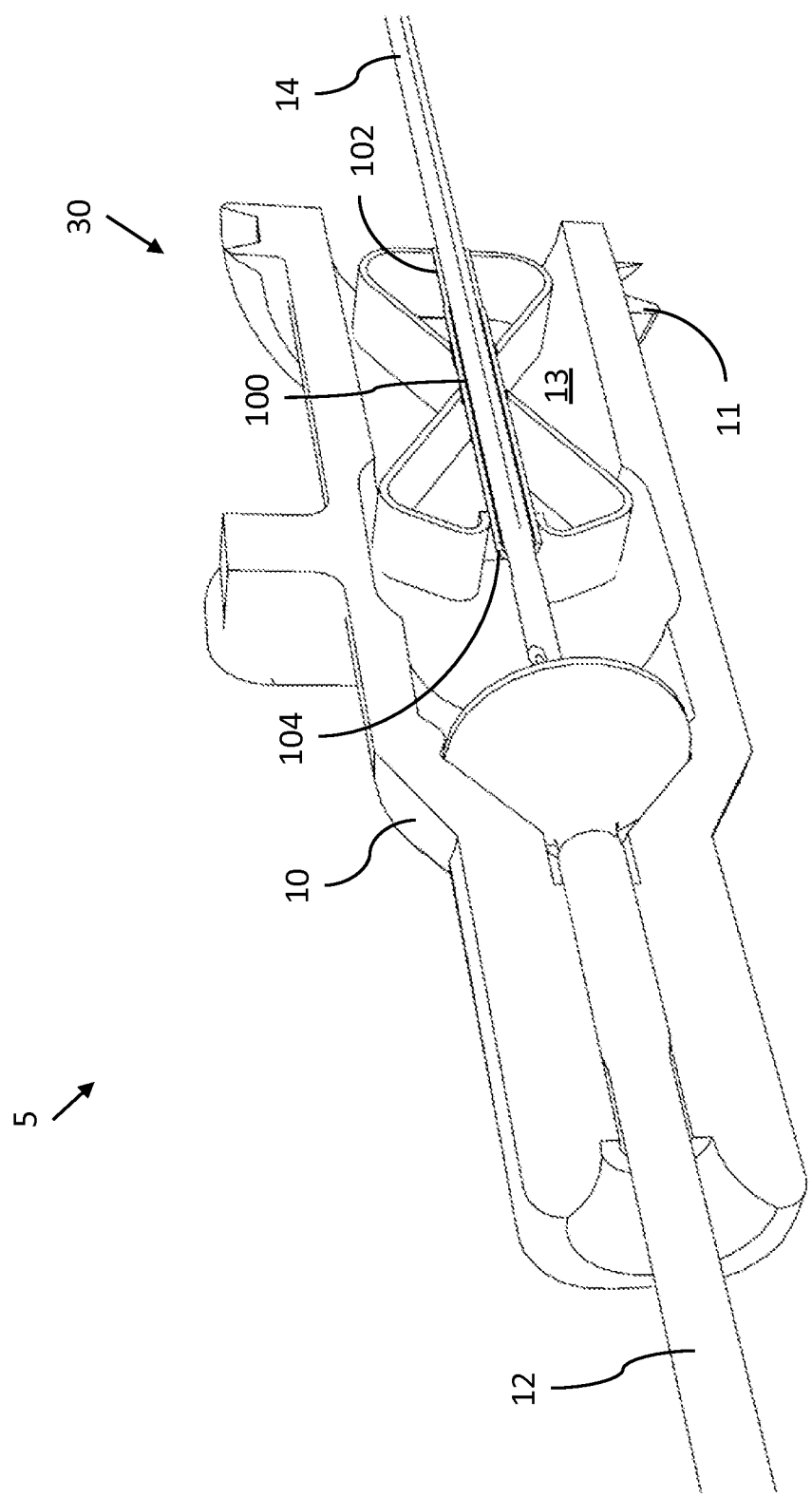
FIGS. 46-49 show perspective views of a needle device including a needle shield assembly progressing from a non-shielding position (FIG. 46) to a shielding position (FIG. 49) according to embodiments of the invention.
Figure 47:
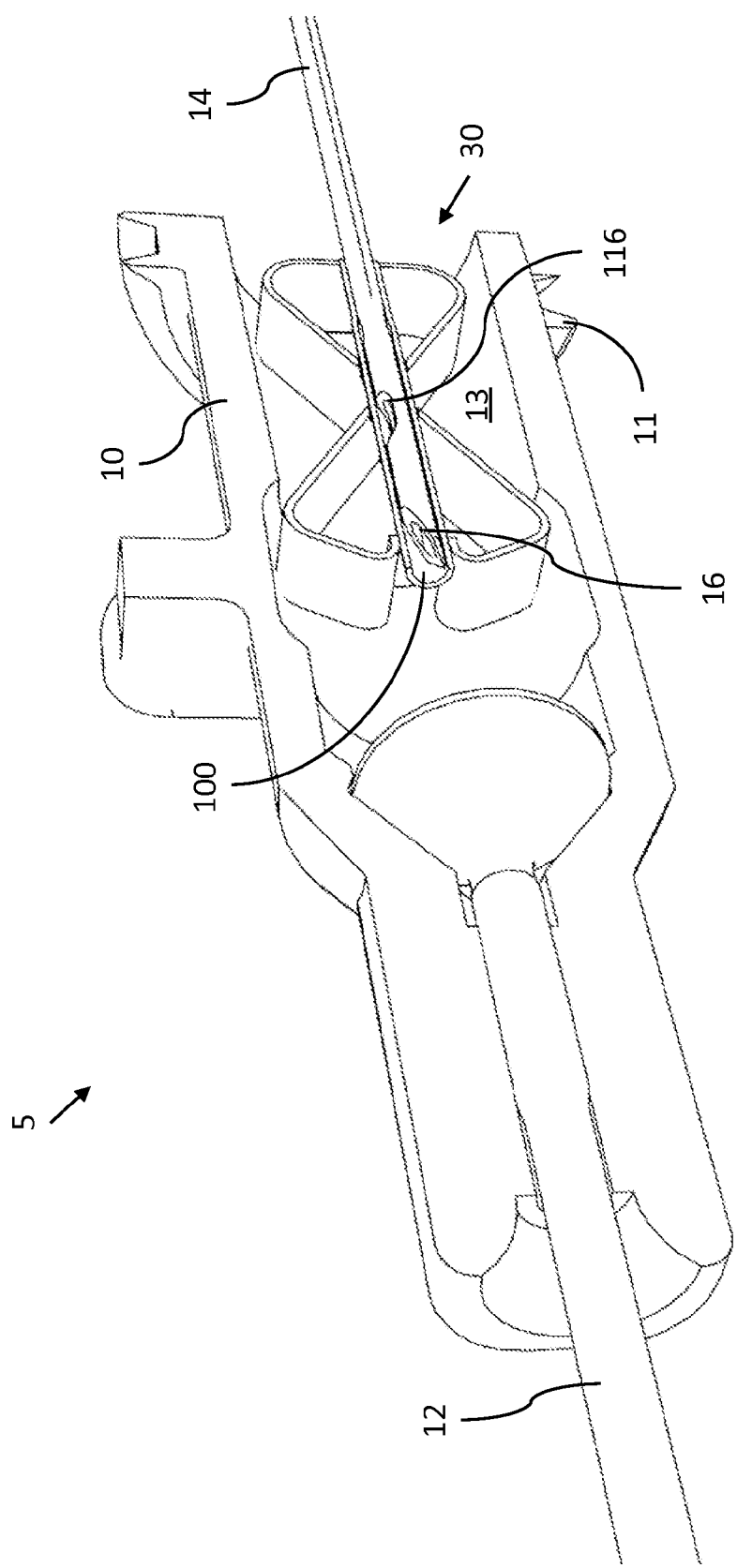
Figure 48:
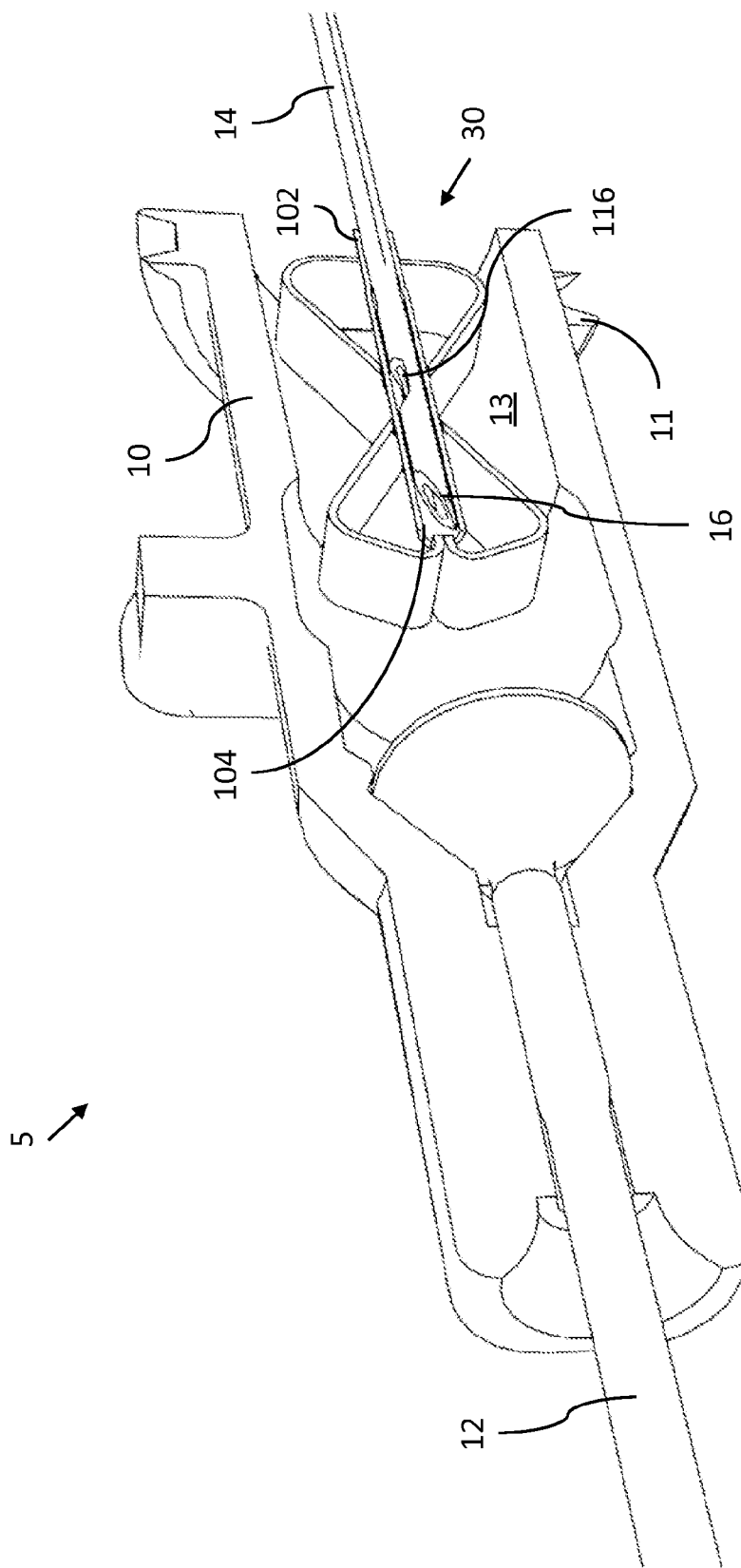
Figure 49:
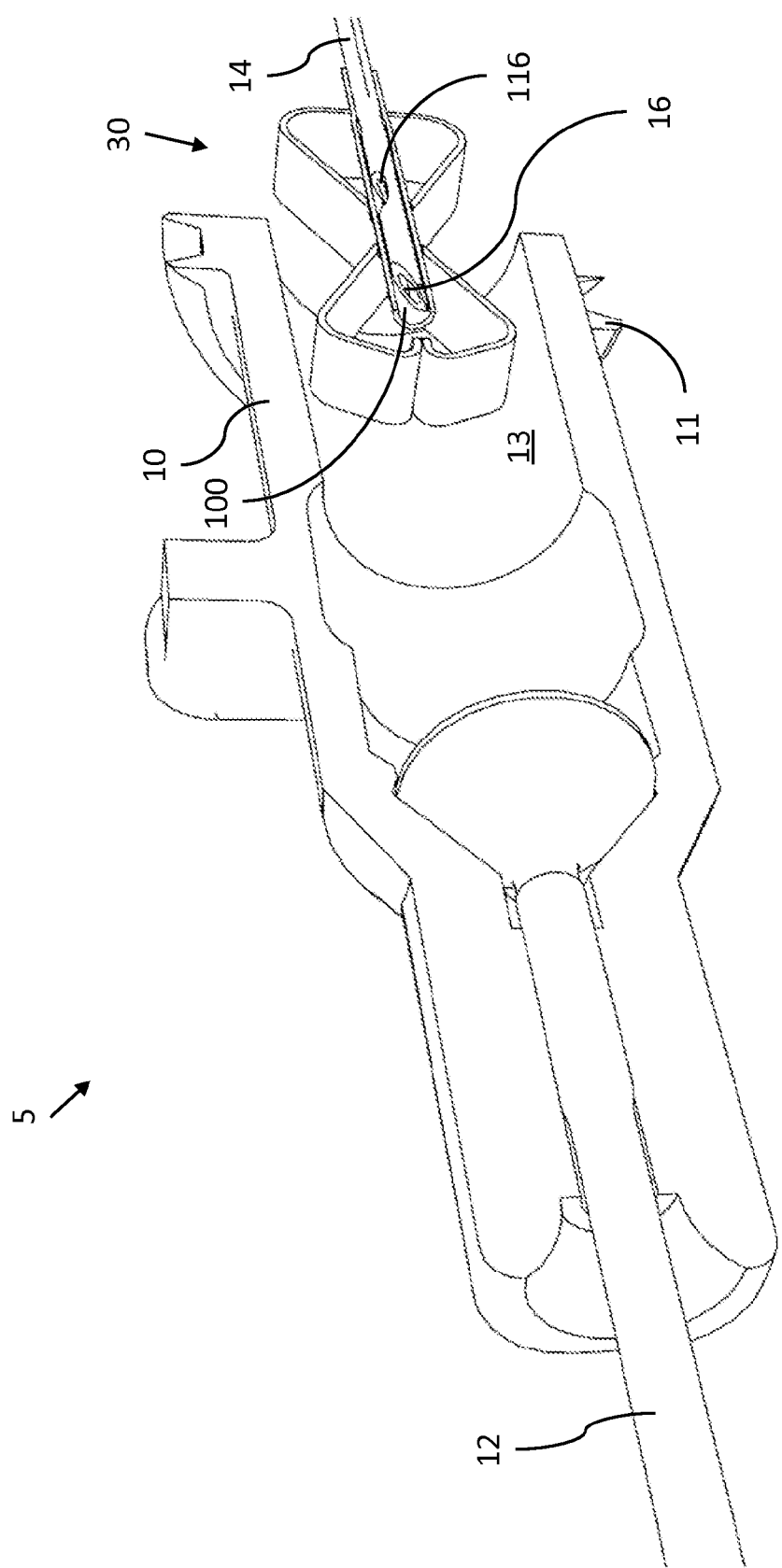
Figure 50:
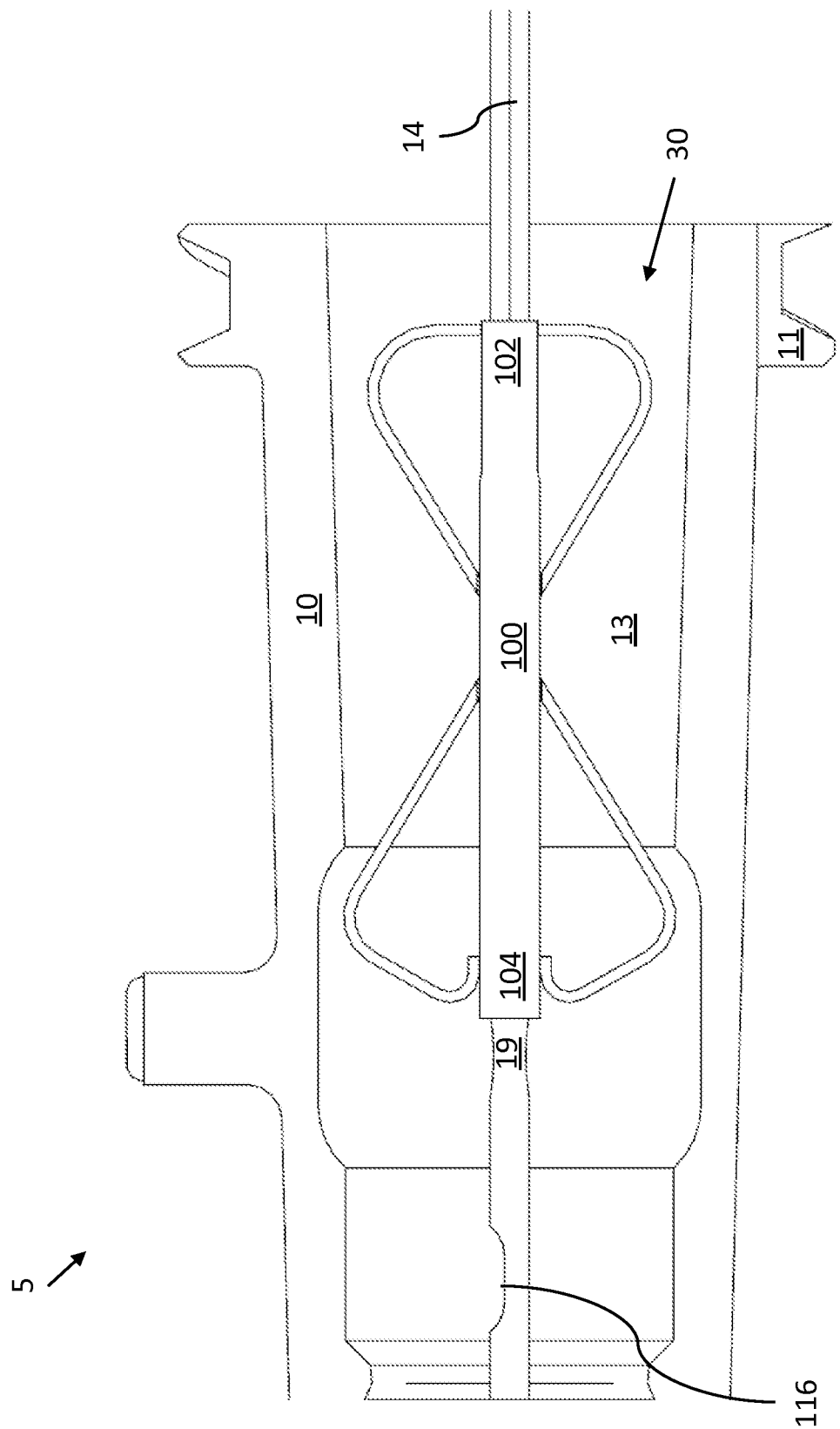
FIGS. 50-54 show cross sectional views of a needle device including a needle shield assembly progressing from a non-shielding position (FIG. 50) to a shielding position (FIG. 54) according to embodiments of the invention.
Figure 51:
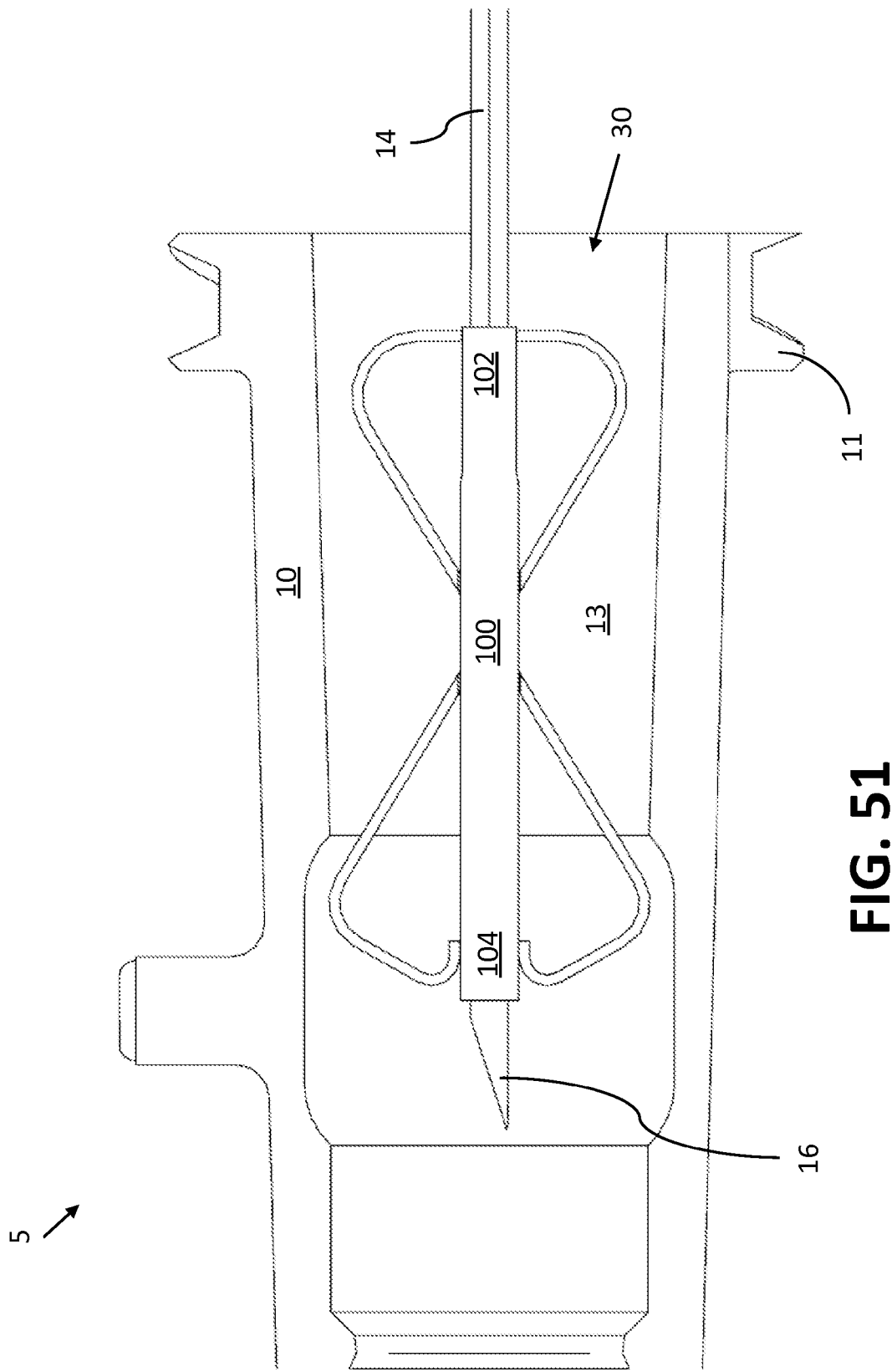
Figure 52:
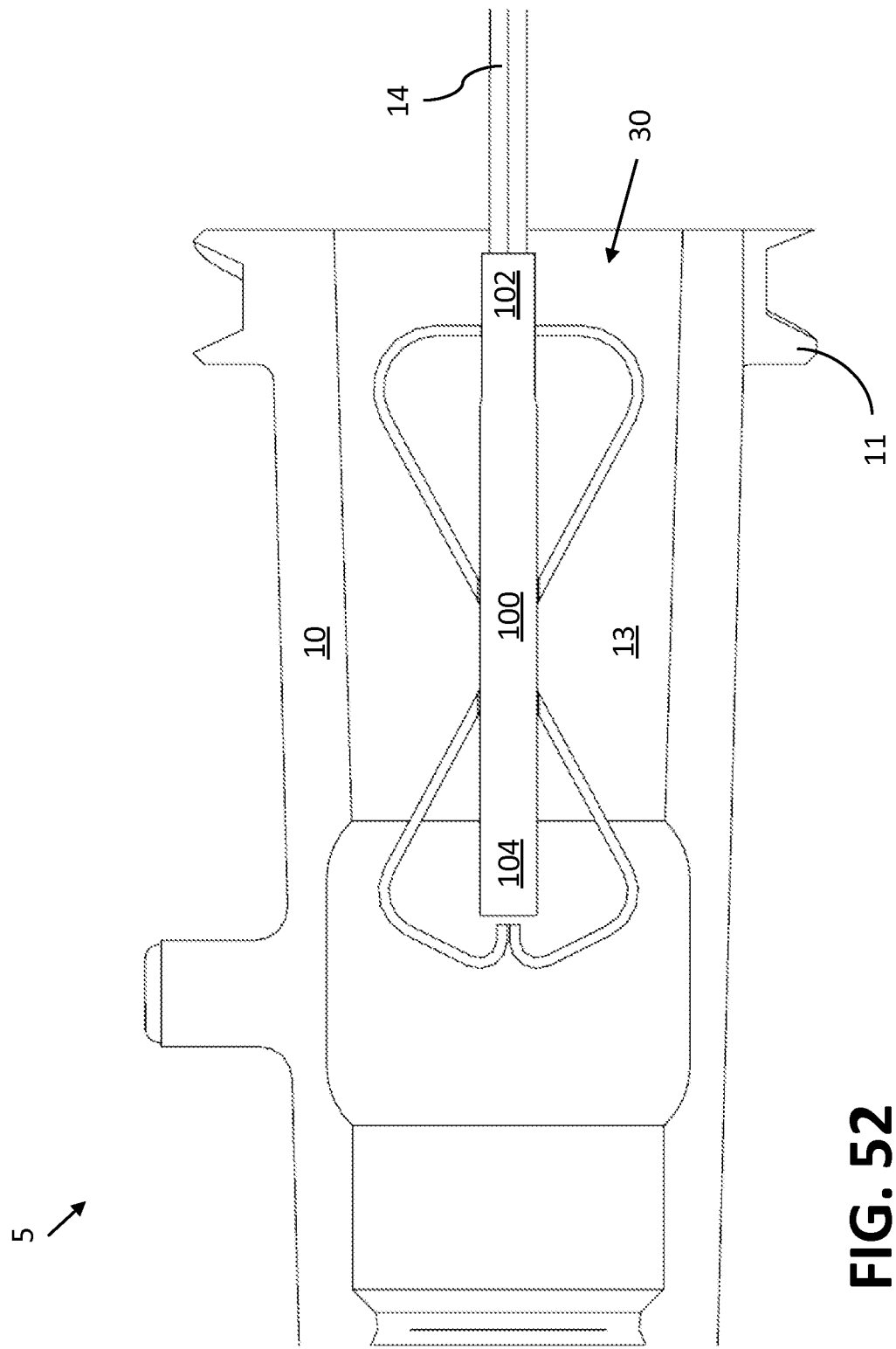
Figure 53:
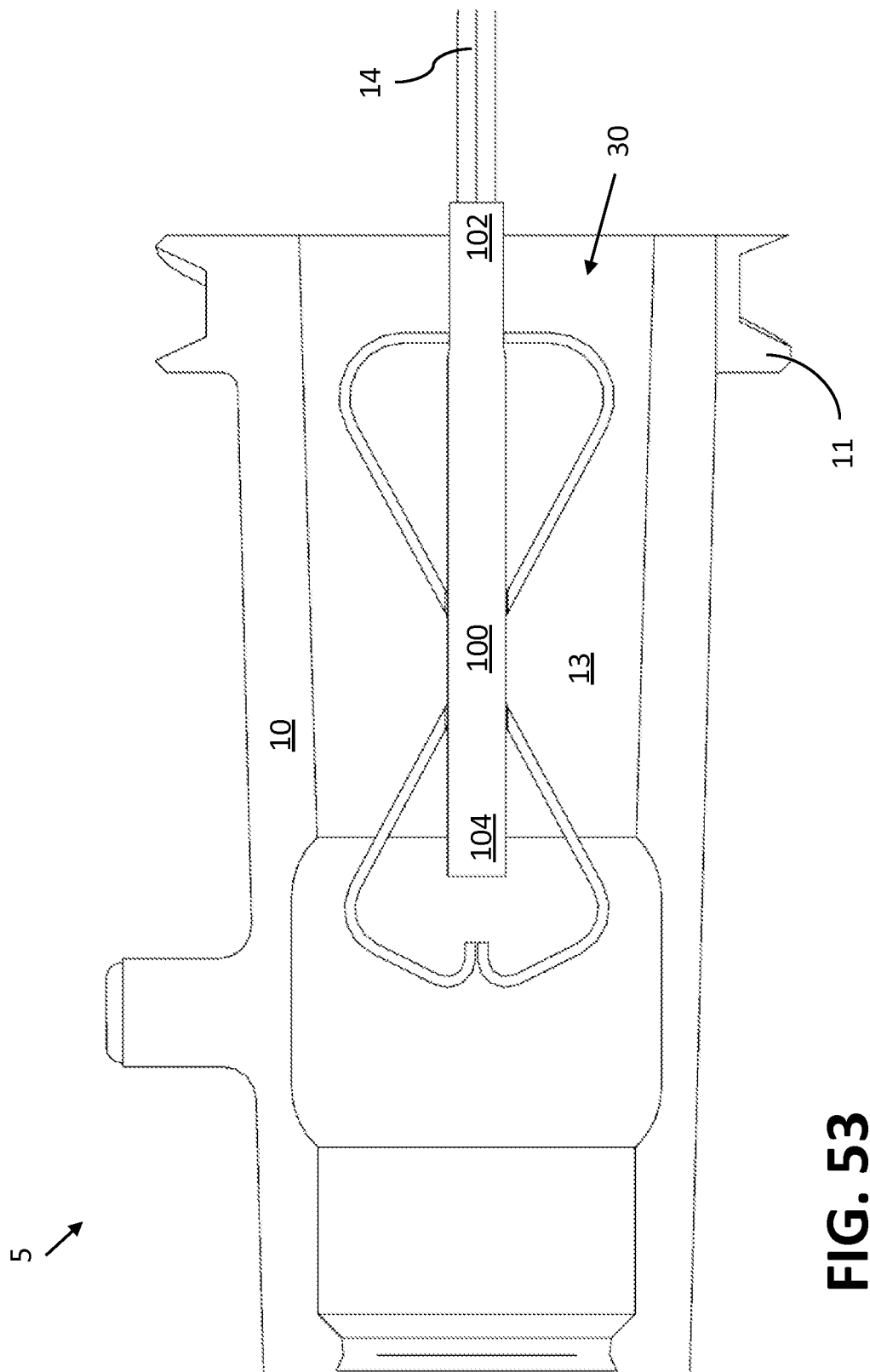

In the shielding position, in response to needle 14 and optional bushing 100 being moved proximally such that they do not occupy the space along the longitudinal axis 17 that separates the radially inward faces of lips 124, 134, radially extending members 122, 132 move radially inward to block distal movement of the sharp distal tip of the needle (FIGS. 33-34, 44). In some embodiments, radially extending members 122, 132 cross longitudinal axis 17, with one disposed proximally of the other (FIGS. 26-27 and 29-41), and sharp distal tip 16 of needle 14 is disposed proximally of both radially extending members 122, 132. In other embodiments, shown in FIGS. 42-54, neither radially extending member 122, 132 crosses longitudinal axis 17, but both approach it such that they meet approximately along the longitudinal axis 17 in the shielding position, and block the sharp distal tip 16 from moving distally beyond radially extending members 122, 132.

Figure 29:
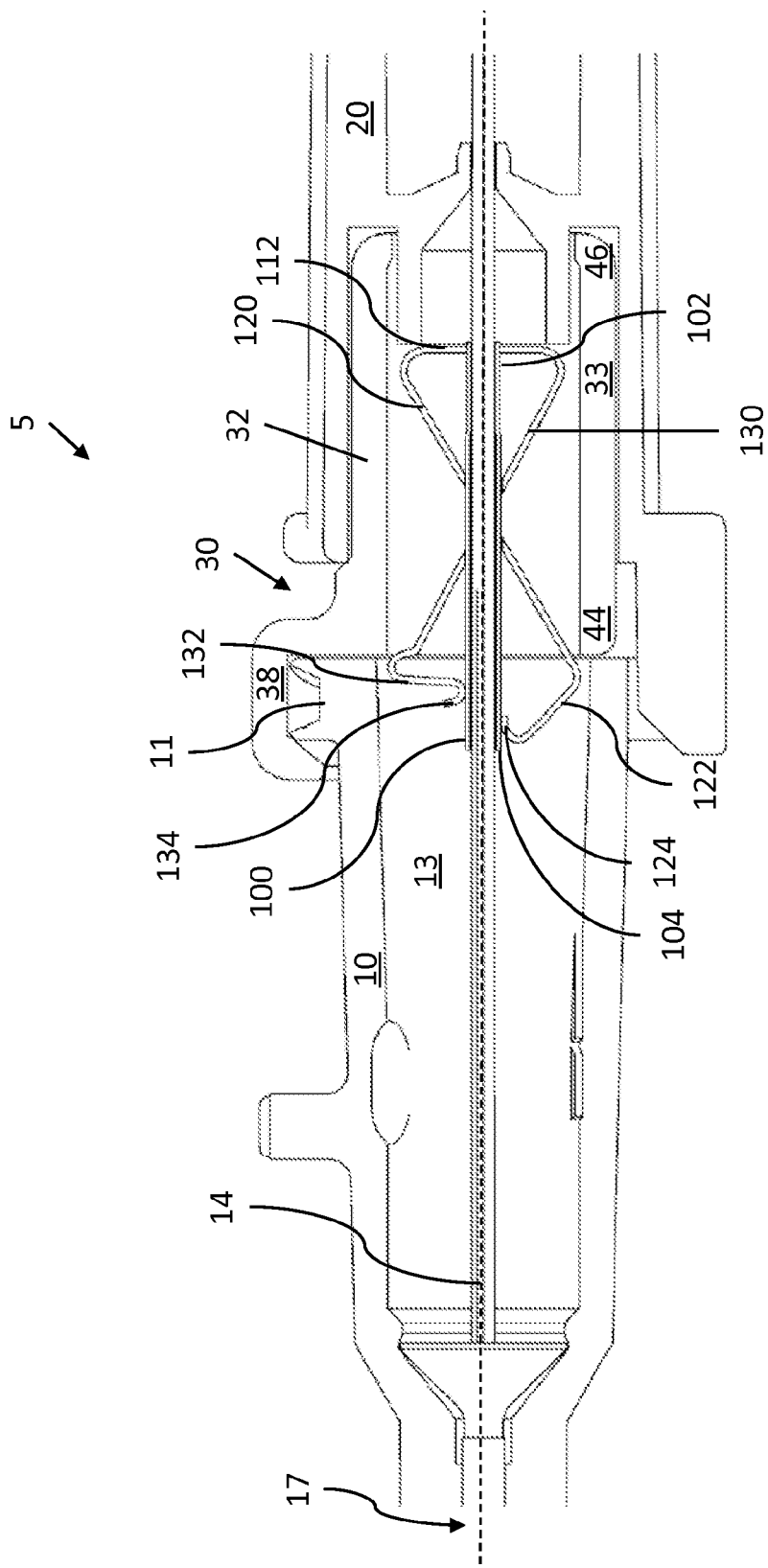
FIGS. 29-35 show cross sectional views of a needle device including a needle shield assembly progressing from a non-shielding position (FIG. 29) to a shielding position (FIG. 35) according to embodiments of the invention.
Figure 30:
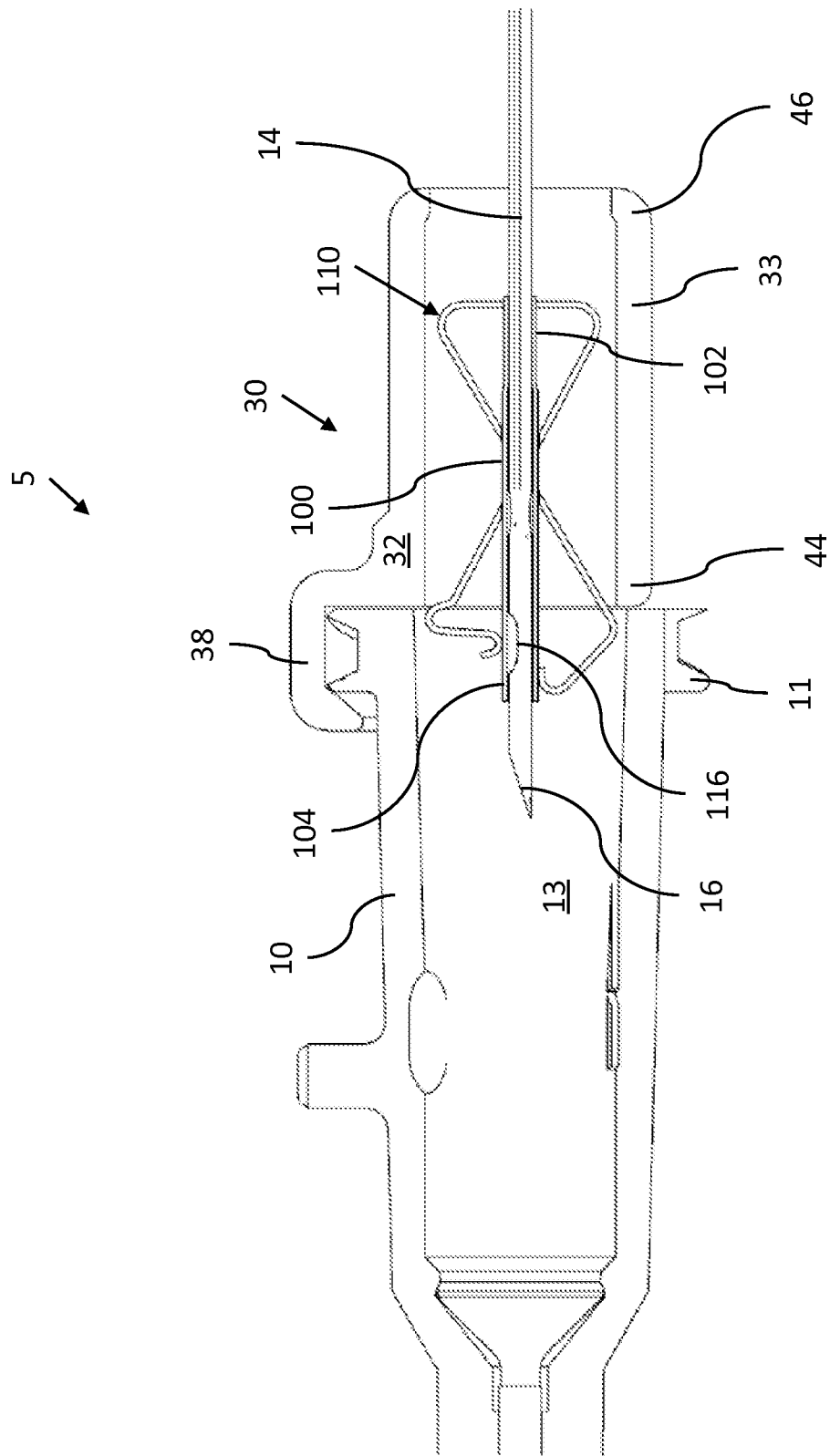

As shown in FIGS. 26-41, in some embodiments, clip needle guard 110 may be used together with latch 32, described above. As noted, in the non-shielding position, clip needle guard 110 is disposed at least partially within hub 10, and a radially outermost portion of at least one of the first axially extending arm 120 and the second axially extending arm 130 (when present) retain a position of the clip needle guard 110 relative to the hub 10. At least a portion of clip needle guard 110, particularly a proximal end thereof, is disposed within housing 33 of latch 32 as shown in FIG. 29. Latch member 38 engages engaging member 11 on the exterior of the hub 10 as described above. The radially outermost points along each of axially extending arms 120, 130 function as a locking member 54 to retain latch 32 in engagement with hub 10.

Figure 35:
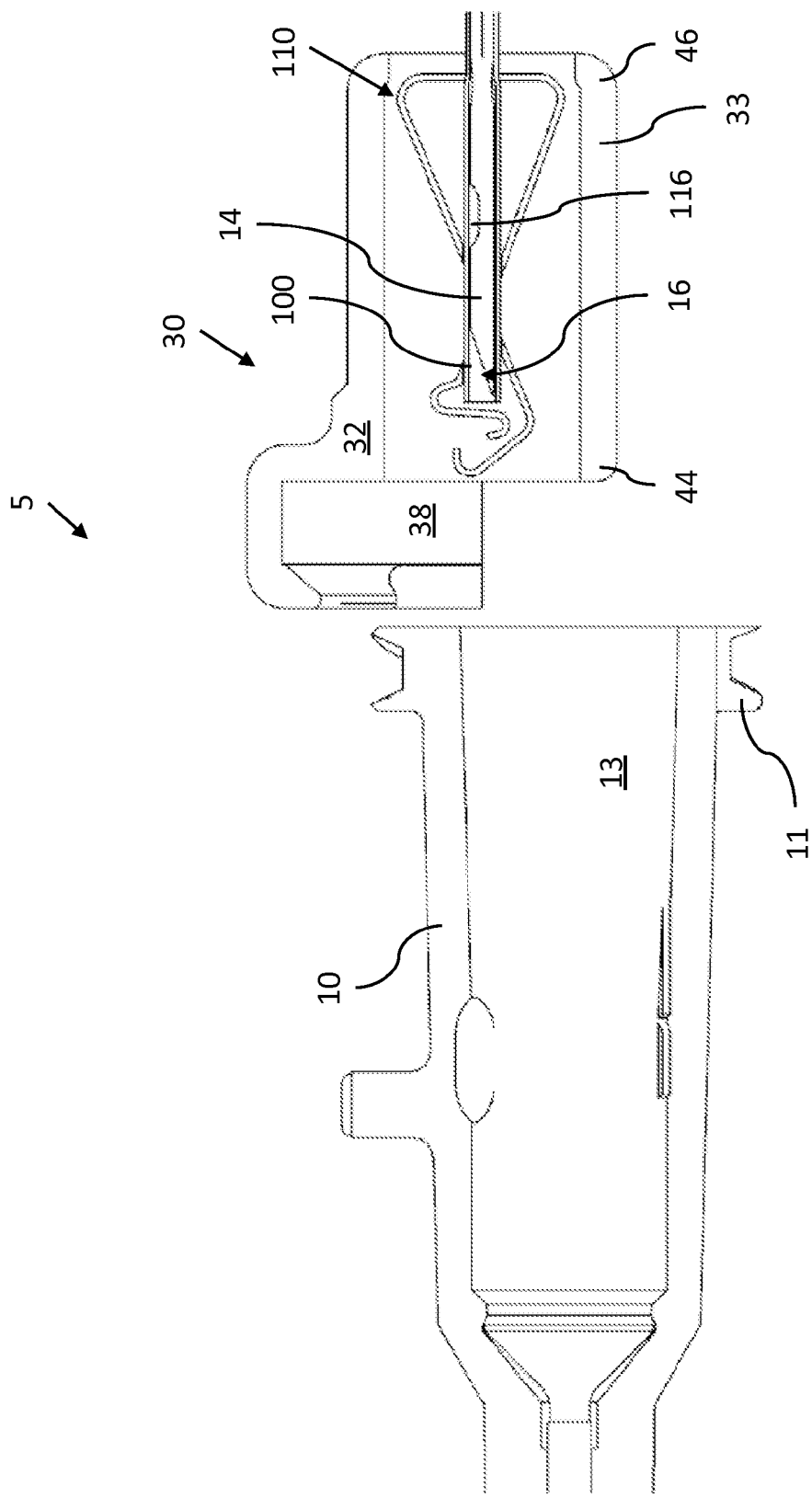
Figure 36:
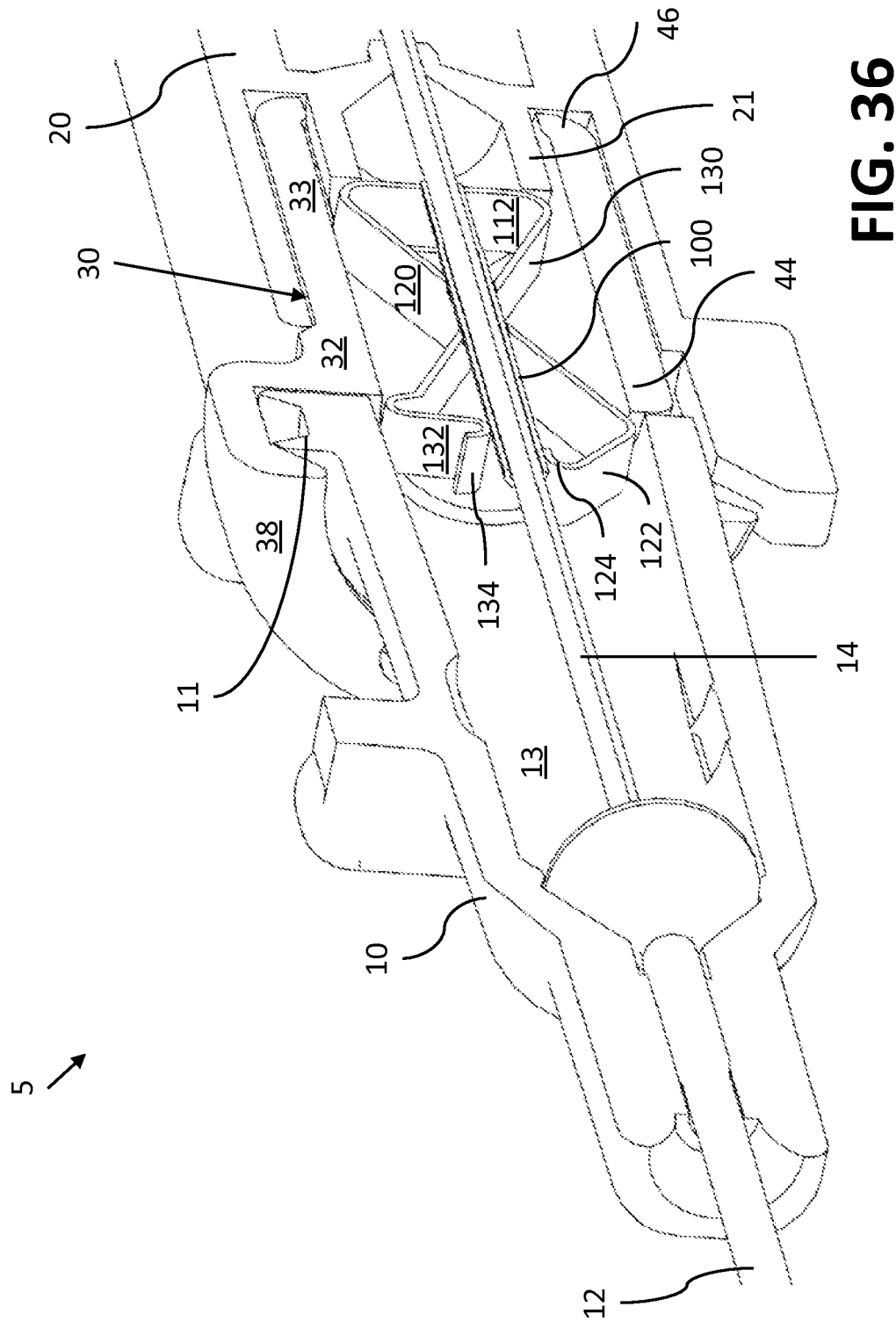
FIGS. 36-41 show perspective views of a needle device including a needle shield assembly progressing from a non-shielding position (FIG. 36) to a shielding position (FIG. 41) according to embodiments of the invention.
Figure 37:
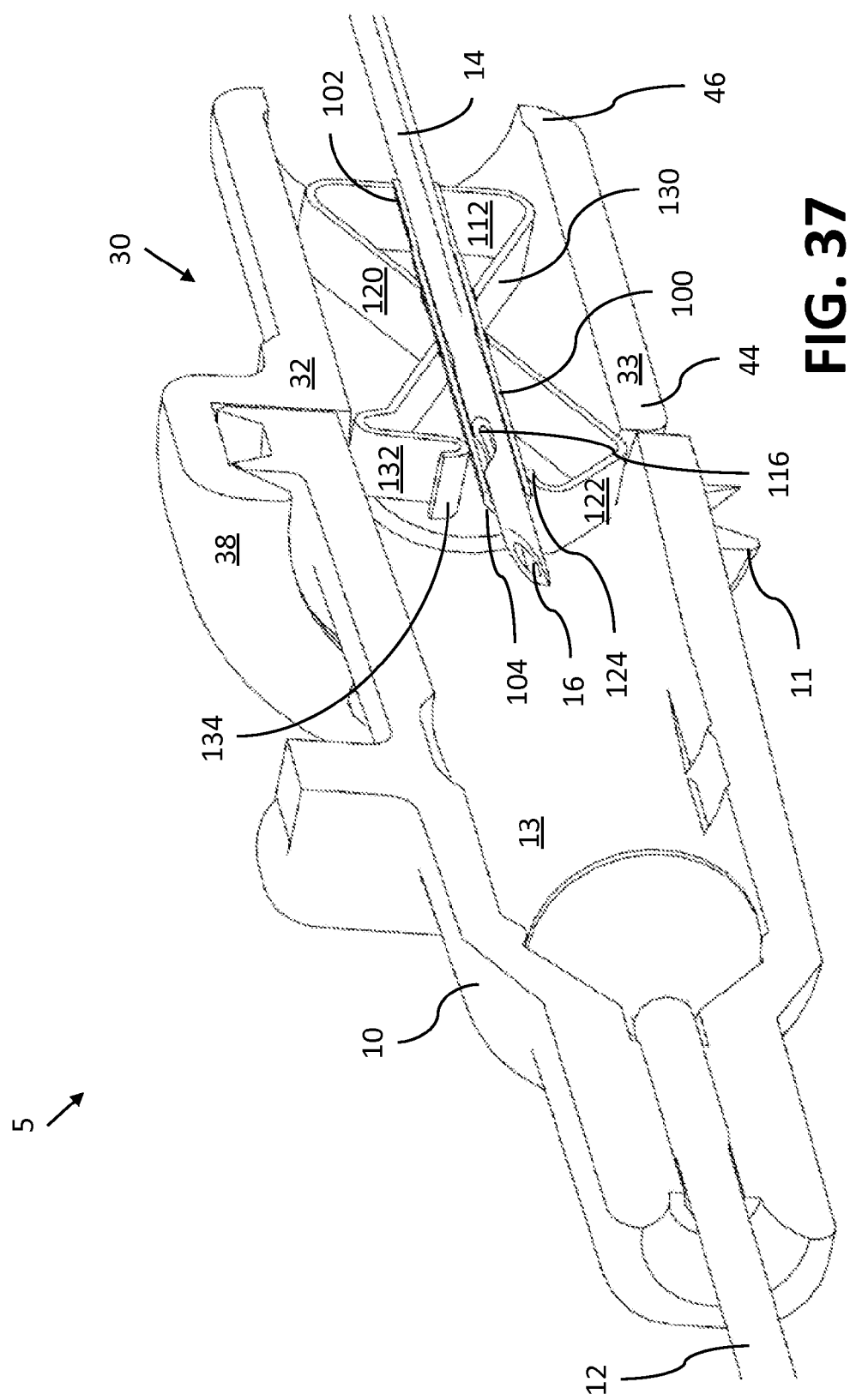
Figure 38:
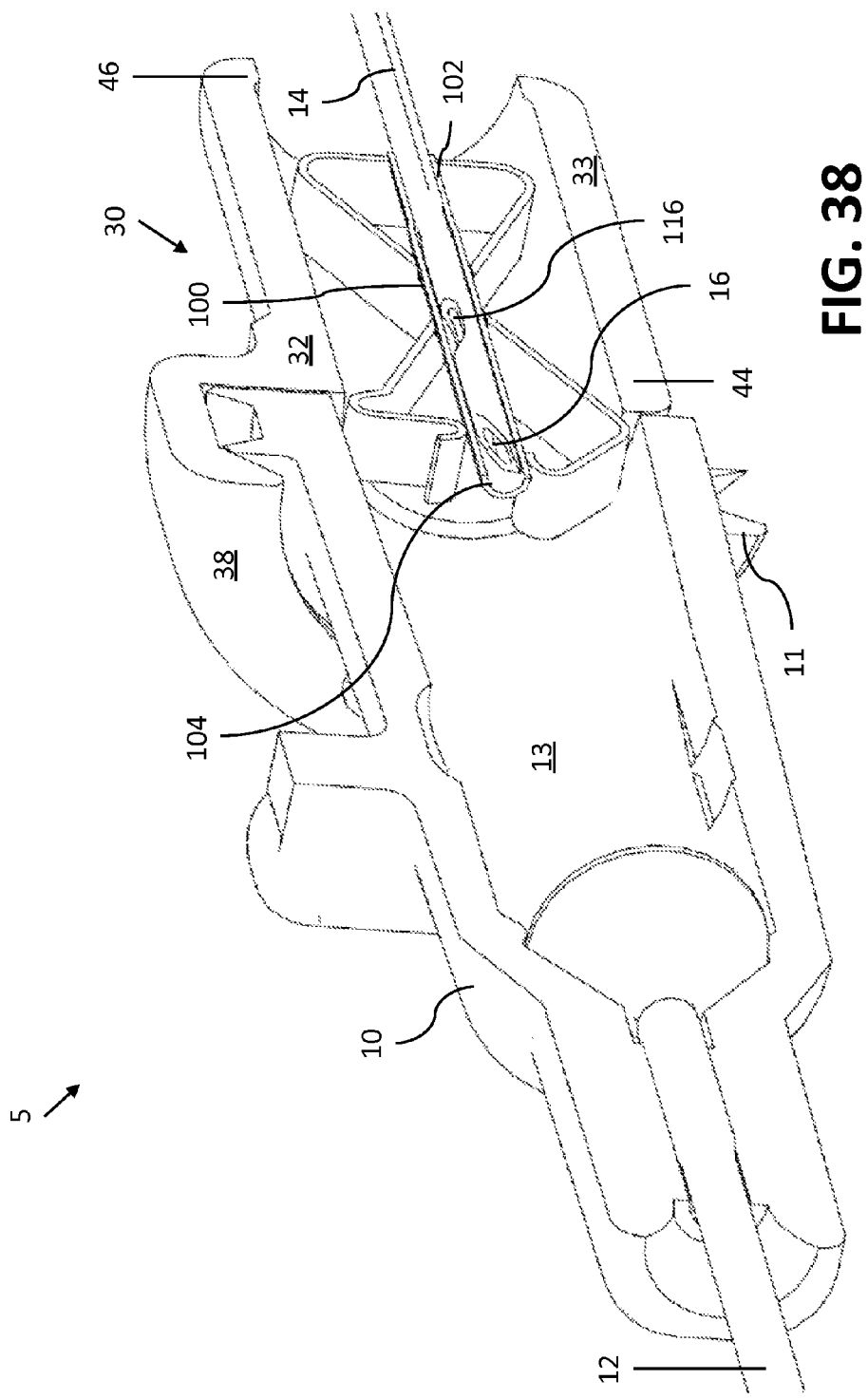
Figure 39:
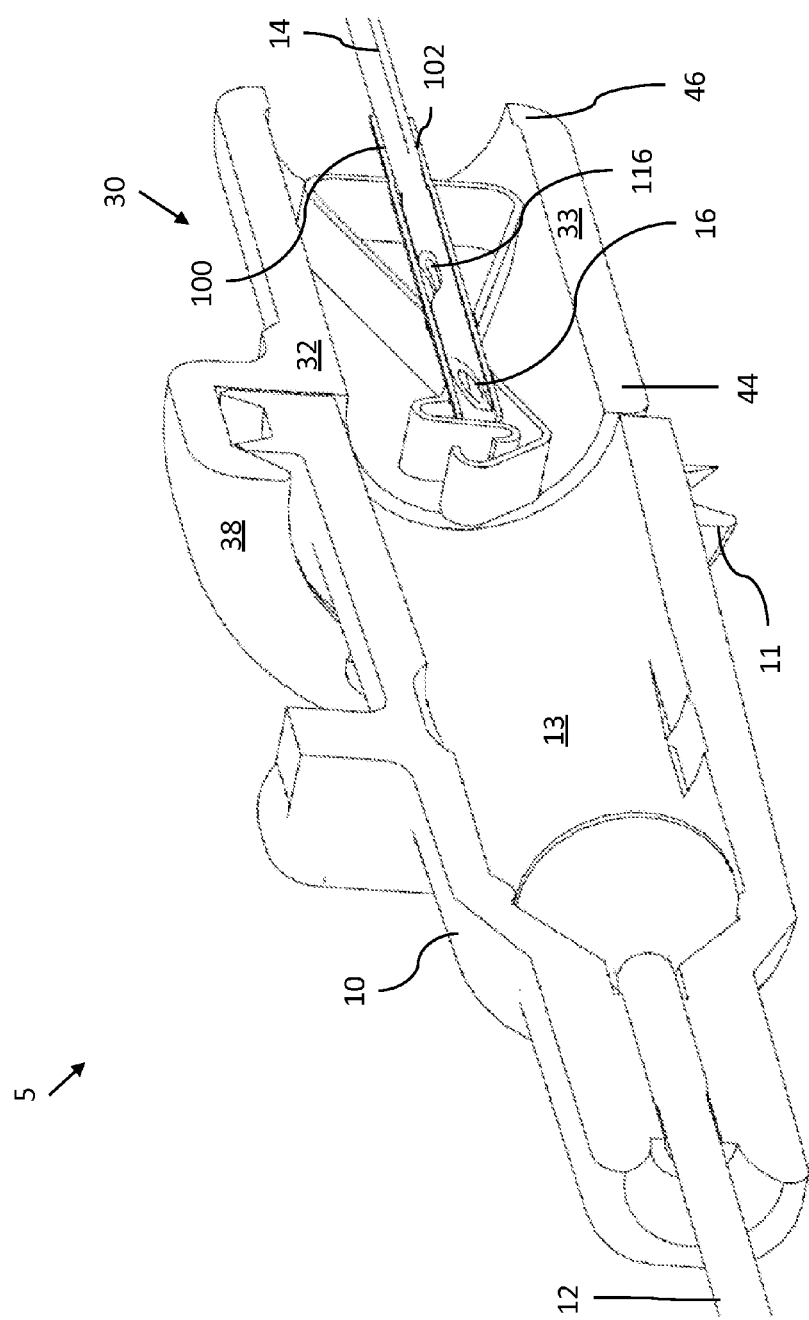
Figure 40:
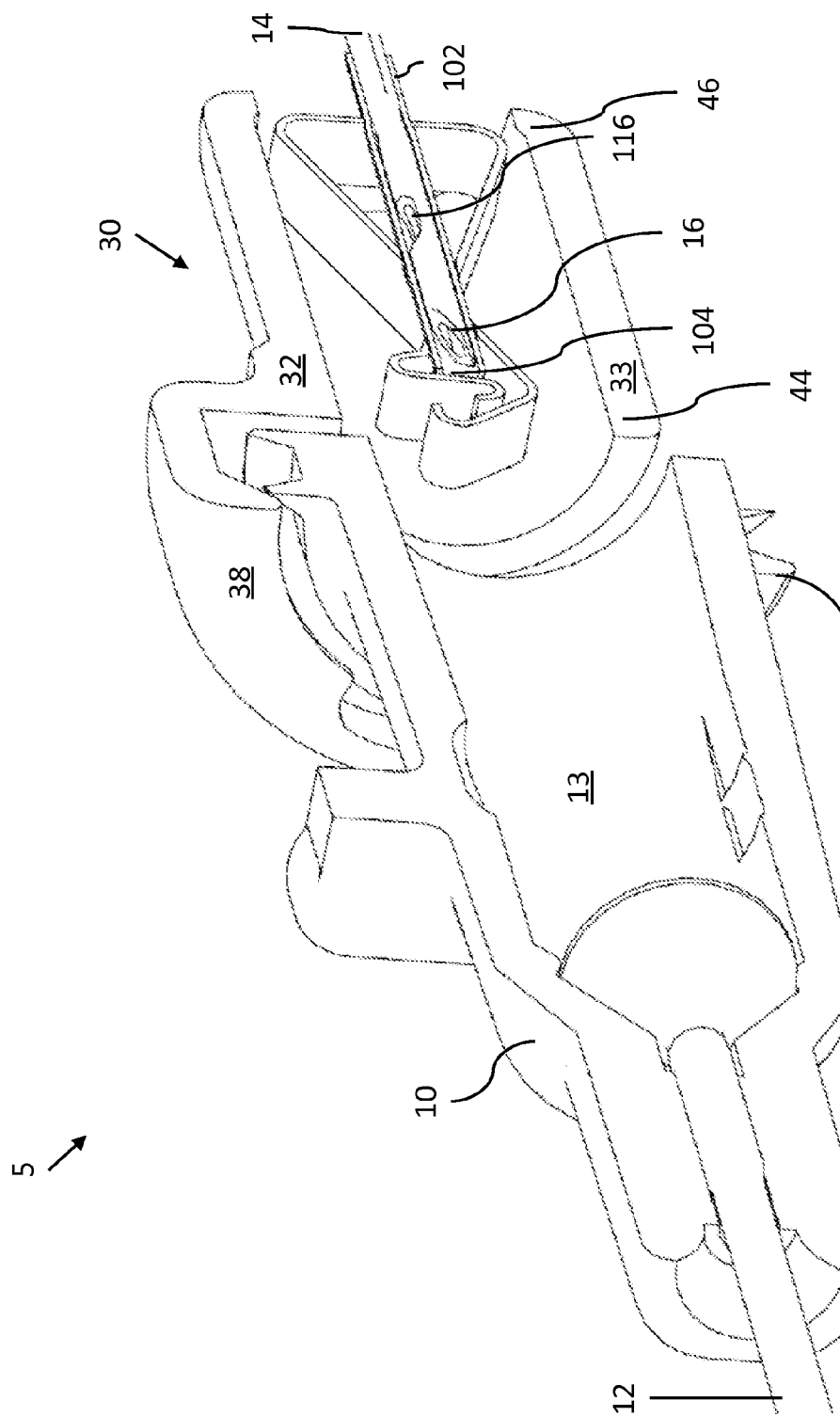
Figure 41:
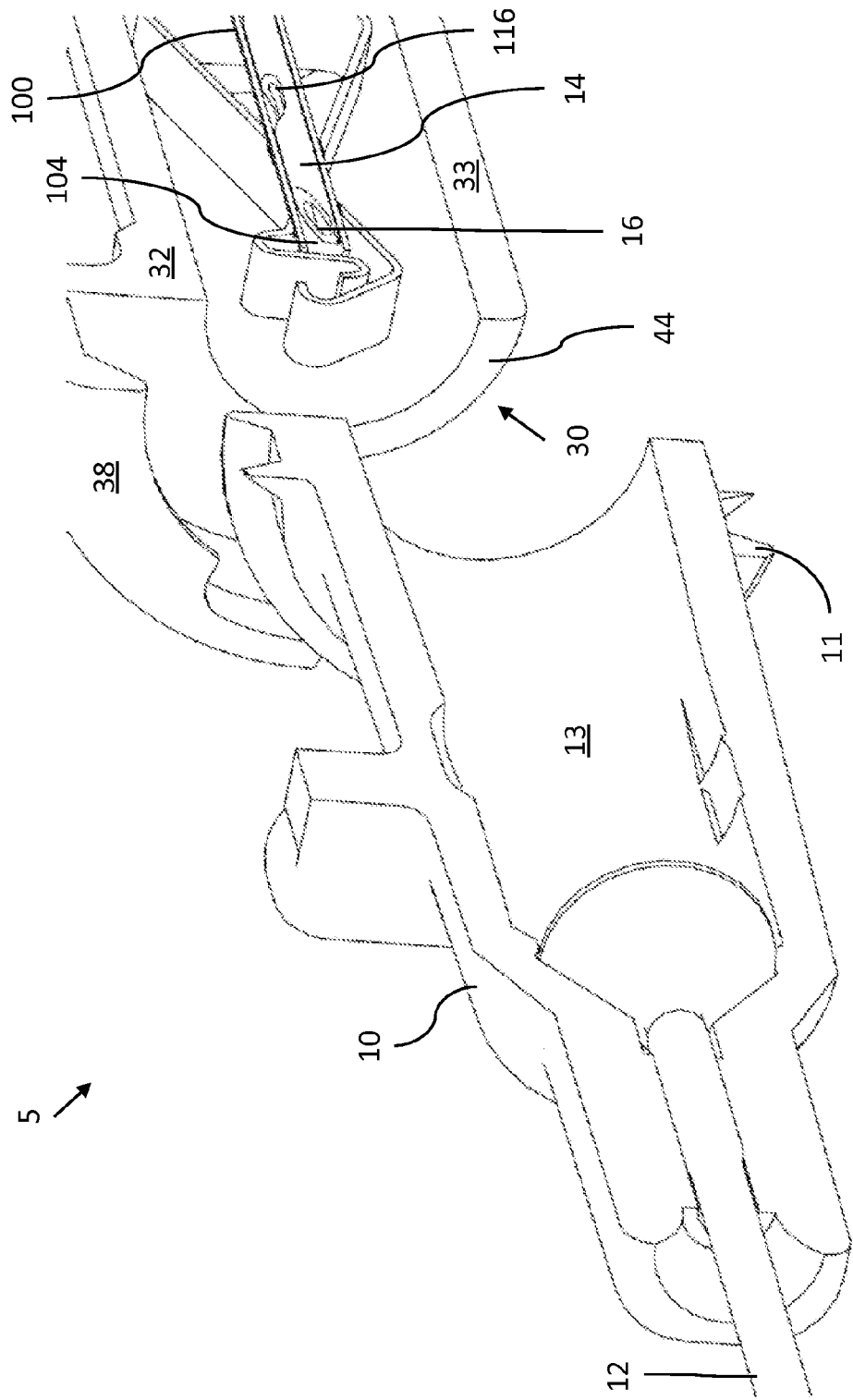
Figure 42:
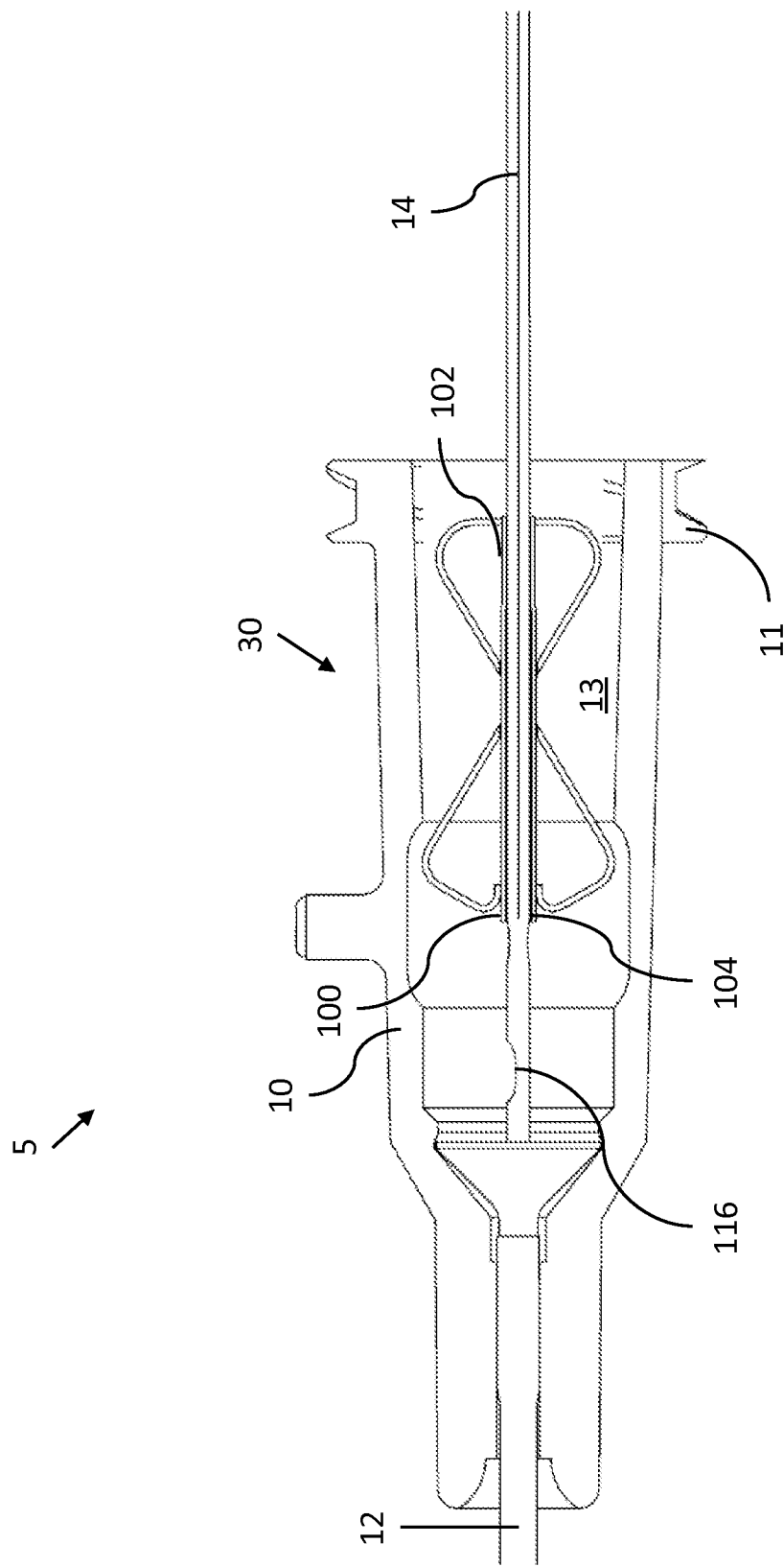
FIGS. 42-45 show cross sectional views of a needle device including a needle shield assembly progressing from a non-shielding position (FIG. 42) to a shielding position (FIG. 45) according to embodiments of the invention.
Figure 43:
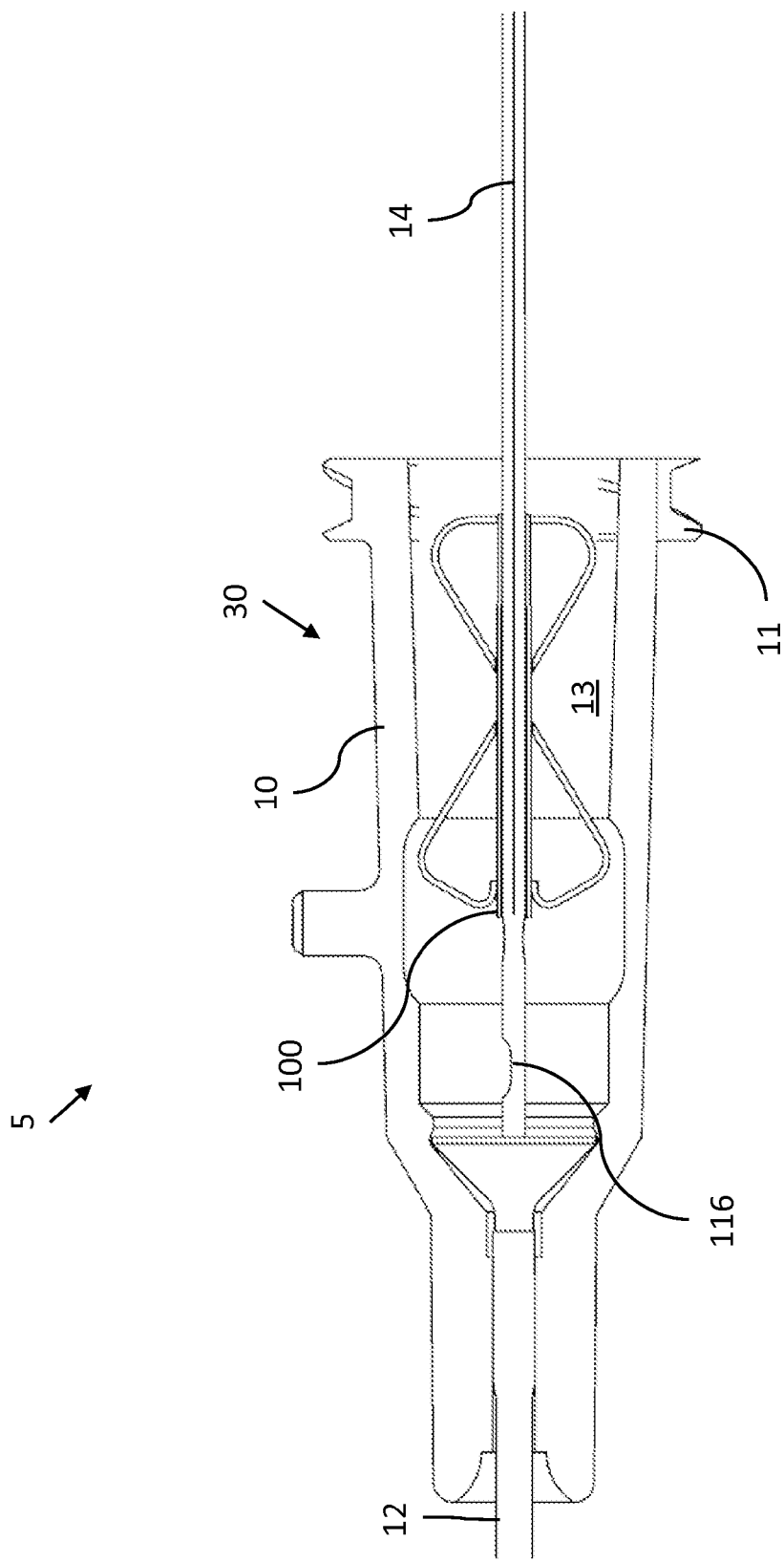

In response to the clip needle guard 110 moving proximally out of the hub 10, from the non-shielding position (FIG. 32) toward the shielding position (FIG. 33), the latch 32 moves generally radially outward relative to the longitudinal axis 17 (FIG. 29) of the needle 14 as shown in FIGS. 34-35.

With reference to FIGS. 26, 27, and 29-54, the above-described needle shield assembly 30 including clip needle guard 110 may further include a bushing 100. As discussed above, bushing 100 is substantially tubular in shape, and has an inner surface and an outer surface. Bushing 100 is disposed about needle 14 in a sleeve-like fashion. In a non-shielding position, as shown in FIGS. 26, 29-32, 36-38, 42-43, 46-47, and 50-51, axially extending arms 120, 130 are biased radially inward at their distal ends against the outer surface of bushing 100. The biasing force may be provided by, e.g., a spring or hinged action of clip needle guard 110. In the shielding position, as shown in FIGS. 27, 33-35, 39-41, 44-45, 48-49, and 52-54, the sharp distal tip 16 is positioned within the bushing 100, and at least a portion of the needle clip guard 110 extends over a distal end of the bushing 100, blocking sharp distal tip 16 of the needle 14 from moving in a distal direction and emerging from a distal end of bushing 100.

As noted above, needle 14 may include an enlarged diameter portion 19 which may be, e.g., a crimp in needle 14. As shown in detail in FIG. 31, bushing 100 may include a proximal inner diameter 102 that is smaller than the enlarged outer diameter portion 19 of needle 14, and a distal inner diameter 104 that is larger than the enlarged outer diameter portion 19 of needle 14. Enlarged diameter portion 19 may be accommodated by distal inner diameter 104 of bushing 100, allowing needle 14 to enter bushing 100 at the distal end and continue to move proximally until enlarged diameter portion 19 reaches a the point 103 where the inner diameter of bushing 100 transitions from the larger distal diameter 104 to the smaller proximal diameter 102. Point 103 and smaller proximal inner diameter 102 act as a stop for enlarged diameter portion 19 of needle 14, preventing it from proceeding any further in the proximal direction.

In embodiments such as shown in FIGS. 26-54, in which needle blocker 39 includes a clip needle guard 110, bushing 100 may have axial length 105 that is greater than or equal to an axial length 106 of the clip needle guard 110. As shown in FIGS. 26, 29-32, 36-38, 42-43, 46-47, and 50-51, in embodiments including a bushing 100, clip needle guard 110 contacts the outer surface of bushing 100, and does not contact an outer surface of needle 14 itself in the non-shielding position. An axial drag force between the outer surface of needle 14 and the inner surface of bushing 100 is less than an axial drag force between the outer surface of bushing 100 and clip needle guard 110. This avoids potential drag from clip needle guard 110 on needle 14 that could otherwise slow or impede proximal movement of needle 14 toward the shielding position, because any frictional drag occurs on bushing 100 instead of needle 14.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A needle device comprising:
   a needle having a longitudinal axis, a proximal end, and a sharp distal tip;
   a bushing disposed about the needle, wherein the bushing has an inner surface, a radially outward-facing surface, a proximal end, and a distal end; and
   a needle blocker,
   wherein in a non-shielding position, the needle blocker is biased radially inward against the radially outward-facing surface of the bushing between the proximal end and the distal end of the bushing, and
   wherein in a shielding position, the sharp distal tip is positioned within the bushing, and the needle blocker lies at least partially across a distal opening of an axial lumen of the bushing, blocking distal movement of the sharp distal tip of the needle.

2. The needle device of claim 1,
   wherein the needle further comprises an enlarged outer diameter portion, and
   wherein the bushing further comprises:
   a proximal inner diameter that is smaller than the enlarged outer diameter portion of the needle; and
   a distal inner diameter that is larger than the enlarged outer diameter portion of the needle.

3. The needle device of claim 1, further comprising:
   a needle shield assembly associated with the needle and moveable from the non-shielding position to the shielding position in which the sharp distal tip is covered by at least part of the needle shield assembly;
   a hub having an engaging member on an exterior side thereof; and
   a latch associated with the needle shield assembly, wherein the latch includes a housing and a latch member, and
   wherein in the non-shielding position, the latch member engages the engaging member on the exterior of the hub.

4. The needle device of claim 3, further comprising
   a locking member operably connected to the needle shield assembly, and located at least partially within the hub when the needle shield assembly is in the non-shielding position, thereby locking the latch to the hub, and such that in response to the needle shield assembly moving into the shielding position, the locking member moves generally proximally, thereby unlocking the latch.

5. The needle device of claim 4, wherein the needle shield assembly further comprises:
   a carrier for carrying the needle blocker; and
   a spring for biasing the needle blocker distally and toward the longitudinal axis, such that in the non-shielding position the needle blocker contacts the bushing,
   wherein the needle blocker is substantially spherical.

6. The needle device of claim 5, wherein the carrier includes:
   a channel in which the needle blocker is carried,
   an axial lumen slidable relative to and dimensioned to accommodate the bushing, and
   an external shroud including an opening through which a portion of the needle blocker projects in the non-shielding position, wherein in the shielding position, the needle blocker at least partially occupies the axial lumen, and
   wherein the bushing has a proximal outer diameter and a distal outer diameter, the proximal outer diameter being smaller than the distal outer diameter, and
   wherein the external shroud further includes a hole at a proximal end of the axial lumen, the hole being dimensioned to accommodate the proximal outer diameter of the bushing and not accommodate the distal outer diameter of the bushing.

7. The needle device of claim 3, wherein the needle blocker further comprises a clip needle guard, the clip needle guard including:
   a first axially extending arm, wherein the first axially extending arm includes a radially extending member on a distal end thereof,
   wherein in the shielding position, the radially extending member blocks distal movement of the sharp distal tip of the needle.

8. The needle device of claim 7, wherein the clip needle guard further comprises:
   a proximal wall; and
   a second axially extending arm,
   wherein the first axially extending arm and the second axially extending arm extend in a distal direction from the proximal wall,
   wherein the proximal wall further includes an opening through which the needle passes, and
   wherein, in the non-shielding position, the clip needle guard is disposed at least partially within the hub, and a radially outermost portion of at least one of the first axially extending arm and the second axially extending arm retains a position of the hub relative to the latch.

9. The needle device of claim 8, wherein the bushing has an axial length that is greater than or equal to an axial length of the clip needle guard, such that the clip needle guard contacts the radially outward-facing surface of the bushing,
   wherein the bushing has a proximal outer diameter and a distal outer diameter, the proximal outer diameter being smaller than the distal outer diameter, and
   wherein the opening in the proximal wall is dimensioned to accommodate the proximal outer diameter of the bushing and not accommodate the distal outer diameter of the bushing.

10. The needle device of claim 7, wherein the bushing has an axial length that is greater than or equal to an axial length of the clip needle guard, such that the clip needle guard contacts an radially outward-facing surface of the bushing.

11. The needle device of claim 1, wherein the needle further comprises a side opening for blood visualization.

12. A needle device comprising:
    a hub having an engaging member on an exterior thereof;
    a needle having a longitudinal axis, a proximal end, and a sharp distal tip;
    a latch including a housing and a hooked latch member disposed at a distal end of the housing; and
    a clip needle guard disposed at least partially within the hub and at least partially within the housing of the latch, and movable between a non-shielding position and a shielding position,
    wherein the clip needle guard includes:
    a first axially extending arm, wherein the first axially extending arm includes a radially extending member on a distal end thereof,
    wherein in the non-shielding position, the hooked latch member engages the engaging member on the exterior of the hub, and
    wherein in the shielding position, the radially extending member blocks distal movement of the sharp distal tip of the needle.

13. The needle device of claim 12, wherein the clip needle guard further comprises:
    a proximal wall; and
    a second axially extending arm,
    wherein the first axially extending arm and the second axially extending arm extend in a distal direction from the proximal wall,
    wherein the proximal wall further includes an opening through which the needle passes, and
    wherein, in the non-shielding position, a radially outermost portion of at least one of the first axially extending arm and the second axially extending arm retains a position of the hub relative to the latch.

14. The needle device of claim 12, wherein in response to the clip needle guard moving proximally out of the hub, the latch moves generally radially outward relative to the longitudinal axis of the needle.

15. The needle device of claim 12, wherein the hooked latch member extends circumferentially about a distal end of the housing.

16. The needle device of claim 15, wherein the hooked latch member comprises:
    a first member extending substantially radially outward relative to the housing,
    a second member extending substantially distally from a radially outward end of the first member in a direction substantially parallel to the housing, and
    a third member extending substantially radially inward from a distal end of the second member, forming a distal restraining surface of the latch.

17. The needle device of claim 12, wherein the engaging member comprises a flanged proximal end.

18. The needle device of claim 17, wherein the engaging member further comprises a threaded flanged proximal end.

19. The needle device of claim 12, wherein the needle further comprises a side opening for blood visualization.

* * * * *